United States Patent [19]

Ueda et al.

[11] Patent Number: 5,681,260

[45] Date of Patent: Oct. 28, 1997

[54] GUIDING APPARATUS FOR GUIDING AN INSERTABLE BODY WITHIN AN INSPECTED OBJECT

[75] Inventors: Yasuhiro Ueda, Kokubunji; Sakae Takehana, Machida; Hideyuki Adachi, Hachioji; Tatsuya Yamaguchi; Takeaki Nakamura, both of Hino; Masakazu Gotanda, Tsukui-gun; Masaaki Hayashi, Hachioji, all of Japan

[73] Assignee: Olympus Optical Co., Ltd., Tokyo, Japan

[21] Appl. No.: 352,433

[22] Filed: Dec. 9, 1994

Related U.S. Application Data

[63] Continuation of Ser. No. 994,971, Dec. 22, 1992, abandoned, which is a continuation of Ser. No. 567,463, Aug. 14, 1990, abandoned.

[30] Foreign Application Priority Data

| Sep. 22, 1989 | [JP] | Japan | 1-247494 |
| Apr. 25, 1990 | [JP] | Japan | 2-109696 |
| Apr. 25, 1990 | [JP] | Japan | 2-109697 |
| Apr. 25, 1990 | [JP] | Japan | 2-109698 |
| May 21, 1990 | [JP] | Japan | 2-131718 |

[51] Int. Cl.$^6$ .................................................. A61B 1/01
[52] U.S. Cl. ........................... 600/114; 600/117; 128/899
[58] Field of Search .................................. 600/102, 103, 600/117, 114, 9, 11–14; 604/95; 128/897, 898, 899

[56] References Cited

U.S. PATENT DOCUMENTS

| 2,863,458 | 12/1958 | Modny et al. | 600/12 |
| 3,043,309 | 7/1962 | McCarthy | 604/95 |
| 3,358,676 | 12/1967 | Frei et al. | 600/12 |
| 3,674,014 | 7/1972 | Tillander | 604/95 |
| 3,986,493 | 10/1976 | Hendren, III | |
| 4,054,128 | 10/1977 | Seufert et al. | 128/4 |
| 4,278,077 | 7/1981 | Mizumoto | 128/4 |

FOREIGN PATENT DOCUMENTS 2252107  8/1976  France.

OTHER PUBLICATIONS

Tillander, Selective Angiography with a Catheter Guided by a Magnet, IEEE Transactions on Magnetics, vol. MAG–6, No. 2, pp. 355–358, Jun. 1970.

*Primary Examiner*—Richard J. Apley
*Assistant Examiner*—John P. Leubecker
*Attorney, Agent, or Firm*—Armstrong, Westerman, Hattori, McLeland & Naughton

[57] ABSTRACT

A guiding apparatus for guiding an insertable body within an inspected object is provided with an insertable body to be inserted into an inspected object, a guided part provided in at least a part of the insertable body and to be magnetically guided and a guiding device provided outside the inspected object and to magnetically guide the guided part. The guiding device includes a guiding part for guiding the guided part and a driving device for moving the guiding part at least two-dimensionally, the guided part and guiding part are to generate a magnetic force acting between them and the guiding part is to guide the guided part with the magnetic force.

20 Claims, 40 Drawing Sheets

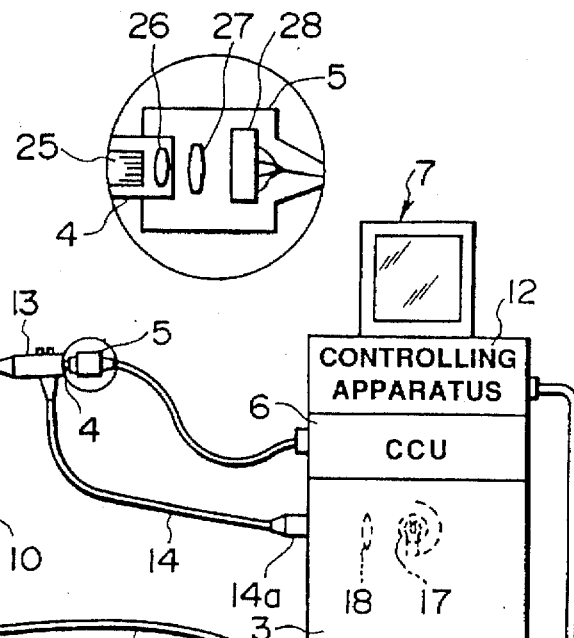
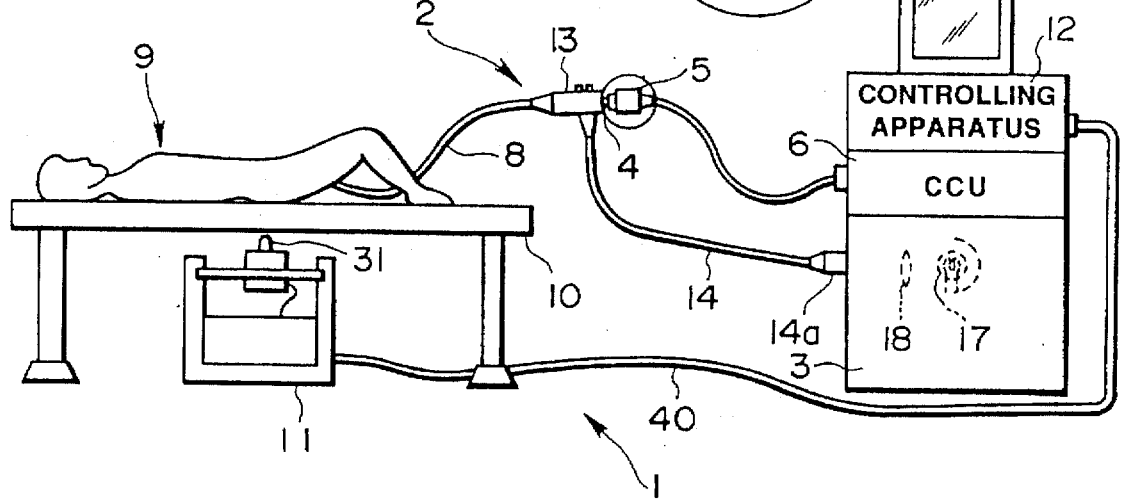
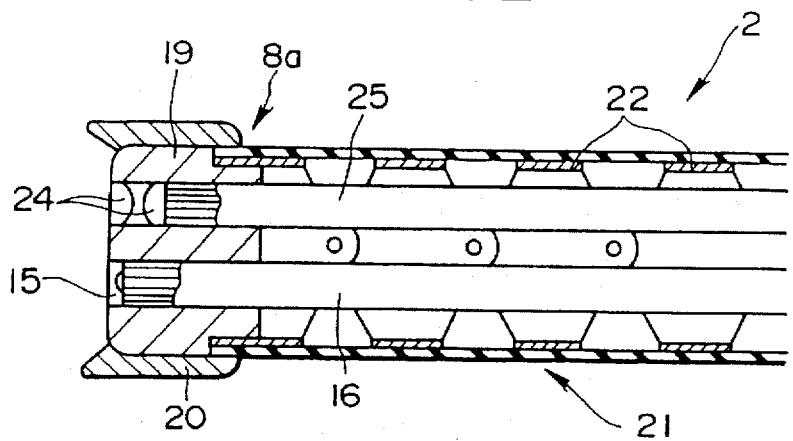

FIG. 7
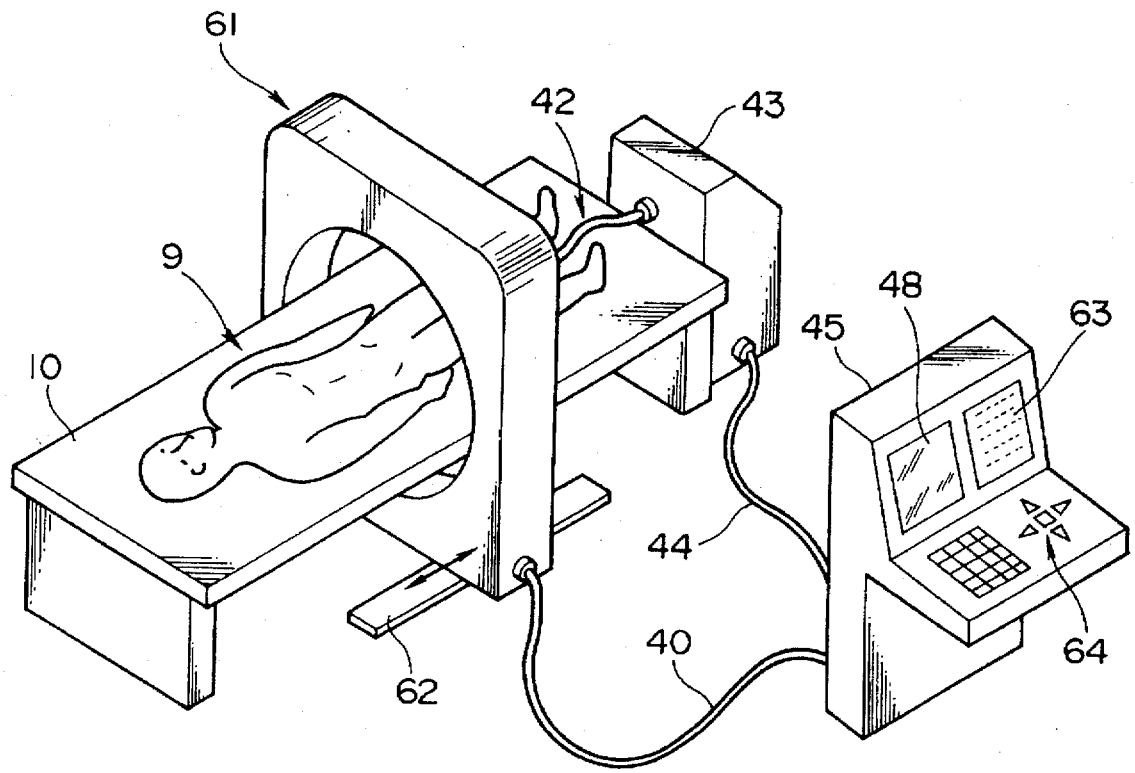
FIG. 8(A)     FIG. 8(B)
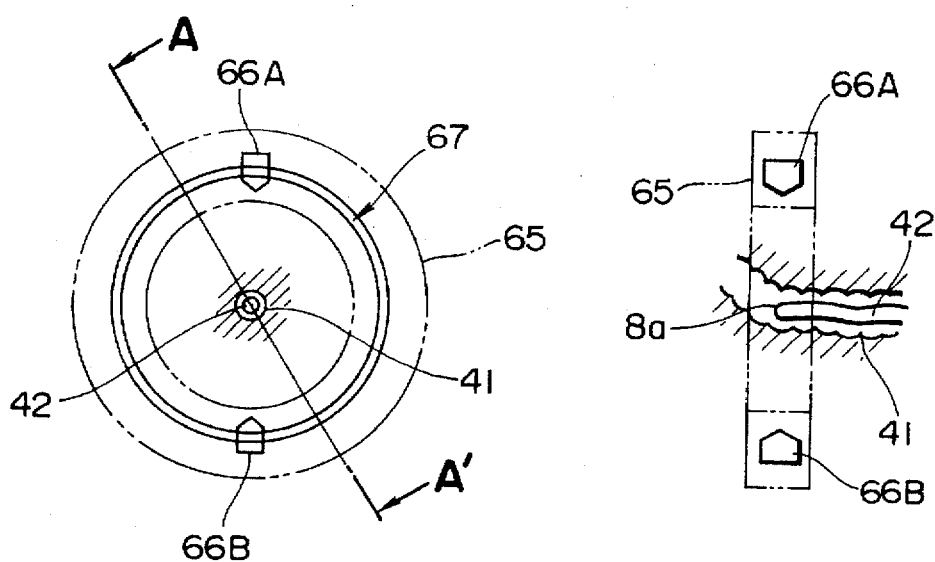

FIG.15
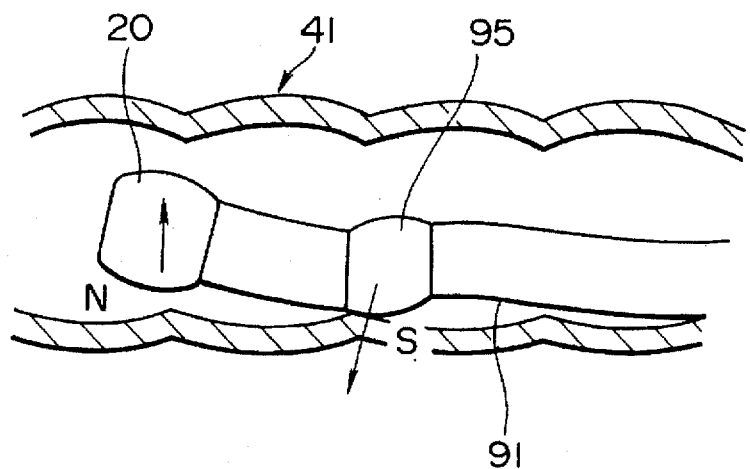
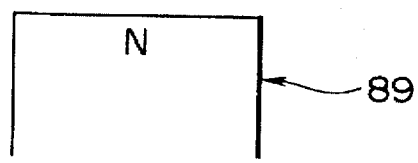
FIG.16
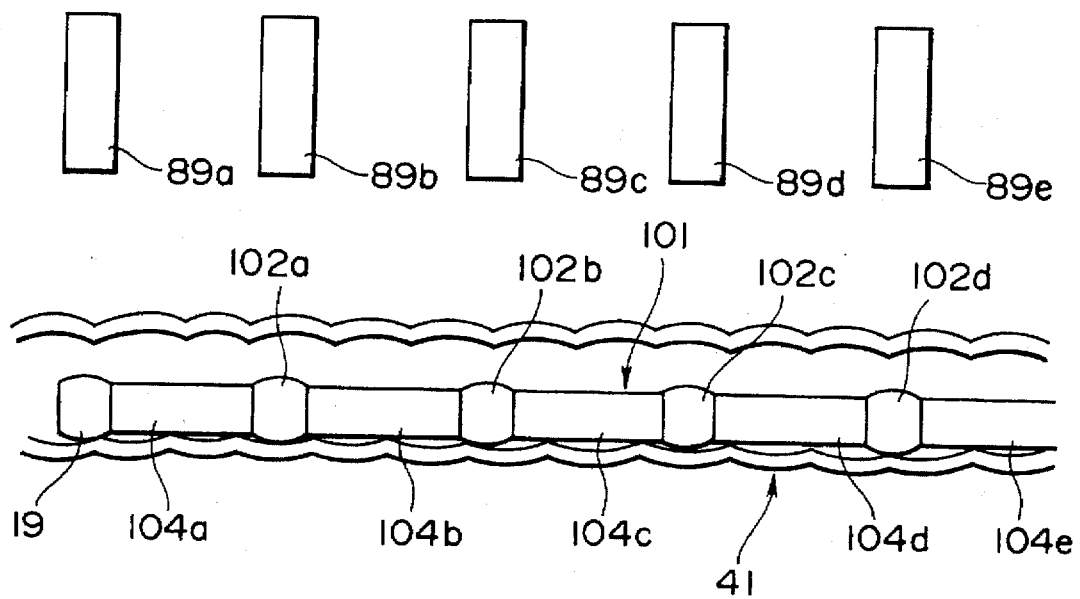

FIG. 32
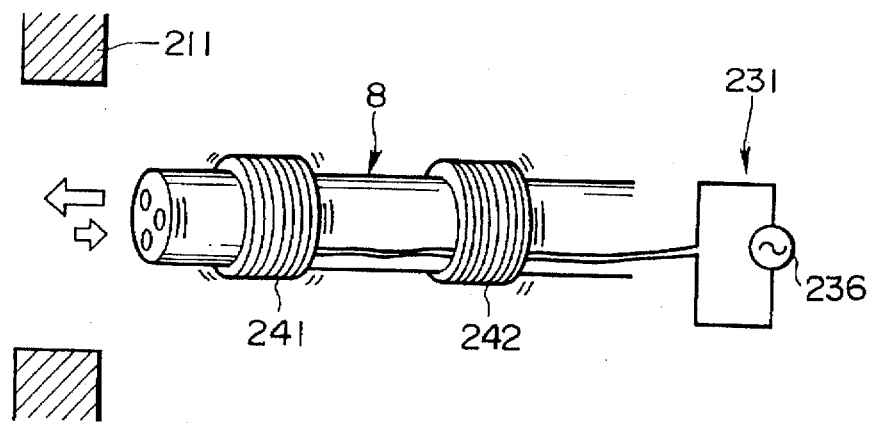
FIG. 33
FIG. 34(A)
FIG. 34(B)
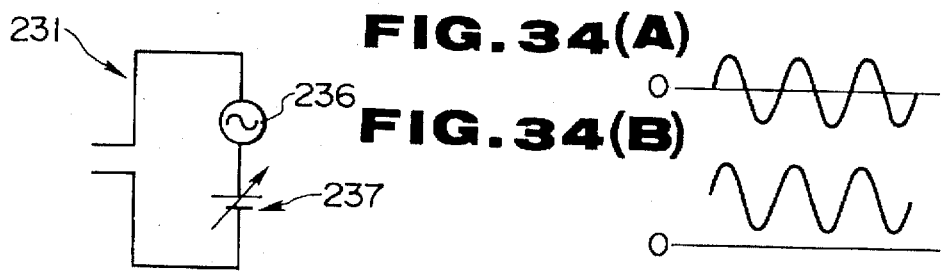
FIG. 35
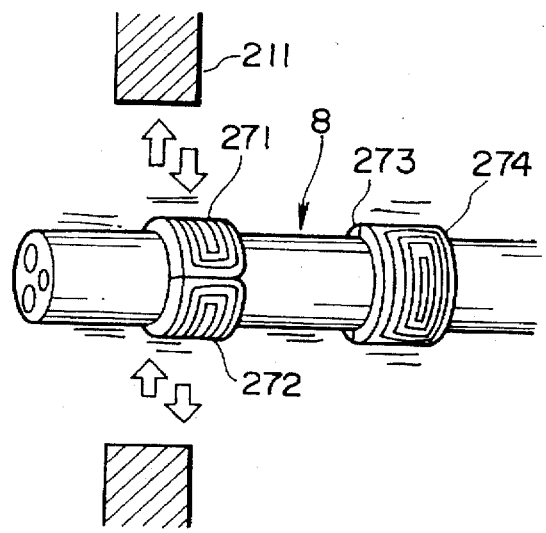

FIG.42

| VIDEO SIGNAL | MAGNETIC FIELD GENERATION | VIDEO SIGNAL | MAGNETIC FIELD GENERATION |
|---|---|---|---|
| A FIELD | B FIELD | A FIELD | B FIELD |

FIG.43

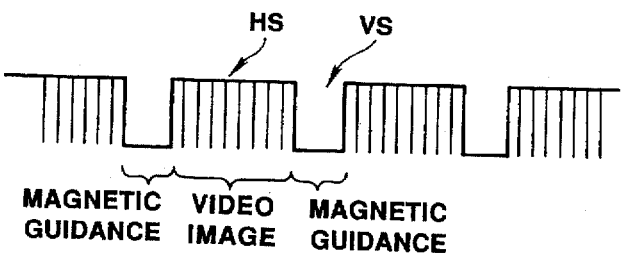

MAGNETIC GUIDANCE — VIDEO IMAGE — MAGNETIC GUIDANCE

FIG.44

| ← MAGNETIC GUIDANCE TIME | | | ORDINARY TIME → | | |
|---|---|---|---|---|---|
| MAGNETIC FIELD GENERATION | VIDEO SIGNAL | MAGNETIC FIELD GENERATION | VIDEO SIGNAL | MAGNETIC FIELD GENERATION | VIDEO SIGNAL |
| B FIELD | A FIELD | B FIELD | A FIELD | B FIELD | A FIELD |

FIG.45

| | MAGNETIC GUIDANCE | | MAGNETIC GUIDANCE | |
|---|---|---|---|---|
| | FROZEN PICTURE | REAL TIME PICTURE | FROZEN PICTURE | REAL TIME PICTURE |

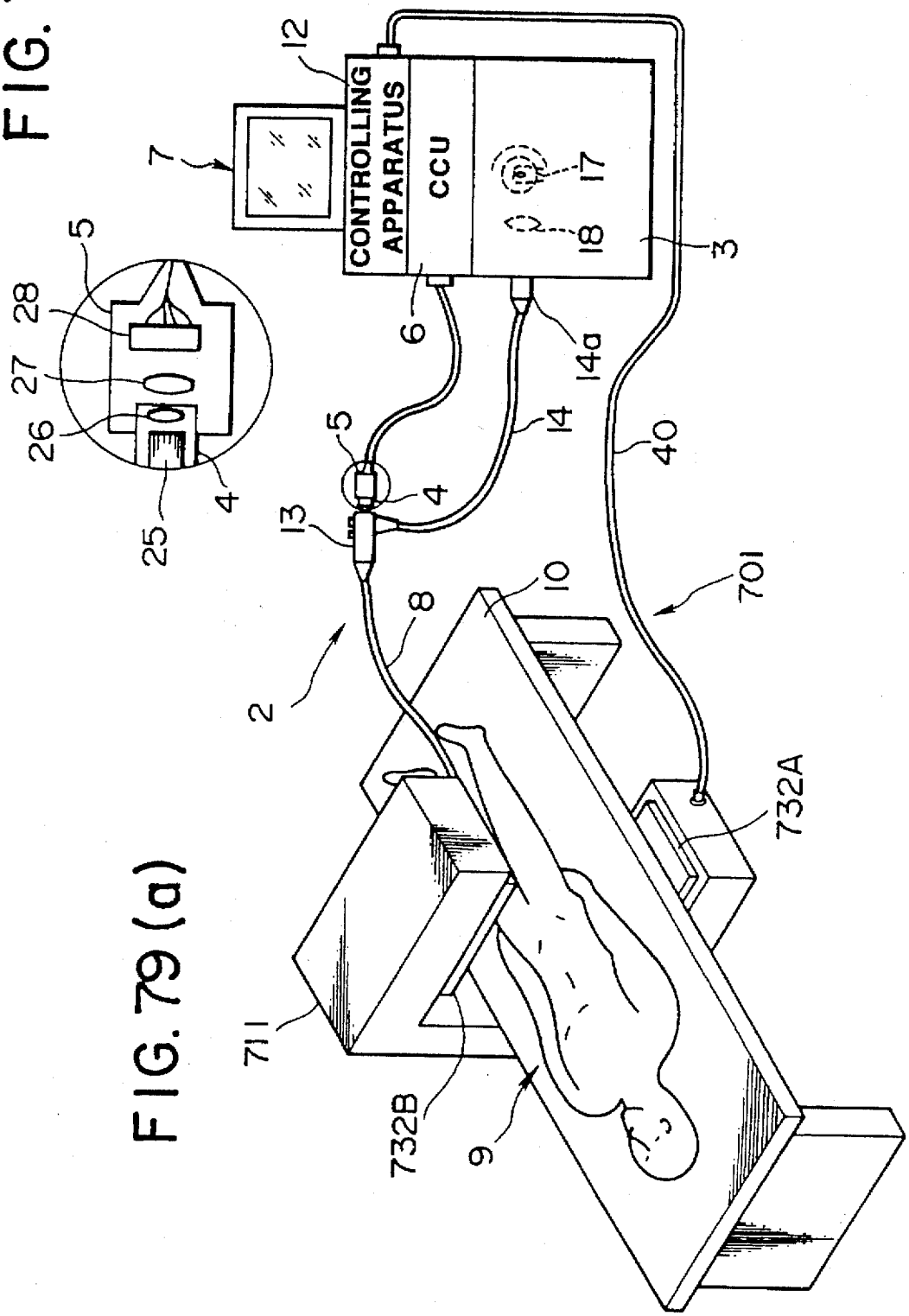

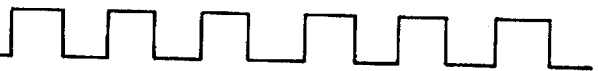
FIG. 83
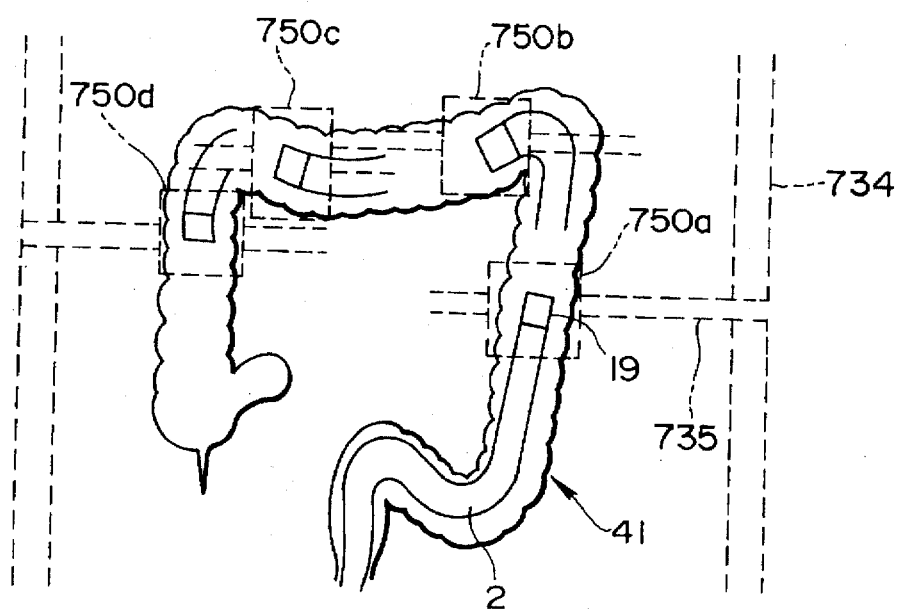

GUIDING APPARATUS FOR GUIDING AN INSERTABLE BODY WITHIN AN INSPECTED OBJECT

This application is a continuation of application Ser. No. 07/994,971 filed Dec. 22, 1992, now abandoned; which is a continuation of application Ser. No. 07/567,463, filed Aug. 14, 1990, now abandoned.

BACKGROUND OF THE INVENTION

1. Field of the Invention

This invention relates to a guiding apparatus for guiding an insertable body within an inspected object by utilizing a magnetic force.

2. Related Art Statement

Endoscopes have recently come to be extensively used in the medical and industrial fields.

In order to make an inspection or diagnosis with such endoscope, it is necessary to insert the insertable part of the endoscope into a body cavity or the like. In such case, the inserting course is so often bent that, unless by a skilled operator, the insertion will take time.

Therefor, in the publication of Japanese Utility Model Application Publication No. 5155/1980 is disclosed an art that a balloon is provided in an endoscope so that the endoscope may be automatically or auxiliary inserted into such tube cavity as of a large intestine by the expansion and contraction of this balloon.

Also, in the publication of Japanese Patent Application Laid Open No. 136014/1988 is disclosed an art that actuators made of a form memorizing alloy are provided so that the endoscope may be automatically bent and inserted along the bent form of such tube cavity as of a large intestine by controlling the electrical heating of the actuators.

Said two examples are effective as automatic inserting means for the object but it is necessary to provide a complicated actuator mechanism in the endoscope itself, the structure is complicated, therefore the insertable part of the endoscope can not help being made large in the diameter and the pain of the patient has been hard to reduce.

Also, on pages 1313 to 1318 of the "Stomach and Intestines" Vol. 9 No. 10 (1974) is disclosed an endoscope which is automatically inserted into the deep of a small intestine by utilizing the vermicular motion of the patient himself. This has a so soft insertable part of a diameter of about 5 mm. that there is an advantage that the pain of the patient is small. However, in this endoscope, it is necessary to make the insertable part long and to make the outside diameter of the insertable part extremely fine. Therefore, there are problems that the tip bending mechanism using the angle wire which has been conventionally used can not be provided and that, even if this is provided, the necessary bending will not be able to be realized. These problems relate to the reduction of the observing and treating performances. Thus, this endoscope has not been extensively prevalent.

Also, in the publications of Japanese Patent Application Laid Open No. 133237/1980, West German Patent Application Publication No. 1262276, U.S. Pat. Nos. 3,986,496 and 4,278,077 and Japanese Patent Application Publication No. 37939/1986 is disclosed an art that a ferromagnetic substance or magnet is provided in the insertable part of an endoscope or the like and this insertable part is magnetically guided from outside the body.

In the apparatus shown in the publication of said Japanese Patent Application Laid Open No. 33237/1980, the contact of the insertable part with the tube cavity wall is detected, the external magnetic field is varied and the insertable part is returned to the center within the tube cavity. The external magnetic field generating apparatus can be moved in the one dimension direction. However, in this apparatus, the external magnetic field generating apparatus is movable in one direction but, in the other directions, the guidance of the insertable part is controlled by varying the external magnetic field and therefore there are problems that the guidance controllablity is low and the magnetic field generating apparatus becomes large. In this apparatus, there are also problelms that, as the insertable part is floated in the center of the tube cavity, a strong magnetic field generating apparatus is required, it is necessary to provide a contact sensor, the apparatus becomes large and the structure of the insertable part of the endoscope is complicated.

In the apparatus shown in the publications of said West German Patent Application Publication No. 1262276, U.S. Pat. No. 4,278,077 and Japanese Patent Application Publication No. 37939/1986, the insertable part is guided by moving the external magnetic field generating part but it is necessary for the operator to manually operate the magnetic field generating part, therefore the guiding operation while observing is difficult and the guidance controllability is low.

Further, when a magnetic substance is used for the guided part of the insertable part, the magnetic substance will be likely to generate heat. Thus, in the medical endoscope, there is a problem in the safety.

Now, when the insertable part is inserted into a bent object to be inspected, the state (form) of the insertable part will not be able to be easily known. In the endoscope apparatus wherein the insertable part is magnetically guided as described above, X-rays or the like have been used to confirm the state of the insertable part. However, the use of X-rays has a problem of the radioactive ray emission and is not desirable.

As shown in said West German Patent Application Publication No. 1262276, in case the insertable part is to be guided by merely utilizing the attraction of a magnet, the insertable part has been guided by operating a guiding part by a strong magnet or the like, for example, from above the abdomen of the patient by using an attraction in one direction between the guided part of the insertable part and the guiding part outside the body. However, there are problems that, with the traction in the body surface direction, the insertable part will be pulled so as to bite into the body cavity wall, will be therefore hard to insert deep into the body cavity, the attraction will be greatly different depending on the distance between the guiding part outside the body and the insertable part and the guidance controllability will be low.

Also, in the case of guiding the insertable part within a tube cavity as described above, due to the friction between the insertable part and tube cavity wall and the complicated tube cavity structure, the insertable part will be hard to insert.

OBJECTS AND SUMMARY OF THE INVENTION

An object of the present invention is to provide a guiding apparatus and method for magnetically guiding an insertable body within an inspected object wherein the guidance controllability in the case of guiding is high.

Another object of the present invention is to provide a guiding apparatus for magnetically guiding an insertable body within an inspected objecte wherein a guiding apparatus outside the inspected object is prevented from becoming large.

A further object of the present invention is to provide a guiding apparatus for magnetically guiding an insertable body within an inspected object wherein the guidance controllability in the case of guiding is high and a guided part provided in the insertable body can be prevented from generating heat.

A further object of the present invention is to provide a guiding apparatus for magnetically guiding an insertable body within an inspected object wherein the position of the insertable body can be detected without the emission of radioactive rays.

A further object of the present invention is to provide a guiding apparatus for magnetically guiding an insertable body within an inspected object wherein the insertability of the inserted body can be elevated.

The guiding apparatus of the present invention comprises an insertable body to be inserted into an inspected object, a magnetically guided part provided in at least one part of said insertable body and a guiding means provided outside said inspected object and magnetically guiding said guided part. Said guiding means includes a guiding part guiding said guided part and a driving means moving the guiding part at least two-dimensionally. The guided part and guiding part are to generate a magnetic force acting between them. The guiding part is to guide the guided part by using said magnetic force.

The guiding apparatus is further provided, for example, with a position detecting means for detecting at least a two-dimensional position of the guided part and a means for vibrating the guided part by varying the magnetic force acting between the guided part and guiding part.

Also, said guided part includes, for example, a coreless coil generating a magnetic field when electrified.

Said guided part and guiding part will generate a magnetic force so as to be balanced in at least one direction, for example, even if the force acting on said guided part is small.

It is apparent that, in this invention, working modes different in a wide range can be formed on the basis of this invention without deviating from the spirit and scope of the invention. This invention is not restricted by its specific working modes except being limited by the appended claims.

BRIEF DESCRIPTION OF THE DRAWINGS

FIGS. 1(a) to 4 relate to the first embodiment of the present invention.

FIGS. 1(a) and 1(b) are explanatory views showing the whole of an endoscope apparatus.

FIG. 2 is a sectioned view showing a tip part of an insertable part of an endoscope.

FIG. 4 is an explanatory view showing an insertable part as being inserted into a large intestine.

FIG. 5 is an explanatory view showing the whole of an endoscope apparatus.

FIG. 6 is an elevation of an operating part.

FIGS. 7 to 9 relate to the third embodiment of the present invention.

FIG. 7 is a perspective view showing the whole of an endoscope apparatus.

FIG. 8(A) is an explanatory view showing a magnetic force generating apparatus.

FIG. 8(B) is an explanatory view showing a sectioned view on line A—A' in FIG. 8(A).

FIG. 10 is an explanatory view showing an endoscope as inserted from a nasal cavity into a small intestine.

FIG. 11 is a sectioned view showing an insertable part of an endoscope on the tip side.

FIG. 12 is an explanatory view showing an affected part within a small intestine as being observed with an endoscope.

FIG. 13 is an explanatory view showing an insertable part as passing through the pyloric region of a stomach.

FIGS. 14 and 15 relate to the fifth embodiment of the present invention.

FIG. 14 is a sectioned view showing an insertable part of an endoscope on the tip side.

FIG. 15 is an explanatory view showing an insertable part as being inserted into a large intestine.

FIGS. 16 to 19 relate to the sixth embodiment of the present invention.

FIG. 16 is an explanatory view showing the formation of an essential part of an endoscope apparatus.

FIG. 17 is an explanatory view showing an insertable part as being inserted into a large intestine.

FIG. 18 is an explanatory view showing a driving system of a magnetic force generating part.

FIG. 19 is an explanatory view showing the driving system of FIG. 18 in another state.

FIGS. 20(a) to 22 relate to the seventh embodiment of the present invention.

FIGS. 20(a) and 20(b) are explanatory views showing the whole of an endoscope apparatus.

FIG. 22 is a block diagram showing the formation of a controlling apparatus.

FIG. 23 is an explanatory view showing the whole of an endoscope apparatus.

FIG. 24 is an explanatory view showing a hall sensor unit.

FIG. 28 is an explanatory view showing an essential part of an endoscope apparatus.

FIG. 29 is a perspective view showing the whole of an endoscope apparatus.

FIG. 30 is a sectioned view showing a tip part of an insertable part of an endoscope.

FIG. 31 is an explanatory view showing an essential part of an endoscope apparatus of a modification of this embodiment.

FIGS. 32 to 34 relate to the 13th embodiment of the present invention.

FIG. 32 is an explanatory view showing an essential part of an endoscope.

FIG. 33 is a circuit diagram showing the formation of a control apparatus in a modification of this embodiment.

FIGS. 34(A) and (B) are waveform diagrams showing currents passed through coreless coils in the respective modifications.

FIG. 35 is an explanatory view showing an essential part of an endoscope apparatus in the 14th embodiment of the present invention.

FIG. 36 is an explanatory view showing an essential part of an endoscope apparatus.

FIG. 37 is a circuit diagram showing a circuit controlling the electrification of a coreless coil.

FIG. 38 is an explanatory view for explaining the operation of this embodiment.

FIGS. 39 to 42 relate to the 17th embodiment of the present invention.

FIG. 39 is an explanatory view showing the whole of an endoscope apparatus.

FIG. 40 is a block diagram showing the formation of an endoscope apparatus.

FIG. 41 is a block diagram showing the formation of a processing circuit.

FIG. 42 is an explanatory view for explaining the operation of this embodiment.

FIG. 43 is an explanatory view for explaining the operation of the 18th embodiment of the present invention.

FIG. 44 is an explanatory view for explaining the operation of the 19th embodiment of the present invention.

FIG. 45 is an explanatory view for explaining the operation of the 20th embodiment of the present invention.

FIGS. 46 and 47 relate to the 21st embodiment of the present invention.

FIG. 46 is a perspective view showing the whole of an endoscope apparatus.

FIGS. 48 and 49 relate to the 22nd embodiment of the present invention.

FIG. 48 is a sectioned view showing a tip part of an insertable part of an endoscope.

FIG. 50 is a side view of an endoscpe apparatus.

FIG. 51 is a perspective view of the endoscope apparatus.

FIG. 52 is an explanatory view showing a large intestine.

FIG. 53 is an explanatory view showing a modification of this embodiment.

FIG. 54 is a block diagram showing the formation of an insertable part positioning means.

FIGS. 55 and 56 are explanatory views each showing a magnetic field detecting means provided in the tip part of an insertable part.

FIG. 57 is an explanatory view showing the formation of an insertable part positioning means.

FIG. 58 is an explanatory view showing an insertable part as guided by a resiliency.

FIG. 59 is an explanatory view showing another example of a tip part of an insertable part as the insertable part is guided by a resiliency.

FIG. 60 is an explanatory view showing an insertable part as guided by using a resiliency and attraction.

FIG. 61 is an explanatory view showing the whole of an endoscope apparatus.

FIG. 62 is a sectioned view showing a tip part of an insertable part.

FIG. 63 is an explanatory view showing the whole of an endoscope apparatus.

FIG. 64 is a sectioned view showing a tip part of an insertable part.

FIG. 65 is an explanatory view showing the formation of an essential part of an endoscope apparatus.

FIG. 66 is a perspective view showing a permanent magnet provided in a tip part of an insertable part.

FIG. 67 is an explanatory view showing the movement of a tip part when an alternating magnetic field is generated.

FIG. 68 is an explanatory view showing the movement of a tip part when a static magnetic field is generated.

FIG. 69 is a side view showing an electromagnetic coil moving mechanism part.

FIG. 70 is an elevation showing an electromagnetic coil moving mechanism part.

FIG. 71 is an explanatory view showing the formation of an electromagnetic coil moving mechanism part.

FIG. 72 is a view as seen in the direction indicated by the arrow E in FIG. 71.

FIG. 73 is an explanatory view showing an insertable part as vibrated.

FIG. 74 is an explanatory view showing an operation of converting the direction of the tip side of an insertable part.

FIGS. 75 and 76 relate to the 29th embodiment of the present invention.

FIG. 75 is an explanatory view showing a capsule type endoscope as passing through a large intestine.

FIG. 77 is an explanatory view showing an insertable part as being guided.

FIG. 78 is an explanatory view of FIG. 77 as seen from the upper side.

FIGS. 79(a) to 83 relate to the 31st embodiment of the present invention.

FIG. 79(a) and 79(b) are explanatory views showing the whole of an endoscope apparatus.

FIG. 81 is an explanatory view showing an essential part of an endoscope apparatus.

FIGS. 82(A) and (B) are explanatory views respectively showing states of a magnetic force generating part.

FIG. 83 is an explanatory view showing an insertable part as being inserted into a large intestine.

DETAILED DESCRIPTION OF THE PREFERRED EMBODIMENTS

Figure 3A:
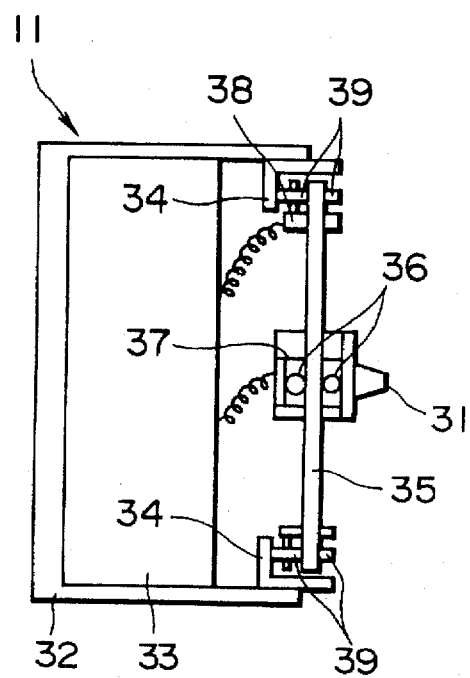
FIG. 3(A) is a side view of a magnetic force generating apparatus.
Figure 3B:
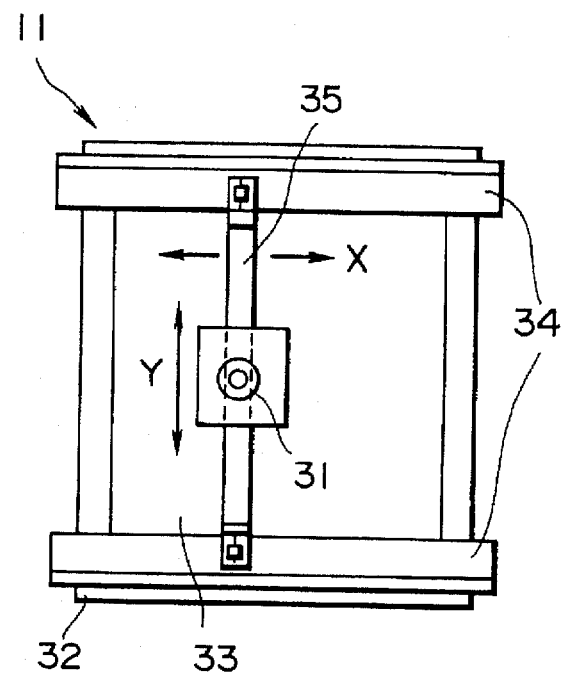
FIG. 3(B) is a plan view of the magnetic force generating apparatus.

FIGS. 1(a) to 4 show the first embodiment of the present invention.

As shown in FIG. 1(a), an endoscope apparatus 1 of this embodiment comprises an endoscope 2 which is a fiberscope, a light source apparatus 3 for feeding an illulminating light to this endoscope 2, a TV camera 5 fitted to an eyepiece part 4 of said endoscope 2, a camera controlling unit (mentioned as a CCU hereinafter) 6 processing a signal for this TV camera 5, a TV monitor 7 inputting a video signal output from this CCU 6 and displaying an inspected object image, a magnetic force generating apparatus 11 arranged below a bed 10 on which is placed a patient 9 into whom is inserted an insertable part 8 of said endoscope and a controlling apparatus 12 to which is connected this magnetic force generating apparatus. A guiding means is formed of said magnetic force generating apparatus 11 and controlling apparatus 12.

The above mentioned endoscope 2 has a flexible elongate insertable part 8, a thick operating part 13 is provided at the rear end of this insertable part 8 and an eyepiece part 4 is provided in the top part (rear end part) of this operating part 13. A light guide cable 14 is extended from the side part of this operating part 13 and is provided at the tip with a connector 14a to be removably connected to said light source apparatus 3.

As shown in FIG. 2, said insertable part 8 has in the tip part 8a a rigid tip forming part 19 as a guided part and is provided in the rear of this tip forming part 19 with a bendable part 21. An illuminating window and observing window ae provided on the tip surface of said tip forming part 19. A light distributing lens 15 is provided inside said illuminating window. A light guide 16 is provided at the rear end of this light distributing lens 15, is inserted through said insertable part 8 and light guide cable 14 and is connected at the entrance end to said connector 14a. An illuminating light emitted from a lamp 17 within said light source apparatus 3 will be condensed by a condenser lens 18, will enter said light guide 16 at the entrance end, will pass through said light guide 16 and light distributing lens 15 and will be emitted forward from said illuminating window.

Also, an objective lens 24 is provided inside said observing window and the tip surface of an image guide 25 is arranged in the image forming position of this objective lens 24. This image guide 25 is inserted through said insertable part 8 and operating part 13 and is opposed on the rear end surface to an eyepiece lens 26 within the eyepiece part 4 as shown in FIG. 1(b). An optical image of an inspected object illuminated by said illuminating light will be formed on the tip surface of the image guide 25 by the objective lens 2, will be transmitted to the eyepiece part 4 by this image guide 25 and will be magnified and observed through the eyepiece lens 26 of this eyepiece part 4.

As shown in FIG. 1(b), the TV camera 5 fitted to said eyepiece part 4 is provided with an image forming lens 27 opposed to said eyepiece lens 26 and a solid state imaging device, for example, a CCD 28 aranged in the image forming position of this image forming lens 27. The optical image transmitted to said eyepiece part 4 will be formed on the CCD 28 by said image forming lens 27 and will be photo-electrically converted by this CCD 28. The output signal of this CCD 28 will be input into the CCU 6 and will be processed to be converted to a video signal and the object image will be displayed in a TV monitor 7 into which this video signal will be input.

As shown in FIG. 2, a hood 20 can be fitted to said tip forming part 19 which is formed of a permanent magnet as a magnetic field generating means. The permanent magnet may preferably be such rare earth magnet high in the magnetic force as samarium cobalt ($SmCo_5$ or $Sm_2Co_{17}$) or a neodymium-iron-boron series (NdFeB).

The bendable part 21 adjacent to said tip part 19 is formed of articulation frames 22 connected rotatably with each other so as to be bendable vertically and horizontally and to be bendable in any direction by rotating a bending knob not illustrated provided on the operating part 13 and is coated with a flexible sheath.

By the way, at least the tip forming part 19 and such other component parts than the hood 20 as, for example, the articulation frames 22 in the insertable part 8 are formed of a non-magnetic material (aluminum, copper alloy or the like) not attracted by the magnetic force.

FIG. 1(a) shows the above mentioned endoscope 2 as being inserted into a large intestine of the patient 9.

The bed 10 on which said patient is horizontally mounted is formed of such non-magnetic material as wood.

The magnetic force generating apparatus 11 arranged below this bed 10 is provided with a magnetic force generating part 31 as a guiding part movable two-dimensionally in a horizontal plane.

The formation of this magnetic force generating apparatus 11 is shown in FIGS. 3(A) and (B).

A power source 33 for generating a magnetic force and for moving a magnetic force generating part 31 is housed in the bottom within a chassis 32 opening on the upper side.

Paired guide rails 34 are fitted to the parallelly opposed upper end sides of said chassis 32. a second guide rail 35 is provided in a direction (indicated by Y) intersecting at right angles with the lengthwise direction (indicated by X) of said guide rails 34 between these guide rails 34 and the magnetic force generating part 31 made of an electromagnet is fitted on this guide rail 35 so as to be movable in the lengthwise direction Y of said guide rail 35.

Said magnetic force generating part 31 is fitted to the guide rail 35 through rotors 36 rotated by a motor 37.

Said guide rail 35 is mounted at one end on the guide rail 34 through a motor 38 and rotors 39 rotated by this motor 38.

Therefore, when the motor 38 is rotated, the rotors 39 will be rotated to move the guide rail 35 in the lengthwise direction X of the guide rails 34.

By the way, the motors 37 and 38 rotating and driving respectively said rotors 36 and 39 may preferably be ultrasonic motors not influenced by the magnetic force. Said motors 37 and 38 can be rotated (normally or reversely or stopped) by a control part 12 connected through a cable 40. There is formed a driving means whereby the magnetic force generating part 31 can be thus moved and set in any position in a horizontal plane.

The operation of the thus formed first embodiment shall be explained in the following with reference to FIG. 4.

Figure 4:
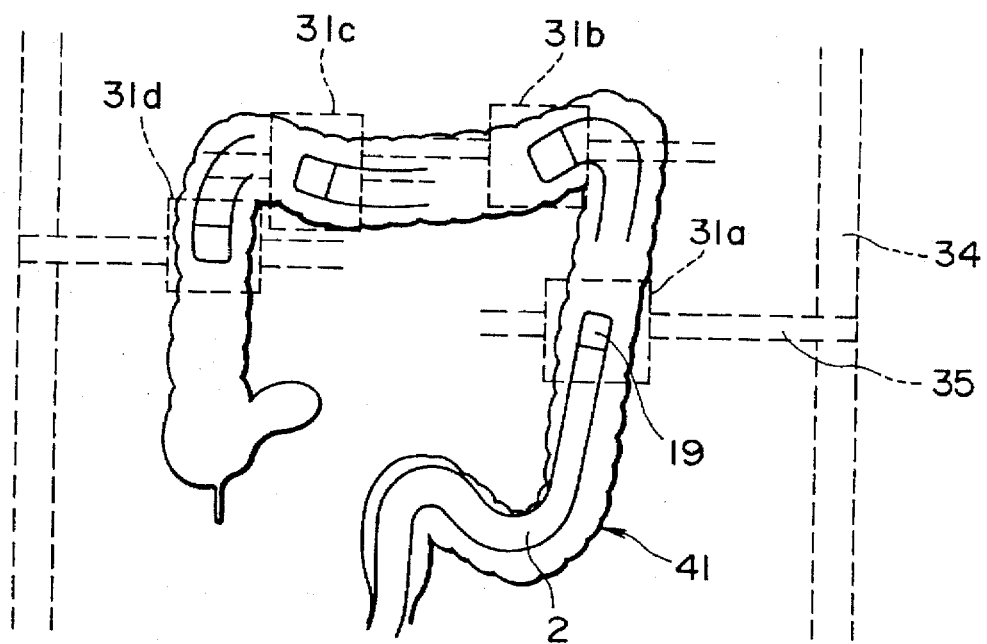

As shown in FIG. 4, when the endoscope 2 is pushed into a large intestine and then an electric current is passed to the magnetic force generating part 31 made of an electromagnet, a magnetic force acting between this magnetic force generating part 31 and tip part body 19 (or hood 21) will be generated. In case the horizontal position of the magnetic force generating part 31 is moved while observing the endoscope image in the TV monitor 7, if the horizontal position of the magnetic force generating part 31 is sequentially moved along the bent tube cavity of the large intestine 41 as shown by the dotted lines 31a, 31b, 31c and 31d, the tip part body 19 (or the hood 20) will be attracted by the magnetic force and will be therefore moved to trace the moving course of the magnetic force generating part 31 so that the tip part 89 may be inseted into the deep side of the large intestine 41.

By rotating the motors 37 and 38, the magnetic force generating part 31 can be moved in the lengthwise direction Y of the guide rail 35, the guide rail 35 can be moved in the lengthwise direction X of the guide rails 34 and therefore the magnetic force generating part 31 can be moved to any position in the horizontal plane. In fact, the tip part 8a will be advanced while being attracted by the magnetic force by the magnetic force generating part 31 from below the patient 9 and will be therefore able to be slid while being slid on the large intestine wall surface (the large intestine wall surface between the tip part 8a and magnetic force generating part 31).

According to the first embodiment, the tip part can be easily inserted into such bent part as in the large intestine 41.

As the tip part 8a is guided by two-dimensionally moving the magnetic force generating part 31 by using the driving means, the guidance controllability will be higher than in the case of manually guiding.

By the way, in this first embodiment, in response to the body structure of the patient 9, the form of the tube cavity of the large intestine 41 which will be standard in the case of that body structure may be displayed in the TV monitor 7 or on any other monitor picture and the position in the horizontal plane of the magnetic force generating part 31 may be displayed as superimposed on this picture so that, in case the magnetic force generating part 31 is moved, the position in the horizontal plane of the magnetic force generating part 31 corresponding to the position of the tube cavity may be easy to find and the tip part may be easy to insert.

In case the magnetic force generating part 31 is moved, the form of the tube cavity and the relative position with the magnetic force generating part 31 of the large intestine 41 may be simultaneously corrected from its locus.

By the way, the horizontal position of the magnetic force generating part 31 can be detected, for example, with encoders fitted to the motors 37 and 38.

The above mentioned magnetic force generating part 31 is made movable to the position of pulling the tip part 8a as sliding on the wall surface and can be therefore formed of a small electromagnet or the like.

Further, on the endoscope side, when the tip part body 19 or the hood 20 fitted to this tip part body 19 is formed of a permanent magnet or ferromagnetic substance, the insertable part 8 need not be made substantially large in the outside diameter and the pain given to the patient will be able to be reduced.

Figure 5:
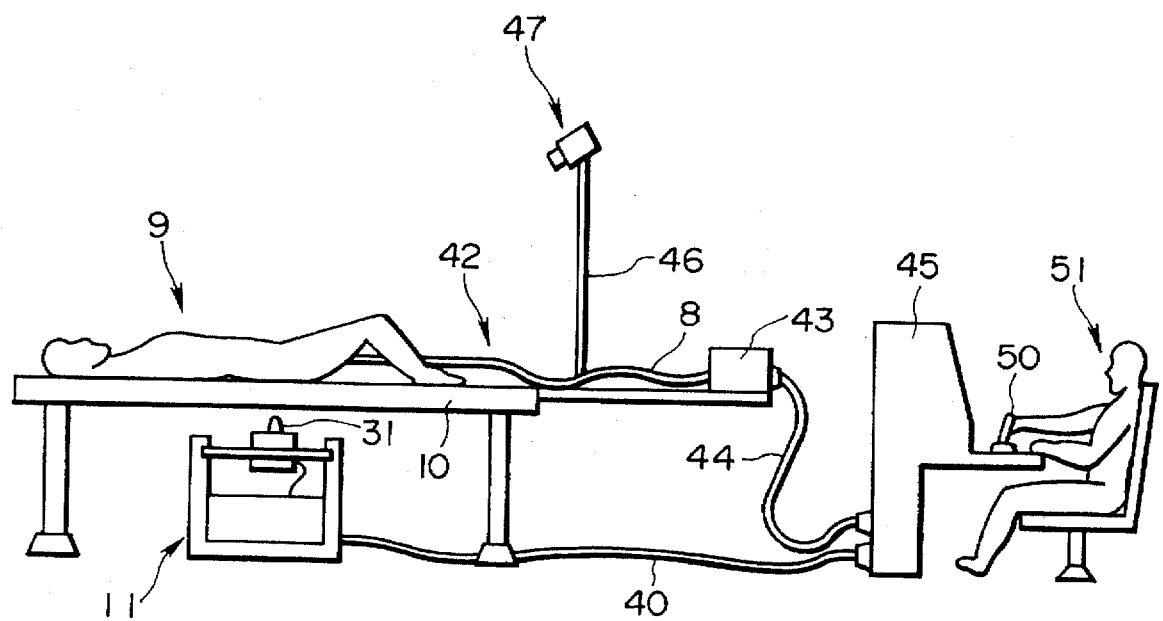
FIGS. 5 to 6 relate to the second embodiment of the present invention.

FIG. 5 shows the second embodiment of the present invention.

In this second embodiment, the insertable part 8 of an endoscope 42 is connected at the rear end to an observing unit 43 having a TV camera built-in and a cable 44 of this observing unit 43 is connected together with a cable 40 of the magnetic force generating apparatus 11 to an operating part 45 having a light source apparatus and a CCU for processing a signal built-in.

Also, a patient monitoring TV camera 47 is fitted to the bed 10 through a camera fitting member 46 and a signal line of this TV camera 47 is also connected to the operating part 45.

Figure 6:
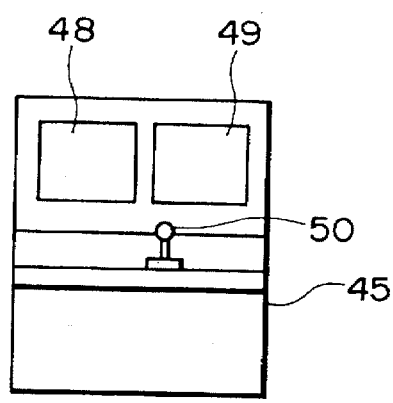

As shown in FIG. 6, an endoscope image monitor 48 displaying an endoscope image by the TV camera within the observing unit 43 and a patient image monitor 49 displaying a patient image by the monitoring TV camera 47 are provided on the panel part of the operating part 45. A joystick 50 for moving and operating the magnetic force generating part 31 is provided on an operating stand of the operating part 45 so that the operator 51 may move the position of the magnetic force generating part 31 while seeing the endoscope image.

The others are of substantially the same formation as in the first embodiment.

The operation of this second embodiment is substantially the same as in the first embodiment but the operator 51 can move the magnetic force generating part 31 while observing the manner of the patient 9 as well as the endoscope image and can advance the endoscope 42 into the large intestine so that the manner of the pain of the patient 9 may be known and the operator 51 may insert the endoscope 42 safely, remotely and easily.

FIG. 7 shows the third embodiment of the present invention.

In this embodiment, instead of the magnetic force generating apparatus 11 in the second embodiment, as shown in FIG. 7, an annular magnetic force generating apparatus 61 surrounding the patient 9 with the patient 9 as a center is arranged and is movable in the direction vertical to the annular surface, that is, in the lengthwise direction of the bed 10 on which the patient 9 is mounted on a rail 62.

In the operating part 45 of this embodiment, the monitor adjacent to the endoscope image monitor 48 is to be used as a patient data displaying part 63 inputting and outputting such various informations as the history of the patient and received results and displaying the results.

Further, in this operating part 45, instead of the joystick, a guiding switch 64 is provided to indicate the position movement of the magnetic force generating apparatus 61.

Figure 9A:
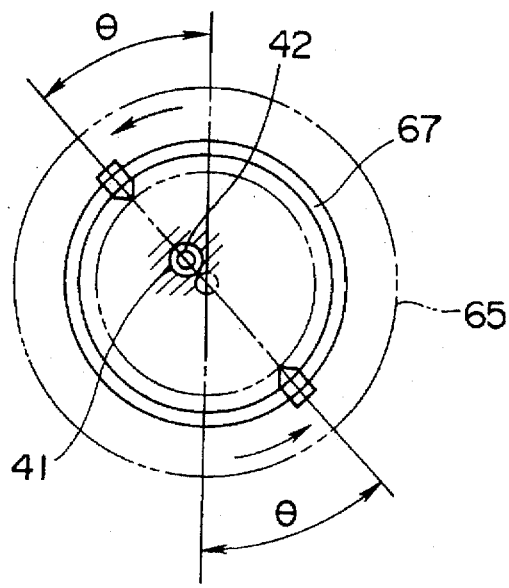
FIG. 9(A) is an explanatory view showing the magnetic force generating apparatus of FIG. 8(A) in another state.

FIGS. 8 and 9 are internal formation principle views of the magnetic force generating apparatus 61.

As shown in FIGS. 8(A) and (B), within the annular part 65 of the magnetic force generating apparatus 61, magnetic force generating parts 66A and 66B made of electromagnets are respectively rotatably fitted to a guide ring 67 as guiding parts in two places opposed to each other, are to be rotatable as opposed by 180 degrees to each other by such known means as a motor so as to be movable two-dimensionally and are shown in FIG. 9 as rotated by an angle θ from the state, for example, in FIG. 8.

The operation of this third embodiment shall be explained in the following.

The operator inserts the endoscope 42 into the large intestine 41 through the anus by a pushing operation. Then, the magnetic force generating parts 66A and 66B of the magnetic force generating apparatus 61 are driven and the tip part 8a of the endoscope is attracted the same as in the first embodiment by the magnetic forces and is inserted into the deep side of the large intestine 41.

Figure 9B:
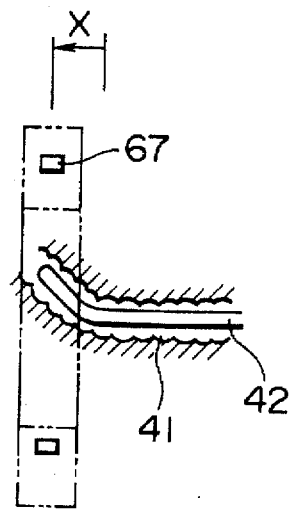
FIG. 9(B) is an explanatory view showing a sectioned view of FIG. 9(A).

In the state shown, for example, in FIG. 8(A), the large intestine 41 is in the center of the annule part 65 and the tip part 8a of the endoscope is inside the large intestine 41. A sectioned view on line A–A' in FIG. 8(A) is shown in FIG. 8(B) in which the left side shows the deep side of the large intestine 41. In order to further insert the tip part 8a of the endoscope into the deep side, as the tube cavity of the large intestine is bent upward in the sectioned view on line A–A' in FIG. 8(A), it is necessary to attract the tip part 8a in this bending direction. Therefore, the annular magnetic force generating apparatus 61 is moved, for example, by x mm. to the left side in FIG. 8(B) or in the direction of the rail 62 in FIG. 7 and the magnetic force generating parts 66A and 66B are rotated by θ degrees so as to be in the state shown in FIG. 9(A). Further, at this time, the magnetic force of the magnetic force generating part 66A is elevated. Then, the permanent magnet or ferromagnetic substance part of the endoscope tip part will be strongly attracted and moved to the magnetic force generating part 66A side and will move substantially by x mm. along the bent tube cavity so as to be as shown in FIG. 9(B).

Thus, by controlling the magnetic force generating apparatus 61 in the lengthwise direction of the patient 9 (the lengthwise direction of the bed), the rotation and movement of the magnetic force generating parts 66A and 66B and further the strength of the magnetic force, the endoscope can be easily inserted even into the complicated large intestine tube cavity.

The other formations, operations and effects are the same as in the first embodiment.

FIGS. 10 to 13 show the fourth embodiment of the present invention.

Figure 10:
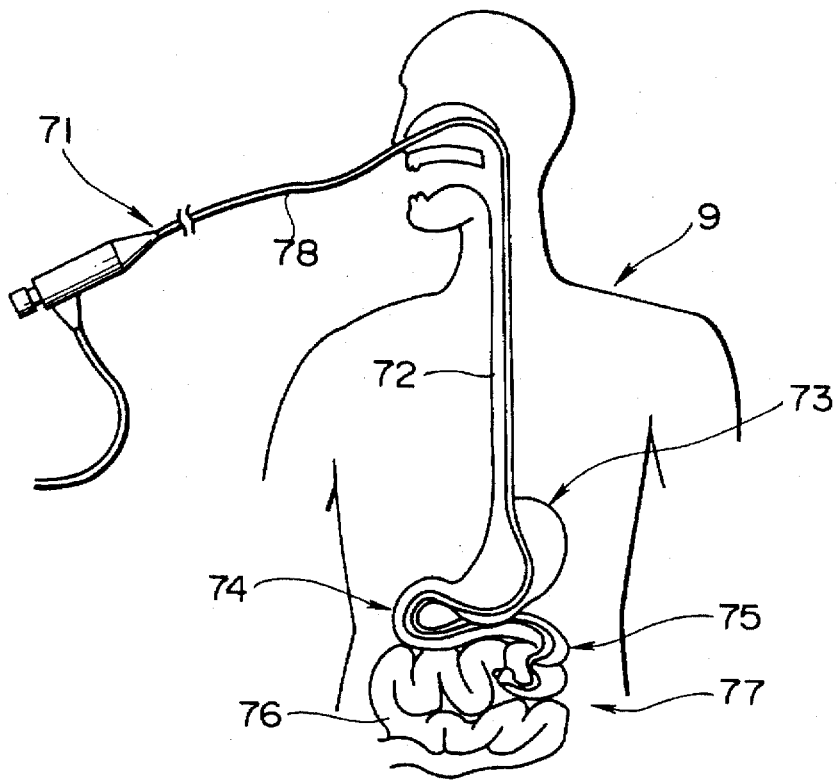
FIGS. 10 to 13 relate to the fourth embodiment of the present invention.

FIG. 10 shows a small intestine endoscope 71 in this embodiment. In FIG. 10 is shown the endoscope 71 as inserted into the nasal cavity, gullet 72, stomach 73, duodenum 74, jejunum 75, ileum 75 and small intestine 77.

Figure 11:
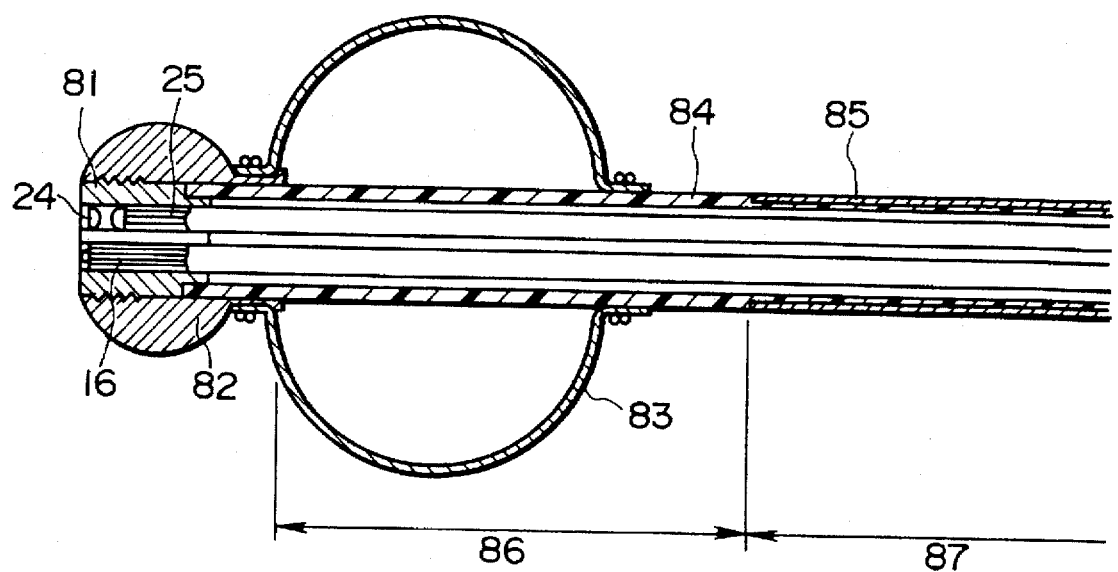

In this small intestine endoscope 71, the tip side structure of the insertable part 78 is as shown in FIG. 11.

A hood 82 is screwed to a tip part 81 of an insertable part 78 and a balloon 83 is connected to the hood 82 in the rear and is connected and fixed at the other end to a first sheath 84 respectively by winding threads. The same as in an ordinary endoscope, there are provided an objective lens 24, image guide fiber 25 and light guide fiber 16. The sheath 84 is coated in the rear with a second sheath 85. The hood 82 is formed of the already described permanent magnet or ferromagnetic substance. The insertable part 78 has a flexibility in two steps of a very soft part 86 and a soft part 87 following it. Thus, the very soft part 86 is formed of the sheath 84 made of a low hardness, that is, soft material and the soft part 87 is formed of the sheath 85 made of a high hardness, that is, hard material.

The operation of the fourth embodiment shall be explained in the following.

This endoscope 71 is called a sonde type small intestine fiber scope. As in FIG.. 10, the endoscope 71 inserted through the nasal cavity is expanded by filling the balloon 83 with water and is inserted by the vermicular motion of the patient 9 with the balloon as a weight.

Figure 12:
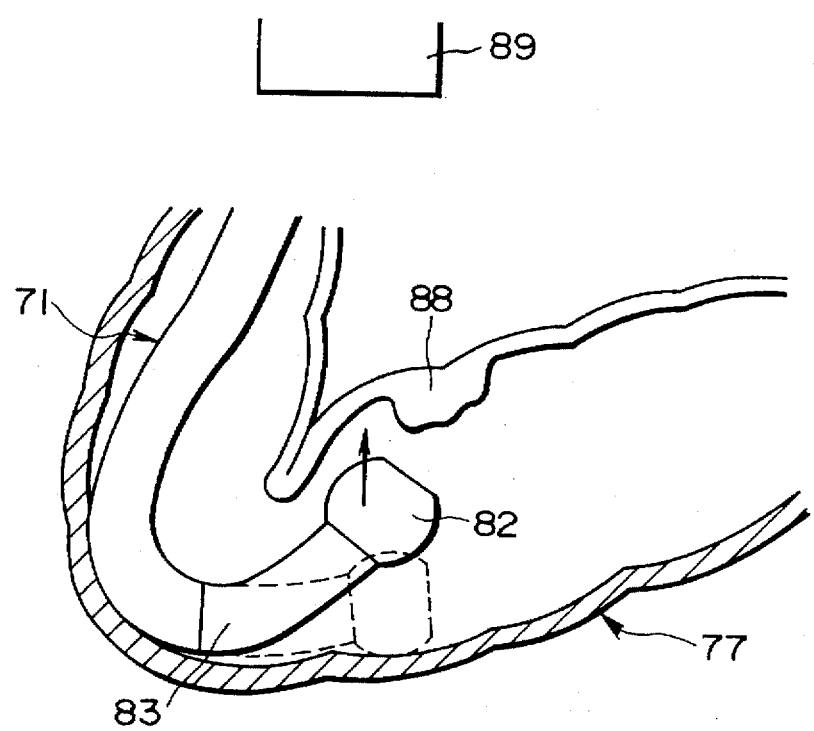

As shown in FIG. 12, in case the endoscope has come to an affected part 83 within the small intestine 77, the balloon 83 of the endoscope 71 will be contracted, the magnetic force generating part (represented by the reference numeral 89) in the first, second and third embodiments will be driven and the hood 82 of the endoscope 71 will be attracted by the magnetic force from outside the body so that the affected part 83 may be seen in elevation and may be accurately diagnosed and further the tissue may be collected by using a vivisecting forceps or the like.

Figure 13:
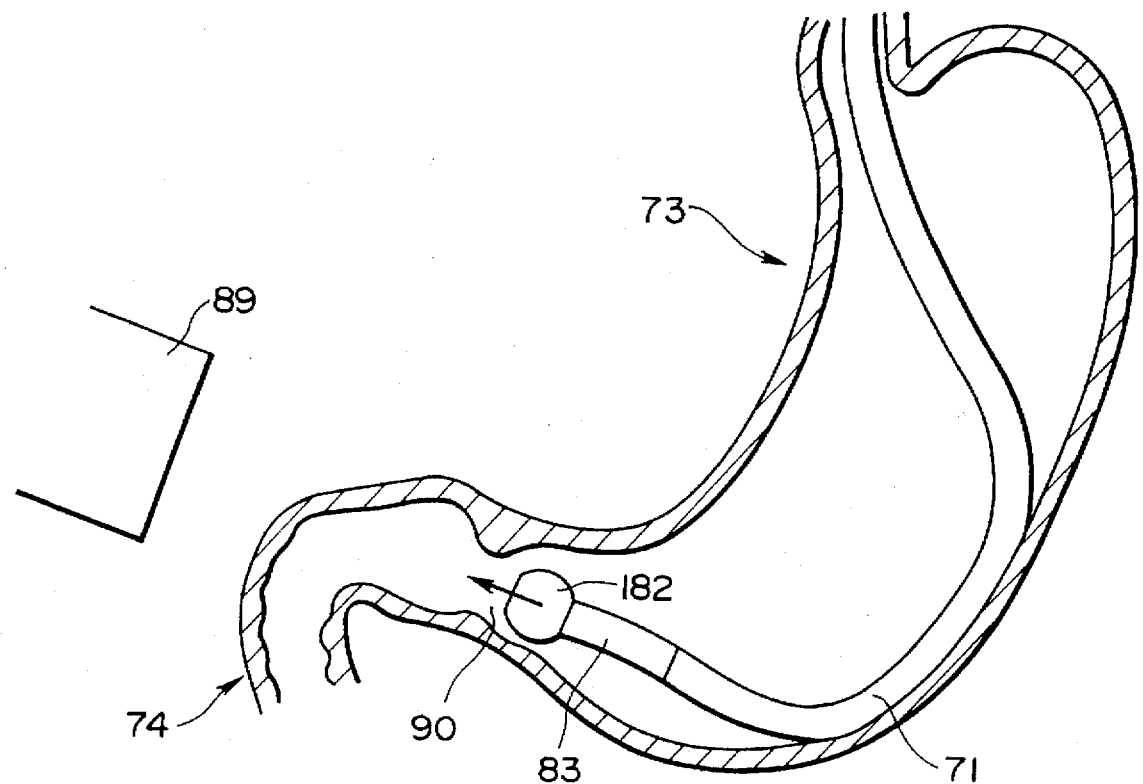

Also, as shown in FIG. 13, in case the endoscope 71 is to be passed through the pyloric region 90, in the same manner, the magnetic force generating part 89 is driven to make the passage easy.

By the way, as understood from FIG. 12, as the very soft part 86 is provided, in case the hood 82 is attracted by the magnetic force, the insertable part will be able to be easily bent in a desired direction without making the reaction large (as the soft part 87 is harder, as in FIG. 12, the very soft part 87 will be able to be bent and a bend small in the bending length and radius will be able to be realized).

The other formations, operations and effects are the same as in the first to third embodiments.

Figure 14:
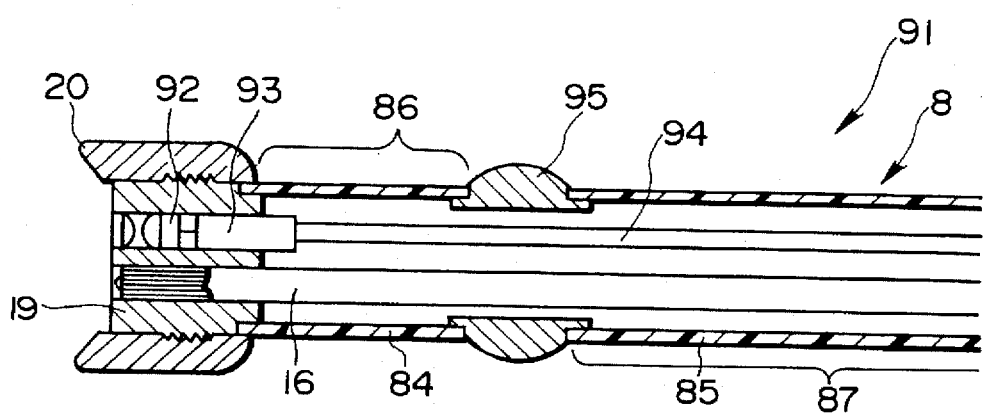

FIGS. 14 and 15 show the fifth embodiment of the present invention.

FIG. 14 shows the tip side formation of an endoscope of this embodiment.

The endoscope 91 of this embodiment is an electronic endoscope and has a light guide 16, objective lens 24 and hood 20 the same as in the endoscope 2 shown in FIG. 2 but a solid state imaging device (abbreviated as an SID hereinafter) 92 is arranged in the focal plane of the objective lens 24 and a drive circuit 93 is driven by this SID.

This drive circuit 93 is connected to the CCU, for example, in FIG. 1 through a cable 94 inserted through the insertable part 8.

In this insertable part 8, the part adjacent to the tip part 19 is formed of a very soft part 86 formed of a sheath 84 of a soft material, a rear magnetic body 95 is formed at the rear end of this very soft part 86 and the front side very soft part 86 and a rear side soft part 87 formed of a sheath 85 of a material harder than said sheath 84 are connected with each other by said rear magnetic body 95.

Said hood 20 and rear magnetic body 95 are formed of the above described permanent magnet or ferromagnetic substance and are reverse to each other in the polarity of the outer peripheral part. For example, the outer periphery of the hood 20 is made an N pole and the outer periphery of the rear magnetic body 95 is made an S pole.

The other formations are substantially the same as in the first embodiment or other embodiments.

The operation of this fifth embodiment shall be explained in the following.

As shown in FIG. 15, the endoscope 91 is inserted into the large intestine 41 and is advanced by a magnetic force by driving the magnetic force generating part 39 the same as in the other embodiments.

In this case, when the magnetic force generating part 89 is made an N pole, a reaction will act on the hood 20 and an attraction will act on the rear magnetic body 95 so that the tip part 19 may be positioned in the center within the tube cavity, may be easy to see in elevation, may float even somewhat on the tip side and may be easy to advance without catching on the tube wall.

By the way, in order to prevent the influence of the magnetic noise on the SID 92, a magnetic shielding material may be provided on the periphery of the SID 92 within the endoscope 91.

The other operations and effects are the same as in the fourth embodiment.

FIGS. 16 to 19 show the sixth embodiment of the present invention.

As shown in FIG. 16, an endoscope 101 of this embodiment is provided with knobs 102a, 102b, . . . at regular intervals on the soft part on the rear side of the tip part 19 to form an insertable part.

That is to say, the soft part 104a following the tip part 19 is connected with its rear soft part 104b through the knob 102a at a fixed distance, this soft part 104b is connected with its rear soft part 104c through the knob 102b at a fixed distance and so on so that the insertable part 19 may be divided into many soft parts 104a, 104b, . . . by the knobs 102a, 102b, . . .

Said tip part 19 and knobs 102a, 102b, . . . are formed of a permanent magnet or ferromagnetic subsance as already described. Also, a plurality of magnetic force generating parts 89a, 89b, . . . are provided outside the body in response.

Figure 17:
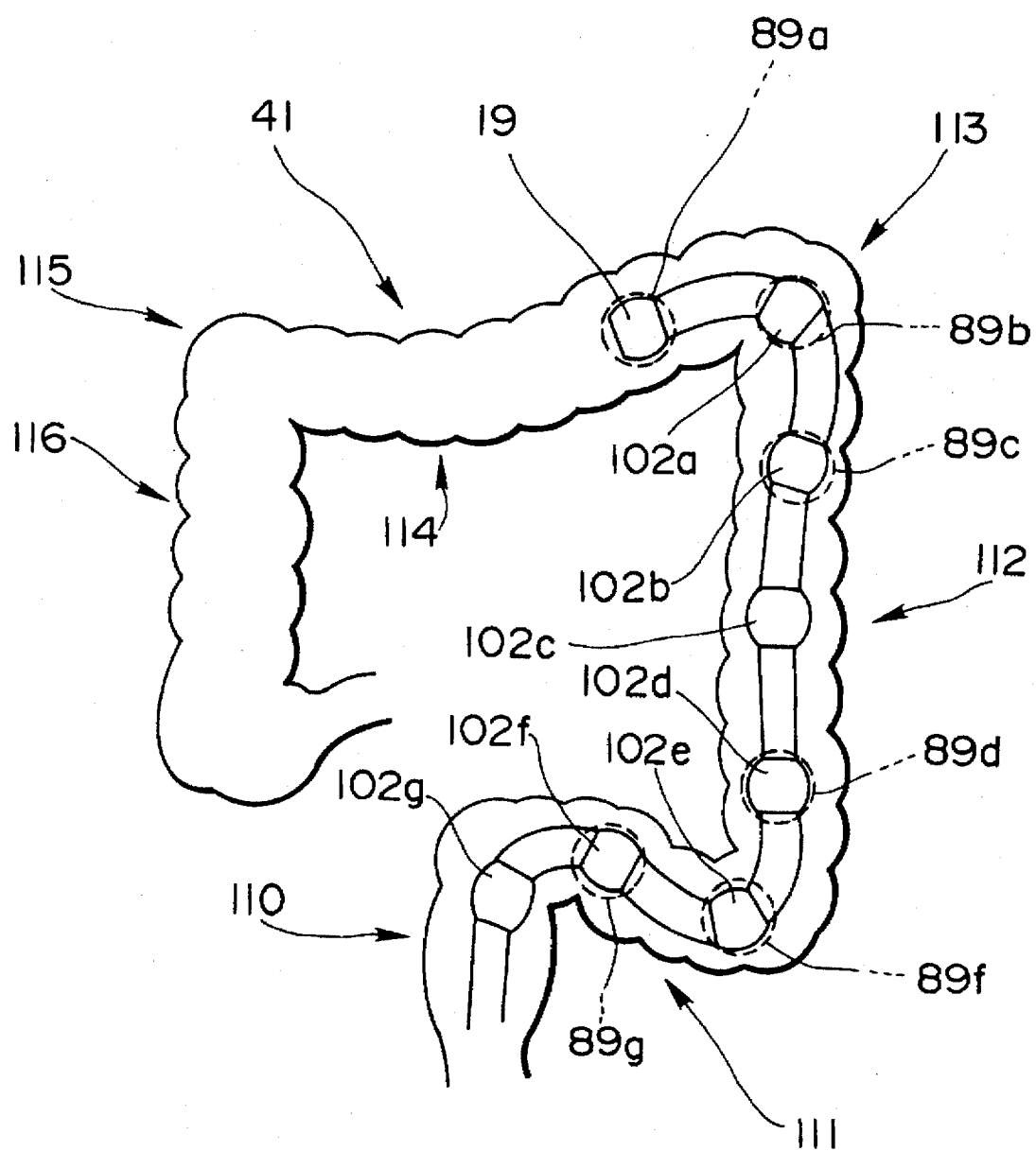

FIG. 17 shows said endoscope 101 as inserted into the large intestine 41. The endoscope 101 is inserted into the rectum 110, S colon 111, descendent colon 112, left colon bend 113, lateral colon 114, right colon bend 115 and ascendent colon 116. The knots 102a, 102b, 102c, 102d, 102e, 102f, 102g, . . . are provided following the tip part 19. The magnetic force generating parts 89a, 89b, 89c, 89d, 89e, 89f, 89g, . . . (represented by 89i) are arranged outside the body in response to said knobs.

Figure 18:
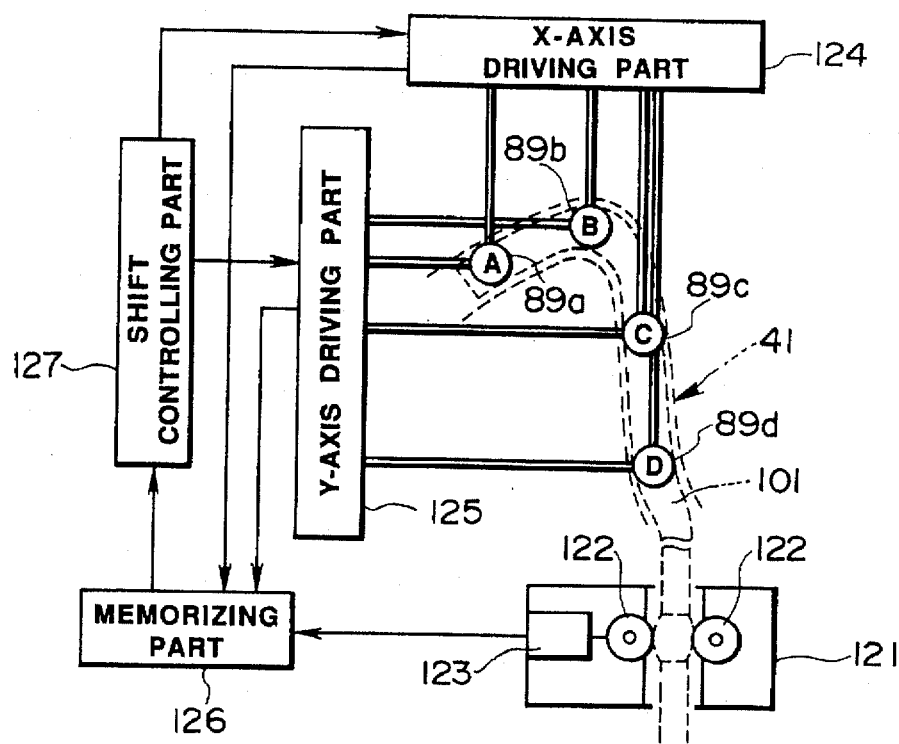
Figure 19:
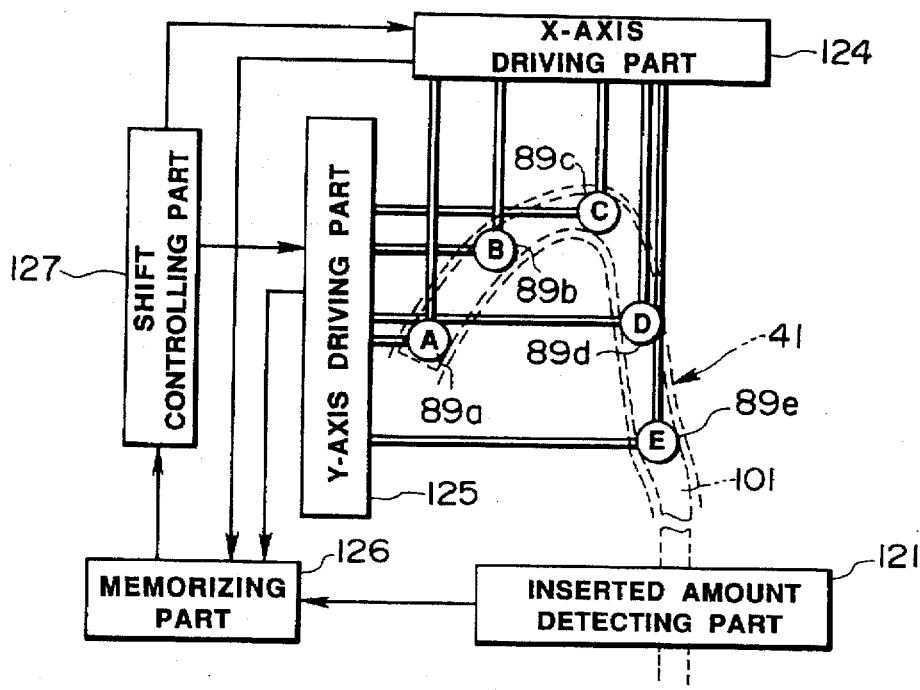

FIGS. 18 and 19 show the driving mechanism of the magnetic force generating parts 89i outside the body.

An inserted amount detecting part 121 detecting the inserted amount of the endoscope 101 outside the body is provided and the rotated amount of rollers 122 is detected by an encoder 123. An X-axis driving part 124 and Y-axis driving part 125 for moving the positions of the respective magnetic force generating parts 89i are provided and the respective magnetic force generating parts 89i are independently driven. The positions (X and Y) of the respective magnetic force generating parts 89i are input into the memorizing part 126. The signal of the inserted amount detecting part 121 is also input into the memorizing part 126. The operating signal of this memorizing part 126 is input into a shift controlling part 127 of this memorizing part 126 and is fed back to the X-axis driving part 124 and Y-axis driving part 125.

The operation of this embodiment shall be explained in the following.

As in FIG. 18, the positions A, B, C, D, . . . of the respective magnetic force generating parts 89a, 89b, 89c, 89d, . . . are memorized by the coordinates (X and Y) corresponding to the inserted amounts. When the insertion is continued, as in FIG. 19, B, C, D and E will be positioned in the positions of A, B, C and D. Thus, by the inserted amount detecting part 121, it can be detected that B in FIG. 19 comes to A in FIG. 19. Thereby, by operating the X-axis and Y-axis driving parts 124 and 125, B, C, D and E in FIG. 19 are moved to the positions of A, B, C and D in FIG. 18. That is to say, while combining the inserted amount and the moved amount by the X-axis and Y-axis driving parts 124 and 125, the endoscope 101 is moved by a shift controlling part 127.

By this operation, as in FIG. 17, the tip part 19 and respective knobs 102a, 102b, . . . attracted by the magnetic force are moved and can be inserted along the tube path shape of the large intestine 41.

By the way, the magnetic force generating part 89a corresponding to the tip part 19 is manually operated in the driving position while the operator is observing the endoscope image.

In this embodiment, as the rear side of the tip part 19 is inserted and moved so as to follow the part before that part, even if the inserted amount is deep, the influence of the friction with the tube wall will be little, they will be able to be inserted with the sense of merely inserting only the tip part 19, the inserting operation by the operator will be easy and the pain of the patient will be able to be made small.

By the way, the tip part 19 inserting process may be recorded by a recording means so that, in the case of the next insertion, the recorded inserting process may be made a guide. This is effective particularly to the same patient and to the case that the body form is similar.

The other formations, operations and effects are the same as in the first embodiment.

By the way, a different embodiment can be formed by partly combining the above described embodiments.

The present invention is not limited to the above described embodiments.

For example:

(1) The magnetic force generating means arranged outside the body may be a permanent magnet. In such case, the magnetic force can be controlled by varying the distance for the endoscope.

(2) The electromagnetic force of the magnetic force generating means may be of a super conductive magnet as well as an ordinary conductive magnet.

(3) Instead of a permanent magnet or ferromagnetic substance, an electromagnet may be provided as a guided part provided in the endoscope itself. In case the guided part is a permanent magnet or electromagnet, the magnetic force generating means outside the body may be of a ferromagnetic substance.

(4) The other applications than to the endoscopes for the large and small intestines shown in the respective embodiments can be to:

Endoscopes for veins;
Catheters for digesting tubes and for veins; Capsule type endoscopes, capsule type intestinal liquid collecting apparatus and capsule type medicine administering apparatus.

As described above, according to the first to sixth embodiments, an endoscope provided in the tip part with a permanent magnet or ferromagnetic substance and a magnetic force generating means movable at least two-dimensionally around such inserted object as a patient are provided so that the endoscope may be moved by this magnetic force generating means. Therefore, the endoscope can be smoothly inserted by the magnetic force without being substantially made large in the diameter and can be moved by sliding on the tube wall and the magnetic force generating means can be also made small. As the guiding part is moved by using a driving means, the guidance controllability is high.

FIGS. 20(a) to 22 show the seventh embodiment of the present invention.

Figures 20A, 20B:
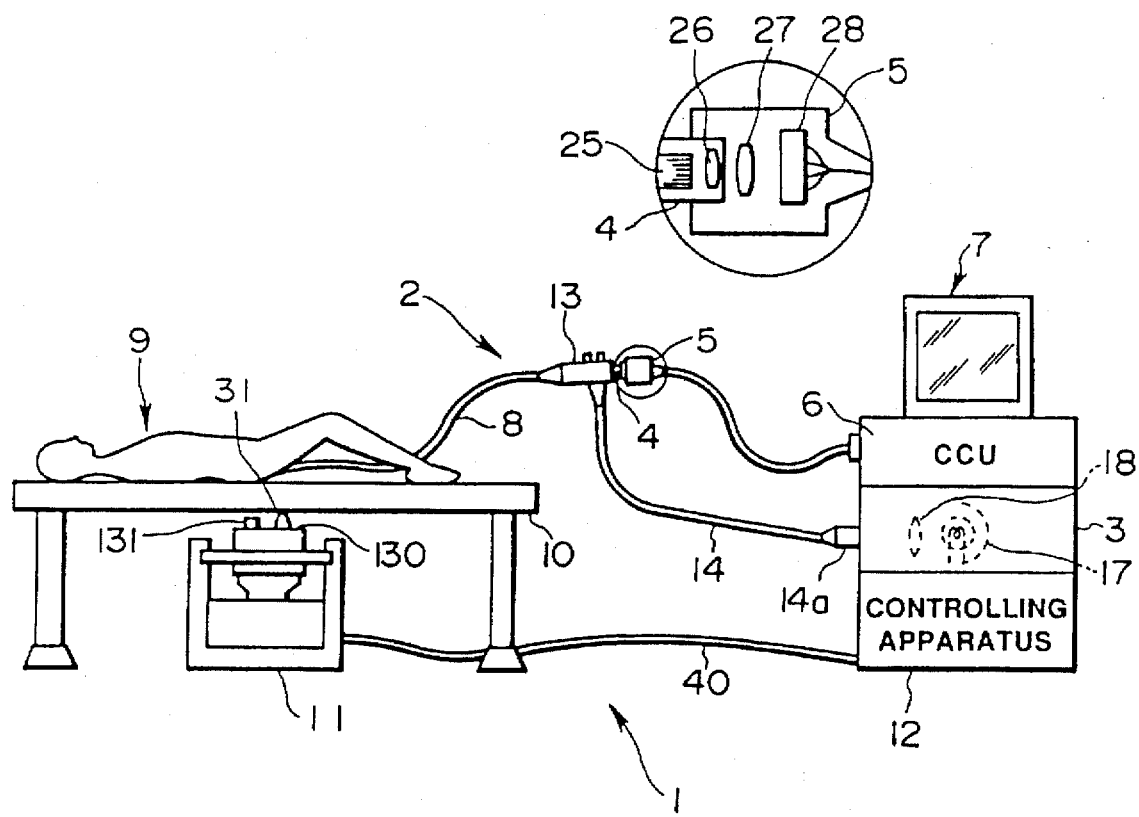

As shown in FIG. 20(a), an endoscope apparatus 1 of this embodiment comprises the same as in the first embodiment an endoscope 2 which is a fiberscope, a light source apparatus 3 for feeding an illuminating light to this endoscope 2, a TV camera 5 to be fitted to an eyepiece part 4 of said endoscope 2, a CCU 6 processing a signal for this TV camera 5, a TV monitor 7 inputting a video signal output from this CCU 6 and displaying an object image, a magnetic force generating apparatus 11 arranged below a bed 10 on which is placed a patient 9 into whom the insertable part 8 of said endoscope 2 is to be inserted and a controlling apparatus 12 to which is connected this magnetic force generating apparatus 11. A guiding means is formed of said magnetic force generating apparatus 11 and controlling apparatus 12.

The formations and operations of said endoscope 2, light source apparatus 3, TV camera 5, CCU 6 and TV monitor 7 are the same as in the first embodiment.

The magnetic force generating apparatus 11 in this embodiment is provided with a magnetic force generating part 31 movable in a horizontal plane and a hall sensor 131.

Figure 21A:
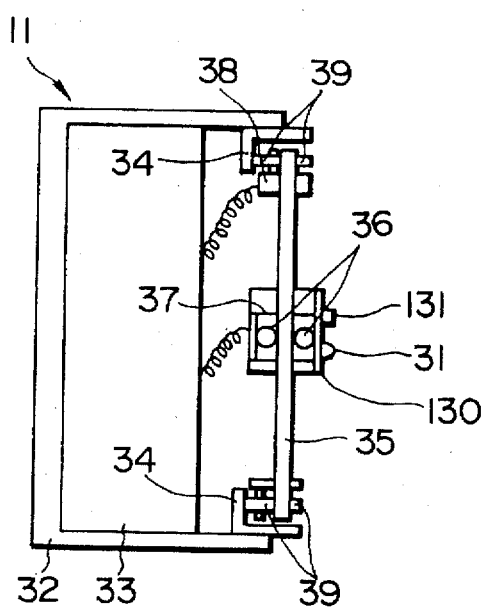
FIG. 21(A) is a side view of a magnetic force generating apparatus.
Figure 21B:
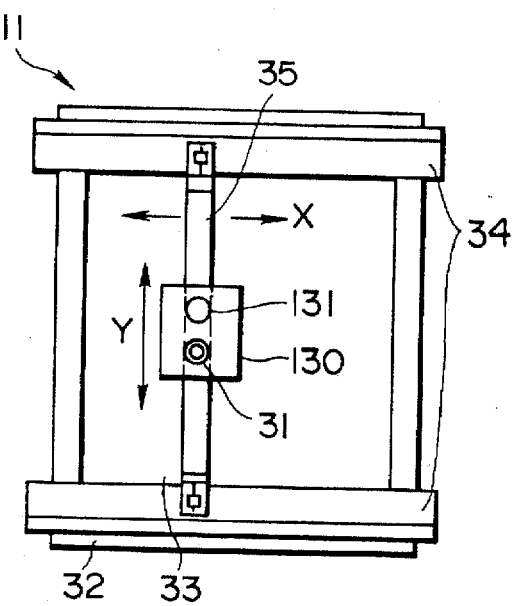
FIG. 21(B) is a plan view of the magnetic force generating apparatus.

The formation of this magnetic force generating apparatus 11 shall be explained with reference to FIGS. 21(A) and (B).

A power source 33 for generating a magnetic force from the magnetic force generating part 11, for detecting a magnetic field in the hall sensor 131 and for moving the magnetic force generating part 31 and hall sensor 131 is housed in the bottom within a chassis 32 opened on the upper side.

Paired guide rails 34 are fitted to the parallelly opposed upper end sides of said chassis 32. A second guide rail 35 is provided in the direction (represented by Y) intersecting at right angles with the lengthwise direction (represented by X) of said guide rails 34 between these guide rails 34. A stage 130 is fitted movably in the lengthwise direction Y of the guide rail 35 on this guide rail 35. On this stage 130 are fitted the magnetic force generating part 31 made of an electromagnet and the hall sensor 131 using a hall device.

Said stage 130 is fitted to the guide rail 35 through rotors 36 rotated by a motor 37. Said guide rail 35 is mounted at one end on the guide rail 34 through a motor 38 and rotors 39 rotated by this motor 38 so that, when the motor 38 is rotated, the rotors 39 may be rotated to move the guide rail 35 in the lengthwise direction X of the guide rails 34.

By the way, the motors 37 and 38 rotating and driving respectively said rotors 36 and 39 may preferably be ultrasonic motors not influenced by the magnetic force. Said motors 37 and 38 are controlled to rotate (normally or reversely) and stop by the controlling apparatus 12 connected through a cable 40 so that the magnetic force generating part 31 and hall sensor 131 may be moved and set in any position in the horizontal plane.

Figure 22:
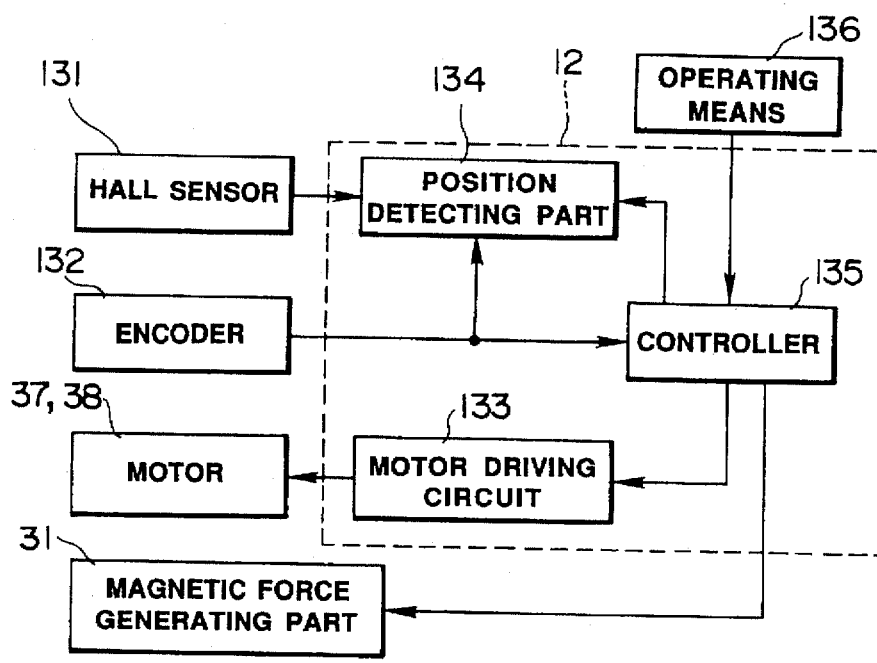

The formation of said controlling apparatus 12 shall be explained with reference to FIG. 22.

The controlling apparatus 12 comprises a motor driving circuit 133 driving said motors 37 and 38, a position detecting part 134 inputting the output of said hall sensor 131 and the output of an encoder 132 fitted to said motors 27 and 28 and detecting the position of the tip forming part 19 and a controller 135 inputting the signal from an operating means 136 indicating the positions of the magnentic force generating part 31 and hall sensor 131 and the output of said encoder 132 and controlling said motor driving circuit 133, position detecting part 134 and magnetic force generating part 31. Said controller 135 drives the motors 37 and 38 through the motor driving circuit 133 so that the magnetic force generating part 31 and hall sensor 131 may come to the positions indicated by the operating means 136. The positions of said magnetic force generating part 31 and hall sensor 131 can be determined from the output of the encoder 132. When the position detection of the tip part forming part 19 is instructed by the operating means 136, the controller 135 will control the motor driving circuit 133 to scan the hall sensor 131 in the horizontal plane. Then, the outputs of the hall sensor 131 will be determined in response to the respective positions determined by the output of the encoder 132 in the position detecting part 134 and the position in which the output of this hall sensor 131 is maximum will be determined as the position of the tip forming part 19.

The operation of this embodiment formed as in the above shall be explained in the following.

When the insertable part 8 of the endoscope 2 is first inserted to some extend into such object to be ispected as the large intestine and then the position detection of the tip forming part 19 is instructed by the operating means 136, the controller 35 will control the motor driving circuit 133 so that the hall sensor 131 may be scanned in the horizontal plane. The outputs of the hall sensor 131 in the respective positions will be determined. The position in which the output of this hole sensor is maximum will be determined as the position of tip forming part 19.

After the position of the tip forming part 19 is thus detected, the insertable part 8 will be magnetically guided and will be further inserted into the object. That is to say, when a magnetc field is generated from the magnetic force generating part 31 through the controller 135 by the instruction of the operating means 136, a magnetic force, for example, an attraction is generated between this magnetic force generating part 31 and the tip forming part 19 made of a permanent magnet and the magnetic force generating part 31 is moved in the horizontal position, the tip forming part 19 will be attracted to the magnetic force generating part 31 by the magnetic force and therefore the tip forming part 19 will move to trace the moving course of the magnetic force generating part 31. Thus, the tip forming part 19 can be inserted into the deep of such object being inspected as the large intestine.

By the way, by rotating the motors 37 and 38, the stage 130 can be moved in the lengthwise direction Y of the guide rail 35 and, by moving the guide rail 35 in the lengthwise direction X of the guide rails 34, said magnetic force generating part 31 and hall sensor 131 can be moved to any position in the horizontal plane.

By the way, when the position of the tip part body 19 is missed while the insertable part 8 is being magnetically guided by the movement of said magnetic force generating part 31, the generation of the magnetic field from the magnetic force generating part 31 will be stopped and the hall sensor 131 will be scanned to detect the position of the tip forming part 19.

By the way, instead of forming the tip forming part 19 of a permanent magnet, the hood 20 may be formed of a permanent magnet.

Thus, according to this embodiment, the insertable part 8 can be easily inserted into such bent part as the large intestine and the position of the insertable part 8 can be detected without the emission of radioactive rays.

As the permanent magnet (tip forming part 19) for the magnetic guidance is used also for the position detection, the tip part of the insertable part 8 will not be made larger than is necessary.

Also, the above mentioned magnetic force generating part 31 is made movable to the position to which the tip forming part 19 can be attracted by sliding on the wall surface within the inspected object and therefore can be formed of a small electromagnet or the like.

On the endoscope side, when the tip forming part 19 itself or the hood 20 fitted to this tip forming part 19 is made of a permanent magnet, the insertable part 8 need not be made substantially large in the outside diameter and the pain given to the patient will be able to be reduced.

Figure 23:
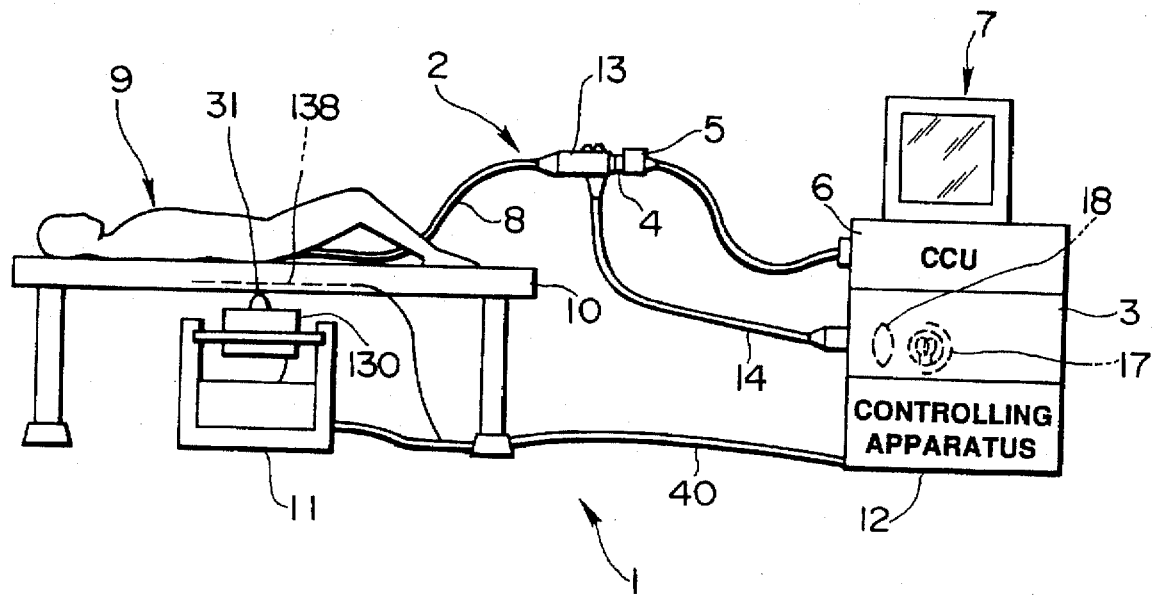
FIGS. 23 and 24 relate to the eighth embodiment of the present invention.
Figure 24:
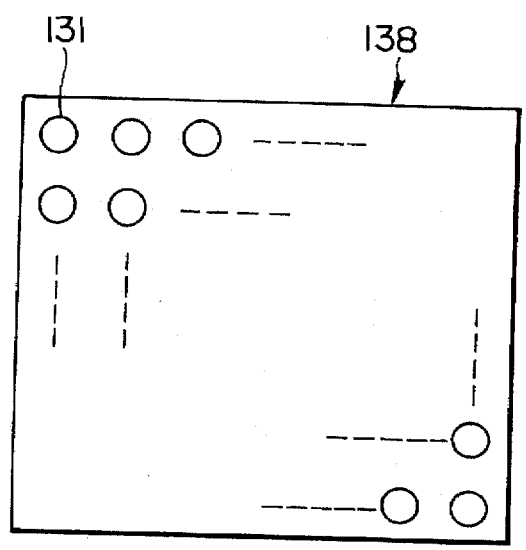

FIGS. 23 and 24 show the eighth embodiment of the present invention.

As shown in FIG. 23, in this embodiment, instead of providing the hall sensor 131 on the stage 130. a hall sensor unit 138 is incorporated into the bed 10. As shown in FIG. 24, this hall sensor unit 138 has many hall sensors 131 arranged like a matrix.

The output of said hall sensor 131 is input into the position detecting part 134 in which the position of the tip forming part 19 is detected. By the way, in this embodiment, the output of the encoder 132 is not input into said position detecting part 134.

According to this embodiment, as the hall sensor 131 is not mechanically scanned, the position of the tip forming part 19 can be detected within a short time.

When a magnetic field is generated from the magnetic force generating part 31 and the insertable part 8 is being magnetically guided, by measuring the magnetic field with the respective hall sensors 131, the distribution of magnetic fields will be able to be known.

The other formations, operations and effects are the same as in the seventh embodiment.

Figure 25:
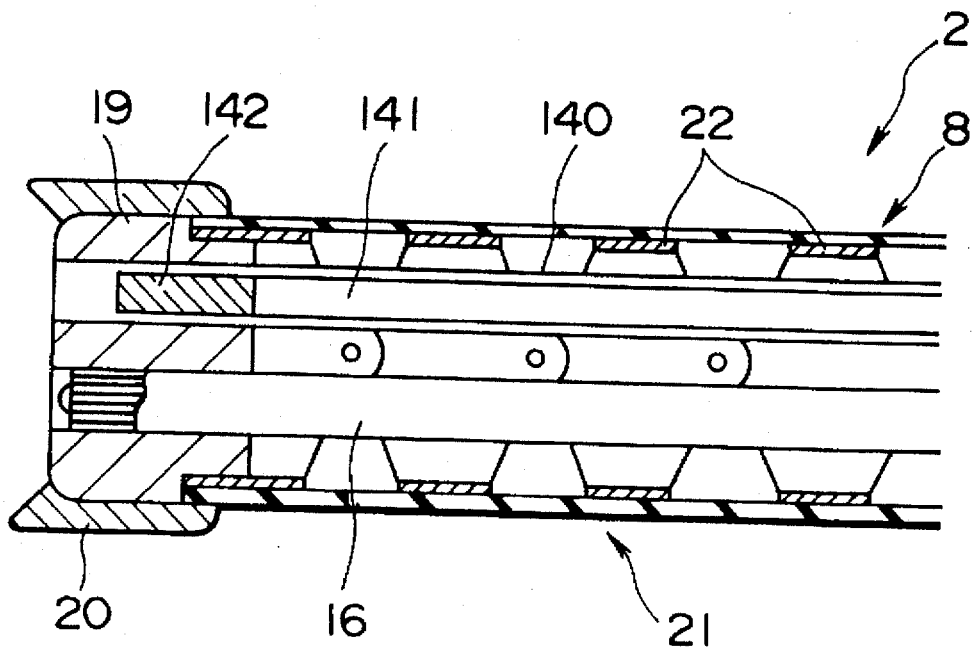
FIG. 25 is a sectioned view showing a tip part of an insertable part of an endoscope in the ninth embodiment of the present invention.

FIG. 25 shows the ninth embodiment of the present invention.

The endoscope 2 in this embodiment is provided within the insertable part 8 with a treating instrument channel 140. Instead of forming the tip forming part 19 of a permanent magnet, a probe 141 provided with a permanent magnet 142 is inserted into said treating instrument channel 140.

In this embodiment, by varying the inserted amount of said probe 141 into the treating instrument channel 140, the position of the permanent magnet 142 can be freely changed. Therefore, when the position of the permanent magnet 142 is changed and is detected by the hall sensor 131 the same as in the seventh or eighth embodiment, the form of the insertable part 8 within the inspected object will be able to be known.

Further, according to this embodiment, even in an ordinary endoscope having a treating instrument channel, when said probe 141 is kept inserted into the treating instrument channel until the tip of the insertable part 8 and said permanent magnet 142 is moved and guided by the external magnetic field, the insertable part 8 will be able to be magnetically guided.

The other formations, operations and effects are the same as in the seventh or eighth embodiment.

Figure 26:
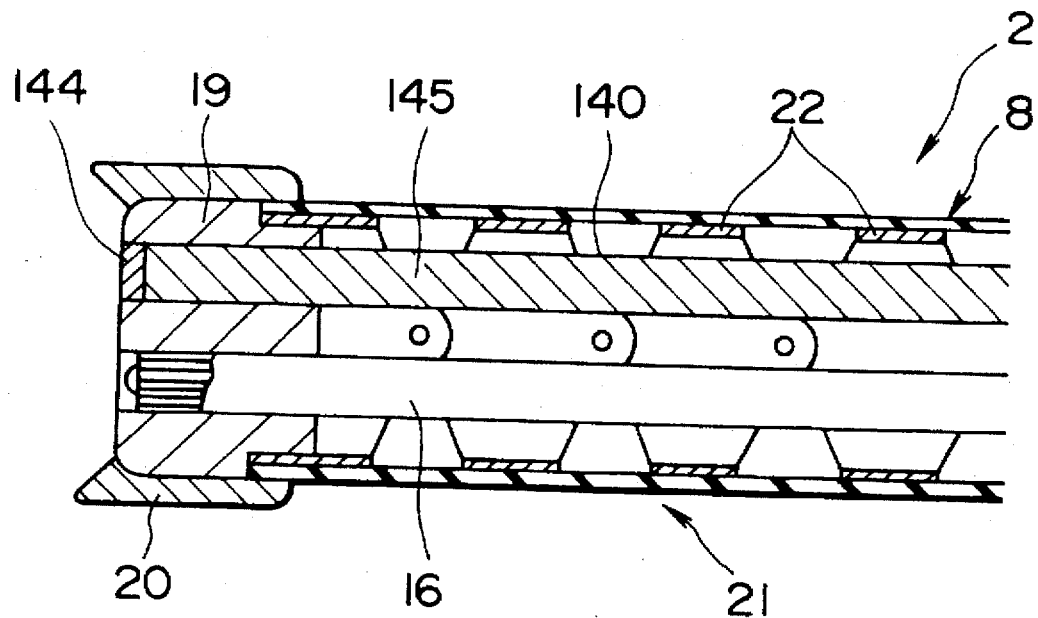
FIG. 26 is a sectioned view showing a tip part of an insertable part of an endoscope in the tenth embodiment of the present invention.

FIG. 26 shows the tenth embodiment of the present invention.

In the endoscope 2 in this embodiment, the same as in the ninth embodiment, the treating instrument channel 140 is provided within the insertable part 8. The opening at the tip of said treating instrument channel is closed with a plug 144 and said treating instrument channel 140 is filled with a magnetic fluid 145. By the way, said magnetic fluid 145 contains a permanent magnet power so that a magnetic field may be generated in a predetermined direction.

According to this embodiment, when the position of said magnetic fluid 145, that is, the position of the treating instrument channel 140 is detected by the hall sensor 131 the same as in the seventh or eighth embodiment, the form of the insertable part 8 within the inspected object will be able to be known.

The other formations, operations and effects are the same as in the seventh or eighth embodiment.

Figure 27:
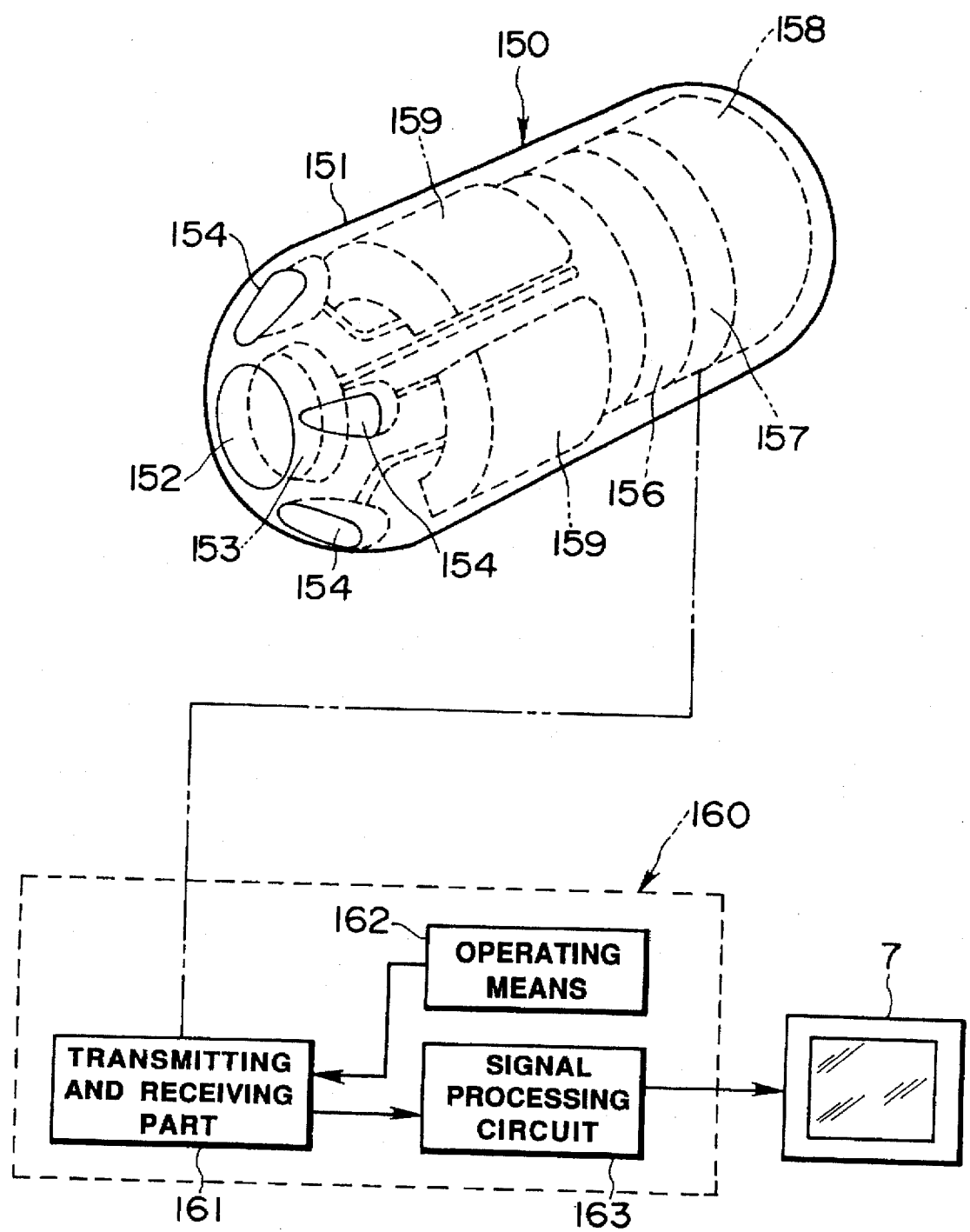
FIG. 27 is an explanatory view showing a capsule type endoscope and its control apparatus in the 11th, 16th and 24th embodiments of the present invention.

FIG. 27 shows the 11th embodiment of the present invention.

A capsule type endoscope 150 has a columnar capsule body 151 formed to be spherical in the front end part and rear end part. An observing window is provided in the central part of the front end surface of this capsule body 151 and an objective lens 152 is provided inside this observing window. A CCD 153 is provided in the image forming position of this objective lens 152. A plurality of illuminating windows are provided on the periphery of said observing window and an LED 154 is provided inside each illuminating window. On the rear end side within said capsule body 151 are provided a driving circuit 156 driving said CCD 153 and LED 154, a transmitting and receiving part 157 transmitting and receiving the output signal of said CCD 153 and various instruction signals between it and a controlling apparatus 160 arranged outside the inspected object and a power source Part 158 having a battery feeding an electric power to the respective components of the capsule type endoscope 150. A guided part 159 made of a permanent magnet is provided on the outer peripheral side within said capsule body 151.

Said control apparatus 160 comprises a transmitting and receiving part 161 transmitting and receiving signals with or without wires between it and the transmitting and receiving part 157 of said capsule type endoscope 150, an operating means 162 for transmitting various instruction signals to the capsule type endoscope 150 through said transmitting and receiving parts 161 and 157 and a signal processing circuit 163 processing the output signal of the CCD 153 input through said transmitting and receiving part 161 to convert it to a video signal which is input into the TV monitor 7 in which the object image imaged by the capsule type endoscope 150 is displayed.

The same magnetic force generating apparatus 11 and control apparatus 12 as in the seventh or eighth embodiment and the hall sensor unit 138 are also provided though not illustrated.

In this embodiment, the same as in the seventh or eighth embodiment, a magnetic field is generated from the magnetic force generating part 31, a magnetic force is generated between this magnetic force generating part 31 and the guided part of the capsule type endoscope 150, the magnetic force generating part 31 is moved and the capsule type endoscope 150 is guided. By detecting the position of the guided part 159 with the hall sensor 131, the position of the capsule type endoscope 150 is detected.

By the way, within the capsule body 151, instead of such components required for the observation as said objective lens 152, CCD 153 and LED 154, such sensors as a pH sensor and temperature sensor may be provided to detect such information within the inspected object as a pH within the stomach, pH within the intestine and temperature. Also, a collecting means for collecting an intestinal liquid or the like and a medicine administering means may be provided within the capsule body 151.

The other formations, operations and effects are the same as in the seventh or eighth embodiment.

By the way, in the seventh to 11th embodiments, the magnetic field generating means provided in the insertable part 8 of the endoscope 2 and the capsule type endoscope 150 may be of an electromagnet instead of a permanent magnet.

The magnetic field detecting means is not limited to use a hall device but may use a magnetic resistance device or the like.

The seventh to 11th endoscopes can be applied also to an electronic endoscope provided with a solid state imaging device in the tip part of the insertable part and to not only an endoscope but also a catheter.

As explained above, according to the seventh to 11th embodiments, in the guiding apparatus for magnetically guiding the insertable part, the magnetic field detecting means for detecting the position in which is provided the magnetic field generating means in the insertable part by detecting the magnetic field generated by the magnetic field generating means provided in the insertable part is provided outside the inspected object and therefore there is an effect that the position of the insertable part can be detected without the emission of radioactive rays.

FIGS. 28 to 31 show the 12th embodiment of the present invention.

Figure 29:
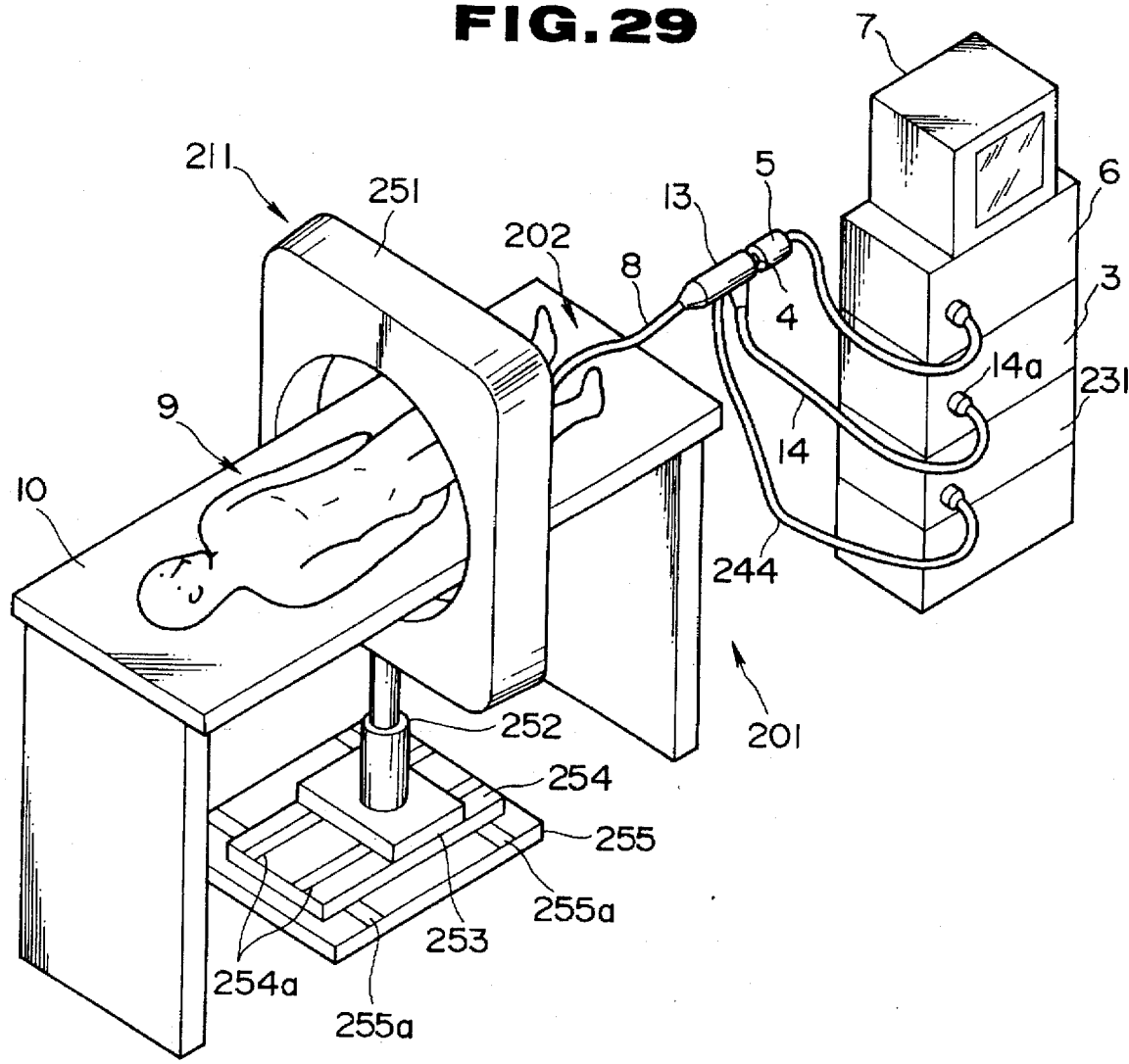

As shown in FIG. 29, an endoscope apparatus of this embodiment comprises an endoscope 202 which is a fiberscope, a light source apparatus 3 feeding an illuminating light to this endoscope 202, a TV camera 5 to be fitted to an eyepiece part 4 of said endoscope 202, a CCU 6 processing a signal for this TV camera 5, a TV monitor 7 inputting a video signal output from this CCU 6 and displaying an object image, a magnetic force generating apparatus 211 arranged around a bed 10 on which is placed a patient 9 into whom an insertable part 8 of said endoscope 202 is to be inserted and a controlling apparatus 231 to which is connected a later described coreless coil 230 provided in said endoscope 202.

Figure 28:
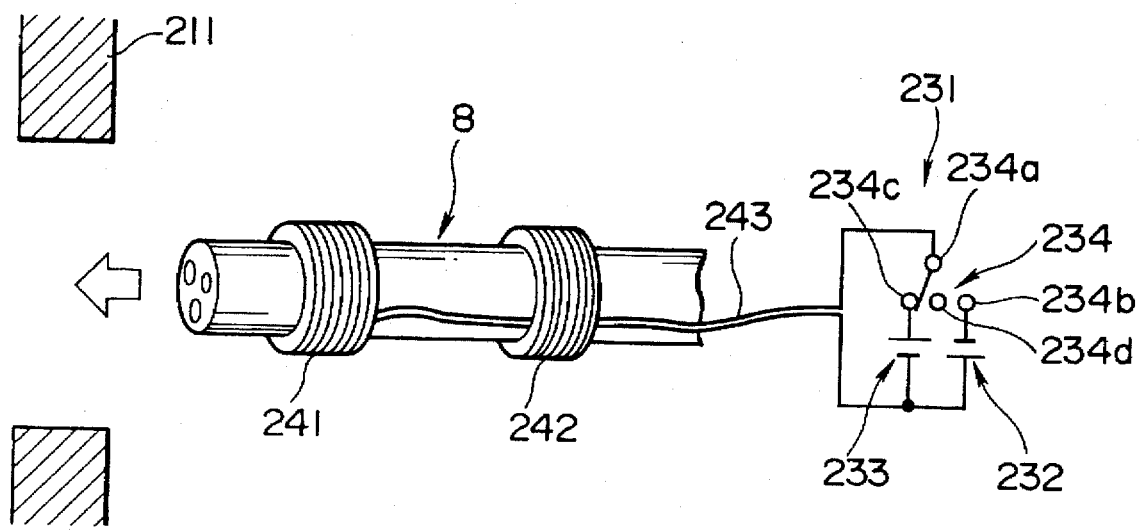
FIGS. 28 to 31 relate to the 12th embodiment of the present invention.
Figure 30:
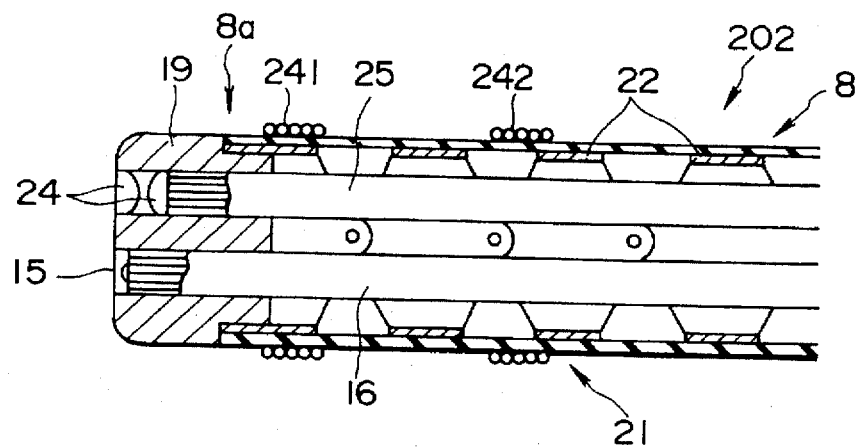

Said endoscope 202 is of substantially the same formation as of the endoscope 2 in the first embodiment but is different in respect that, as shown in FIG. 30, the tip part body 19 is fitted with no hood and is formed of a non-magnetic body. As shown in FIGS. 28 and 30, on the outer peripheral part on the tip side of said insertable part 8, two coreless coils 241 and 242 are fitted in different positions in the axial direction as guided parts. Lead wires 243 connected to these coreless coils 241 and 242 at both ends are to be connected to the controlling apparatus 212 through the outside or inside of the insertable part 8 and through a connecting cord 244 extended out of the operating part 13.

The bed 10 on which the patient 9 is to be horizontally mounted is formed of such non-magnetic material as wood.

The magnetic force generating apparatus 211 is provided around this bed 10 and has as a guiding part a magnetic field generating part 251 made of an electromagnet or permanent magnet. This magnetic field generating part 251 is provided on a vertically movable piston 252 so as to be movable in the vertical direction (made the Z direction). This piston 252 is fixed in the lower part on a movable stand 253 which is fitted on a base 254 having rails 254a in the lengthwise direction (made the X direction) of the bed 10 so as to be movable along said rails 254a. Said base 254 is fitted on a base 255 having rails 255a in the Y direction intersecting at right angles with said X and Z directions so as to be movable along said rails 255a. Thus, the magnetic field generating part 251 is movable in any of the X, Y and Z directions.

On the other hand, as shown in FIG. 28, said controlling apparatus 231 is provided with two direct current power sources 232 and 233 and a switching switch 234. Said coreless coils 241 and 242 are connected at one end to a movable contact 234a of the switching switch 234 and at the other ends to a positive pole of the power source 232 and a negative pole of the power source 233. A negative pole of the power source 232 is connected to a fixed contact 234b of the switching switch 234 and a positive pole of the power source 233 is connected to a fixed contact 234c of the switching switch 234. Nothing is connected to another fixed contact 234d of the switching switch 234. Therefore, when the movable contact 234a of the switching switch 234 is selectively connected to one of the fixed contacts 234b and 234c, the direction of the current passed through the coreless coils 241 and 242 will be able to be turned so that the magnetic force acting between the coreless coils 241 and 242 and magnetic force generating apparatus 211 will be able to be made an attraction or repulsion. When the movable contact 234a of the switching switch 234 is connected to the fixed contact 234d, no current will be passed through the coreless coils 241 and 242 and no magnetic force will be generated from the magnetic force generating apparatus 211.

The operation of this embodiment formed as in the above shall be explained in the following.

When the insertable part 8 of the endoscope 202 is inserted to some extent into such inspected object as the large intestine, then the movable contact 234a of the switching switch 234 within the control apparatus 212 is connected to one of the fixed contacts 234b and 234c and an electric current is passed through the coreless coils 241 and 242, a magnetic field will be generated from these coreless coils 241 and 242 and a magnetic force of an attraction or repulsion will be generated between the coils and the magnetic force generating apparatus 211 arranged outside the inspected object. While the endoscope image displayed in the TV monitor 7 is being observed, the magnetic field generating part 251 of the magnetic force generating apparatus 211 will be moved and the insertable part 8 will be guided within the inspected object by using said magnetic force. By switching said switching switch 234, said magnetic force may be switched from attraction to repulsion or vice versa to control the advance and retreat of the insertable part 8. When the movable contact 234a of the switching switch 234 is connected to the fixed contact 234d, no current will be passed through the coreless coils 241 and 242 which will lose the magnetism and will have no force to act on the inserted part 8 which will thus stop.

Thus, according to this embodiment, the insertable part 8 can be easily inserted into such bent part as the large intestine.

As the magnetic field generating means provided in the insertable part 8 are the coreless coils 241 and 242 generating magnetic fields when electrified, the guidance of the insertable part 8 will be able to be controlled by controlling the current passed through the coreless coils 241 and 242 and the magnetic field generated by the magnetic force generating apparatus 211 outside the inspected object may be fixed. Therefore, the guidance controllability will be improved, the apparatus will be able to be made small and the cost will be able to be reduced. By the way, as the guided part is of an electromagnet using a coreless coil, the guiding part of the magnetic force generating apparatus 211 may be of a ferromagnetic substance.

When the current passing through the coreless coils 241 and 242 is stopped, the coreless coils 241 and 242 will become non-magnetic, will be unlikely to generate heat and will be high in the safety.

By the way, in case an electromagnet is used as the magnetic field generating part 251, if a coil wound with the lengthwise direction of the bed 10 as a center is used, a magnetic field in the direction substantially parallel with the advancing direction of the insertable part 8 will be able to be generated from this magnetic field generating part 251, a magnetic force substantially parallel with this advancing direction will be able to be made to act and the insertable part 8 will be easily guided.

By the way, in this embodiment, the coreless coils 241 and 242 may be built-in in advance in the insertable part 8 or may be removably fitted as an adapter.

Further, as the power sources 232 and 233 are voltage variable power sources, the magnetic force acting on the coreless coils 241 and 242 will be able to be adjusted.

Figure 31:
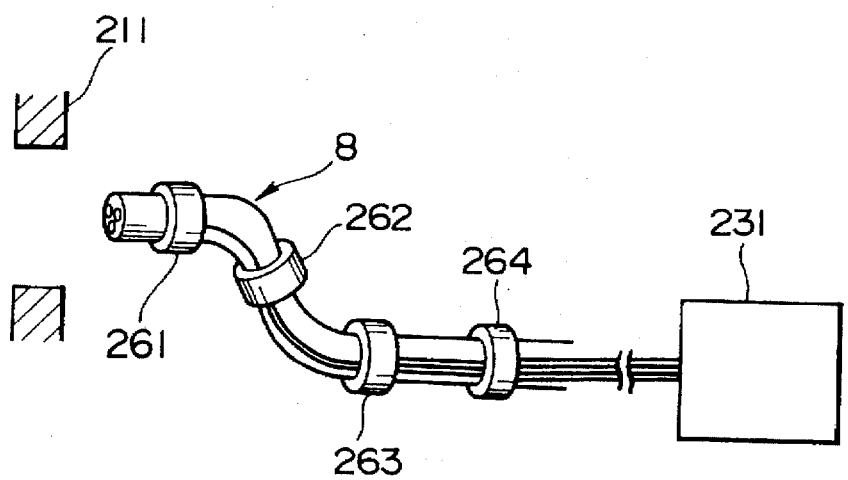

FIG. 31 shows a modification of this embodiment. In this modification, a plurality of coreless coils 261, 262, 263 and 264 are provided in different positions in the axial direction of the insertable part 8 so that a current may be selectively passed through these coils by a controlling apparatus 231.

When a current is thus selectively passed through the coils 261, 262, 263 and 264, a more complicated delicate movement will be able to be controlled.

FIGS. 32 to 34 show the 13th embodiment of the present invention.

In this embodiment, as shown in FIG. 32, an alternating current power source 236 is provided within a control apparatus 231 so that said alternating current power source 236 may be connectable to the coreless coils 241 and 242 of the 12th embodiment.

When an alternating current is flowed through the coreless coils 241 and 242 by said alternating current power source 236, a magnetic force generated between the coils and magnetic force generating apparatus 211 will alternately turn to attraction and repulsion so that the insertable part 8 may vibrate in the axial direction. By this vibration, the static friction between the insertable part 8 and inspected object will be reduced and the insertable part 8 will become easy to insert.

By the way, within the above mentioned controlling apparatus 231, not only the above mentioned alternating current power source 236 but also the direct current power sources 232 and 233 and switching switch 234 in the 12th embodiment may be provided so that the alternating current and direct current may be selectively passed through the coreless coils 241 and 242.

The other formations, operations and effects are the same as in the 12th embodiment.

FIGS. 33 and 34 show a modification of this embodiment. In this modification, as shown in FIG. 33, a voltage variable direct current power source 237 is connected in series to said alternating current power source 236 so that a direct current may be superimposed on the alternating current passed through the coreless coils 241 and 242.

As shown in FIG. 34(A), when the alternating current is made zero, the insertable part 8 will vibrate in the axial direction with a predetermined position as a center and, as shown in FIG. 34(B), when a direct current is superimposed, the insertable part 8 will advance or retreat while vibrating in the axial direction.

FIG. 35 shows the 14th embodiment of the present invention.

In this embodiment, four saddle-like wound coreless coils 271, 272, 273 and 274 are provided on the outer periphery of an insertable part 8. The coreless coils 271 and 272 are arranged in the positions symmetrical with each other so that, when a current is passed through these coreless coils 271 and 272, a magnetic flux will be generated in the diametral direction. The coreless coils 273 and 274 are arranged in the positions symmetrical with each other in the positions different in the axial direction of the insertable part 8 from those of said coreless coils 271 and 272 and are arranged in the positions different by 90 degrees in the peripheral direction from those of the coreless coils 271 and 272. When a current is passed through these coreless coils 273 and 274, a magnetic flux will be generated in the diametral direction intersecting at right angles with the direction of the magnetic flux generated by said coreless coils 271 and 272.

The outside magnetic force generating apparatus 211 generates such magnetic field as generates a magnetic force between it and the electrified coreless coils 271 to 174.

In this embodiment, when an alternating current is applied to said coreless coils 271 to 274, by the mutual action with the constant magnetic field by the outside magnetic force generating apparatus, the insertable part 8 will be vibrated in the diametral direction. By this vibration, the stationary friction between the insertable part 8 and inspected object will decrease and the insertable part 8 will be more easily inserted.

When a direct current is selectively applied to said coreless coils 271 to 274, the insertable part 8 will be able to be guided in the respective vertical and horizontal directions.

The other formations, operations and effects are the same as in the 12th embodiment.

Figure 36:
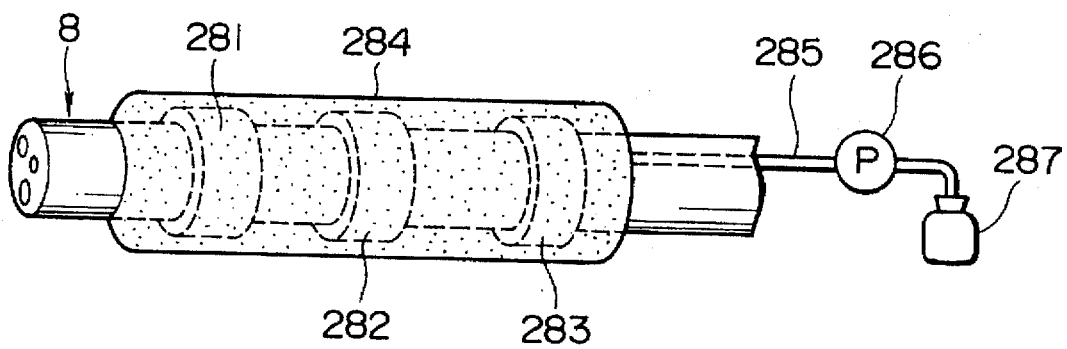
FIGS. 36 to 38 relate to the 15th embodiment of the present invention.
Figure 37:
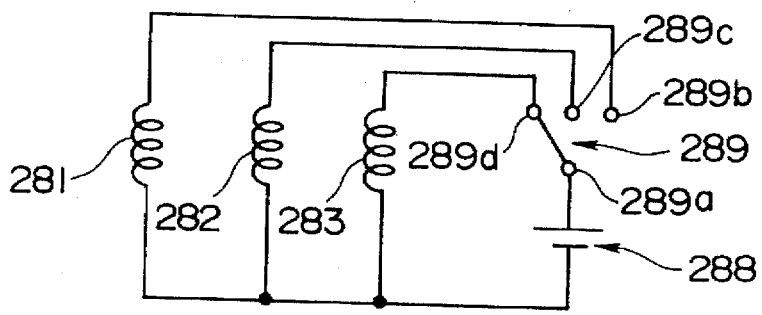
Figure 38:
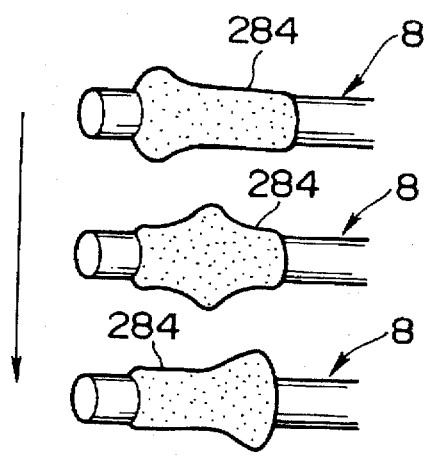

FIGS. 36 to 38 show the 15th embodiment of the present invention.

As shown in FIG. 36, in this embodiment, three coreless coils 281, 282 and 283 are provided in the positions different in the axial direction of the outer peripheral part of an insertable part 8 of an endoscope 202. A magnetic fluid balloon 284 is fitted to the outer peripheral part of the insertable part 8 to cover these coils 281, 282 and 283. A magnetic fluid tank 287 provided outside the endoscope 202 is connected to said magnetic fluid balloon 284 through a tube 285 inserted through the insertable part 8 and a pump 286 is interposed in said tube 285. The magnetic fluid balloon 284 can be filled with the magnetic fluid stored in the magnetic fluid tank 287 by said pump 286.

As shown in FIG. 37, said coreless coils 281, 282 and 283 are connected each at one end respectively to the fixed contacts 289$b$, 289$c$ and 289$d$ of a switching switch 289. The movable contact 289$a$ of said switching switch 289 is connected to the positive pole of a direct current power source 288 whose negative pole is connected to the coreless coils 281, 282 and 283 at the other ends. Therefore, by switching said switching switch 289, a current can be passed selectively through the coreless coils 281, 282 and 283.

In this embodiment, the magnetic force generating apparatus 211 is not provided.

The other formations are the same as in the 12th embodiment.

The operation of this embodiment shall be explained in the following.

When the insertable part 8 is inserted into an inspected object, the magnetic fluid balloon 284 is filled with a magnetic fluid and the movable contact 289$a$ of the switching switch 289 is cyclically connected to the fixed contacts 289$b$, 289$c$, 289$d$, 289$b$, . . . in the order mentioned, the coreless coils 281, 282 and 283 will generate magnetic fields in this order, the magnetic fluid will collect around the coreless coils having generated magnetic fields and therefore the magnetic fluid balloon 284 will be inflated. Thus, as shown in FIG. 38, said balloon 284 will be inflated first on the periphery of the coil 284, then on the periphery of the coil 282 and then on the peripery of the coil 283. When this operation is repeated, the balloon 284 in contact with the inside wall of the inspected object will vermicularly move and the insertable part 8 will be automatically inserted into the deep within the inspecated object.

Thus, according to this embodiment, the insertable part 8 of the endoscope 202 can be automatically inserted without using the outside magnetic force generating apparatus 211.

The 16th embodiment of the present invention shall be explained in the following by using FIG. 27.

This embodiment is of a capsule type endoscope the same as in the 11th embodiment. In this embodiment, the guided part 159 is formed of a coreless coil instead of a permanent magnet. The electric power for this coreless coil is fed from the power source part 158. The other formations of the capsule type endoscope 150 and the formation of the control apparatus 160 are the same as in the 11th embodiment.

Though not illustrated, the same magnetic force generating apparatus 211 as in the 12th embodiment is provided around the inspected object.

In this embodiment, the same as in the 12th embodiment, an electric current is passed through the coreless coil of the guided part 159, a magnetic field is generated from this coreless coil, a magnetic field is generated from the magnetic force generating apparatus 211, a magnetic force is generated between this magnetic force generating apparatus 211 and the coreless coil of the capsule type endoscope 150, the magnetic force generating apparatus 211 is moved and the capsule type endoscope 150 is guided.

By the way, within the capsule body 151, instead of such components required for the observation as said objective lens 152. CCD 153 and LED 154, such sensors as a pH sensor and temperature sensor may be provided so that a pH within the stomach, pH within the intestine, temperature and the like may be detected.

The other formations, operations and effects are the same as in the 12th embodiment.

By the way, the 12th to 16th embodiments can be applied not only to an endoscope but also to a catheter.

The 12th to 16th embodiments can be applied also to an electronic endoscope provided with a solid state imaging device in the tip part of the insertable part.

Now, in case a permanent magnet, ferromagnetic substance or electromagnet is provided in the tip part of the insertable part of said electronic endoscope and the insertable part is magnetically guided by the manetic force generating part provided outside the body, when a high magnetic field is generated by the magnetic force generating part, the endoscope image will be disturbed. Therefore, the 17th to 22nd embodiments in which the insertable part can be magnetically guided without disturbing the endoscope image shall be shown in the following.

FIGS. 39 to 42 show the 17th embodiment of the present invention.

Figure 39:
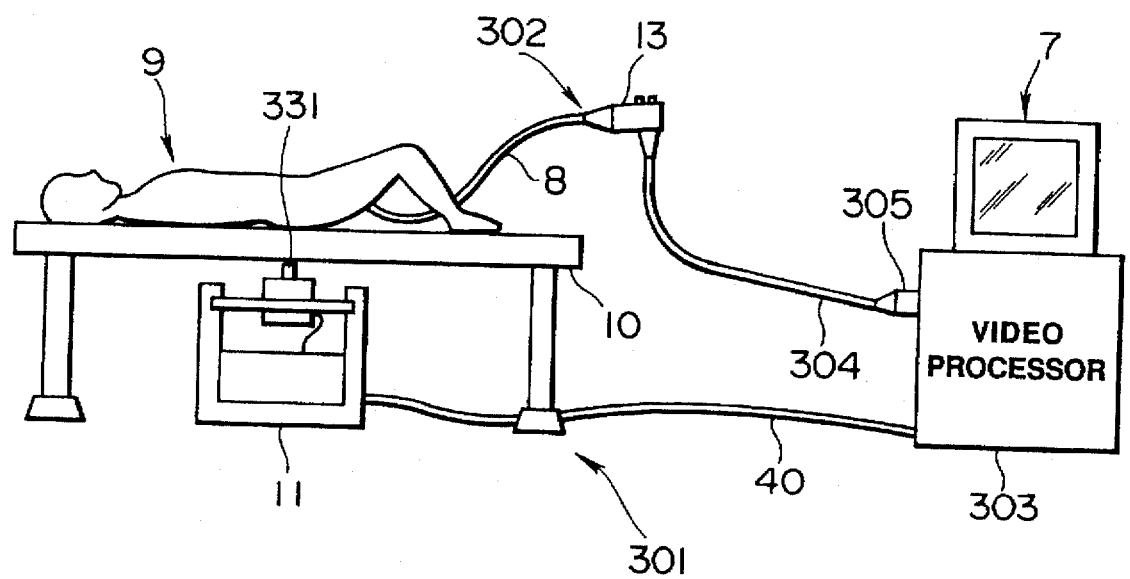

As shown in FIG. 39, an endoscope apparatus 301 comprises an electronic endoscope 302, a video processor 303 feeding an illuminating light to this electronic endoscope 302 and processing a signal for this electronic endoscope 302, a TV monitor 7 inputting a video signal output from said video processor 303 and displaying an object image and a magnetic force generating apparatus 11 arranged below a bed 10 on which is placed a patient 9 into whom an insertable part 8 of said endoscope 302 is inserted. Said magnetic force generating apparatus 11 has a magnetic force generating part 31 which is movable in a horizontal plane. The formation of this magnetic force generating apparatus 11 is the same as in the first embodiment.

Said electronic endoscope 302 is provided with a flexible elongate insertable part 8, an operating part 13 connected to this insertable part 8 at the rear end and a universal cord 304 extended from the side of this operating part 13. Said universal cord 304 is provided at the end with a connector 305 removably connected to a connector receptacle 309 of said video processor 303.

Figure 40:
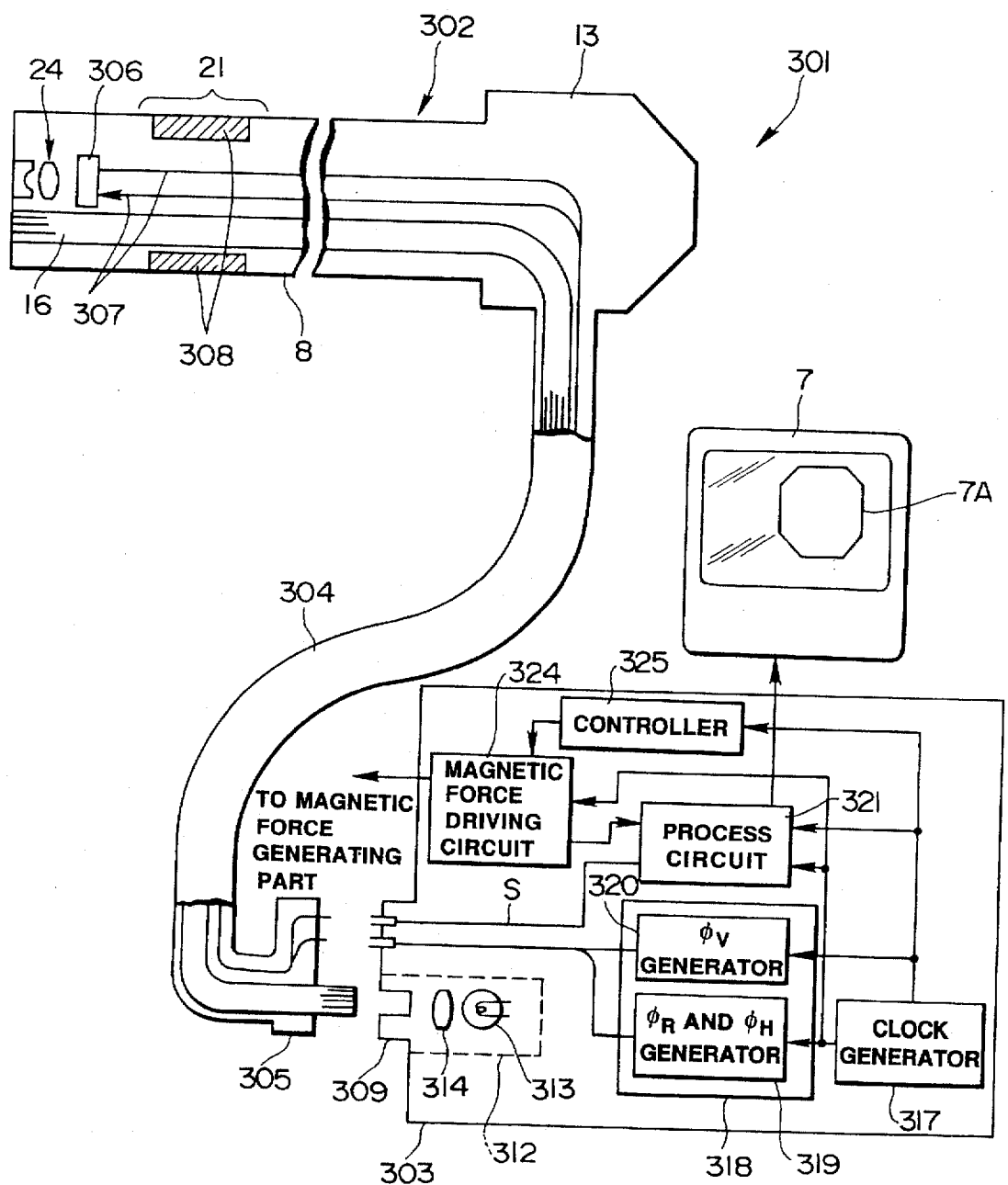

As shown in FIG. 40, a solid state imaging device, for example, a CCD 306 is arranged in the image forming position of an objective lens 24 provided in the tip part of said insertable part 8. A signal transmitting cable 307 connected to this CCD 306 is inserted through the insertable part 8, operating part 13 and universal cord 304 and is connected to said connector 305. A light guide 16 is also connected at the entrance end to said connector 305. Also, a strong magnetic body 308 is fitted to the outer peripheral part of a bendable part 21 of said insertable part 8.

A light source part 312 having a lamp 313 and lens 314 is provided within said video processor 303 so that an illuminating light emitted from said lamp 313 may be condensed by the lens 314 and may enter said light guide 16 at the entrance end. A clock generator 317, a driving circuit 318 into which is input a clock generated from this clock genertor 317, a process circuit 321, magnetic force driving circuit 324 and controller 325 are also provided within said video processor 303.

A clock signal generated by said clock generator 317 is input into the driving circuit 318 which produces a CCD driving signal. This driving circuit 318 has a reset and horizontal transmitted pulse generator 319 and a vertical transmitted pulse generator 320. Said generators 319 and 320 generate respectively a (charge) reset pulse $\Phi_R$ and horizontal transmitted pulse $\Phi_H$ and a vertical transmitted pulse $\Phi_V$.

Said vertical transmitted pulse $\Phi_V$, charge reset pulse $\Phi_R$ and horizontal transmitted pulse $\Phi_H$ are applied to the CCD 306 through the signal transmitting cable 307.

When a driving signal from said driving circuit 318 is applied, the CCD 306 will output a photoelectrically converted signal S which will be input into the process circuit 321 through the signal transmitting cable 306.

Figure 41:
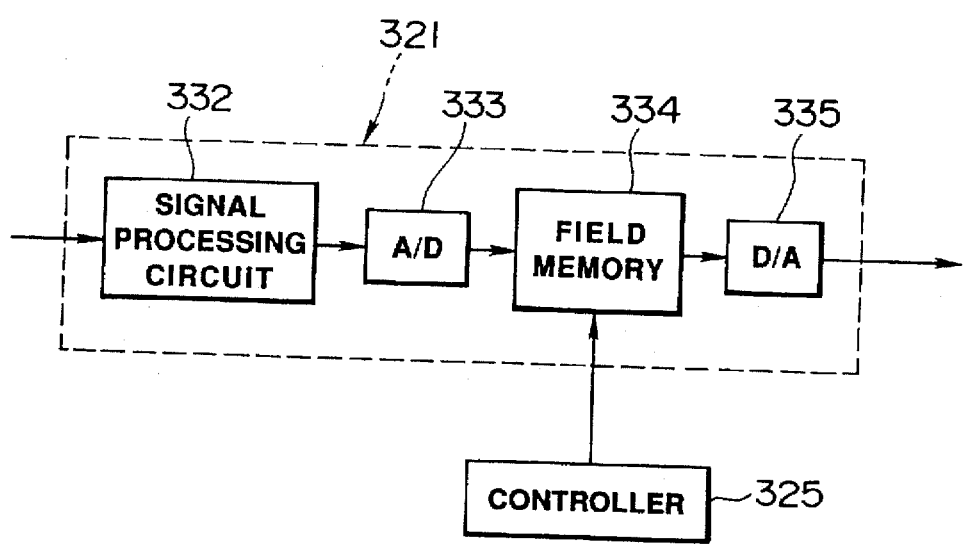

Said process circuit 321 inputs the signal S output from the CCD 306 and outputs a video signal to the TV monitor 7. As shown in FIG. 41, this process circuit 321 comprises a signal processing circuit 332 processing the output signal of CCD 306 to convert it to a video signal, and A/D converter 333 converting the video signal from this signal processing circuit 332 to a digital signal, a field memory 334 memorizing the output signal of this A/D converter and a D/A converter 335 converting the signal read out of this field memory 334 to an analogue signal and outputting it to the TV monitor 7 or a VTR not illustrated. Said field memory 334 is controlled by the controller 325 in writing in and reading out.

Said magnetic force driving circuit 324 drives the magnetic force generating part 31 of the magnetic force generating apparatus 11. When a magnetic field is generated from said magnetic force generating part 31, a magnetic force (for example, an attraction) will be generated between this magnetic force generating part 31 and the ferromagnetic substance 308 provided in the insertable part 8 so that the insertable part 8 may be magnetically guided by this magnetic force.

In this embodiment, the field memory 334 within the process circuit 321 and the magnetic force driving circuit 324 are controlled by the controller 325 and, as shown in FIG. 42, a video signal is obtained at intervals of one field and is displayed in the monitor 7 or recorded in a VTR or the like. In the field obtaining no video signal, a magnetic field is generated from the magnetic force generating part 331 and is magnetically guided to the insertable part 8. By the way, in the field obtaining no video signal, the image of the prior field memorized in the field memory 334 is read out once again.

Thus, according to this embodiment, as the timing of obtaining the endoscope image and the timing of magnetically guiding the insertable part are perfectly independent of each other, the insertable part 8 can be magnetically guided without disturbing the endoscope image with the magnetic field.

By the way, the insertable part 8 may be provided with such coreless coil as in the 12th embodiment instead of the strong magnetic body 308.

The other formations, operations and effects of this embodiment are the same as in the 12th embodiment.

FIG. 43 shows the 18th embodiment of the present invention.

In this embodiment, only the control of the field memory 334 and magnetic force driving circuit 324 by the controller 325 is different from the 17th embodiment. FIG. 43 shows synchronizing signals of video signals, that is, a vertical synchronizing signal VS and horizontal synchronizing signal HS. As shown in FIG. 43, the video image is obtained in all the respective fields and is displayed or recorded and the magnetic guidance is made in the vertical blanking period (vertical synchronizing signal period).

According to this embodiment, the insertable part 8 can be magnetically guided without deteriorating the picture quality.

The other formations, operations and effects are the same as in the 17th embodiment.

FIG. 44 shows the 19th embodiment of the present invention.

In this embodiment, the operation of the controller 325 is switched by a switch not illustrated or the like so that, at the magnetic guiding time, the same as in the 17th embodiment, a field mode in which the video signal is input at intervals of one field will be made and a magnetically guiding magnetic field will be generated in the field in which no video image is input and, at the ordinary time when no magnetic guidance is made, a frame mode in which the video image is obtained in all the fields will be made.

According to this embodiment, at the magnetic guiding time, as no high picture quality will be required, a field mode will be made but, at the ordinary observing time, it will be able to be used in a frame mode so that a high picture quality may be obtained.

The other formations, operations and effects are the same as in the 17th embodiment.

FIG. 45 shows the 20th embodiment of the present invention.

In this embodiment, at the magnetic guiding time, with the field memory 334, at regular intervals, freezing (making a stationary image) and defreezing the image will be alternately made so that the magnetic guidance may be made at the freezing time. Therefore, at the magnetic guiding time, a frozen image not disturbed by the magnetic fiels will be displayed in the TV monitor 7.

According to this embodiment, a magnetic guidance can be made efficiently.

The other formations, operations and effects are the same as in the 17th embodiment.

Figure 46:
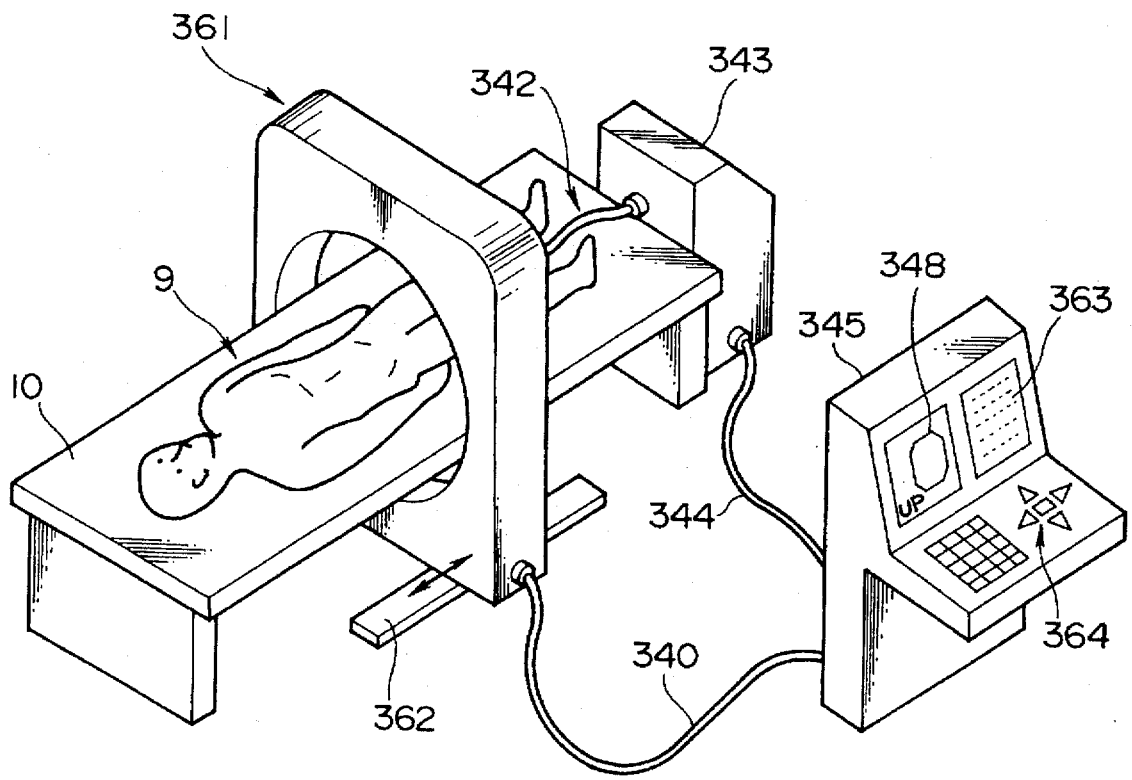

FIGS. 46 and 47 show the 21st embodiment of the present invention.

In the 17th embodiment, the insertable part 8 is guided two-dimensionally but, in this 21st embodiment, a three-dimensional guidance is possible.

In this embodiment, as shown in FIG. 46, an annular magnetic force generating apparatus 361 surrounding the patient 9 as a center is provided instead of the magnetic force generating apparatus 11 in the 17th embodiment. This magnetic force generating apparatus 361 is made movable on a rail 362 in the lengthwise direction of the bed 10 on which is mounted the patient 9.

Also, in this embodiment, an insertable part 342 of an endoscope is connected at the base to an observing unit 343 having a video processor 303 built-in. This observing unit 343 is connected through a cable 344 to an operating part 345 having a control circuit controlling said magnetic force generating apparatus 361 which is also connected to said operating part 345 through a cable 340. Said operating part 345 is provided with an endoscope image monitor 348, a patient data displaying part 363 and a guiding switch 364 connected to a control circuit controlling the magnetic force generating apparatus 361.

Figures 47A, 47B:
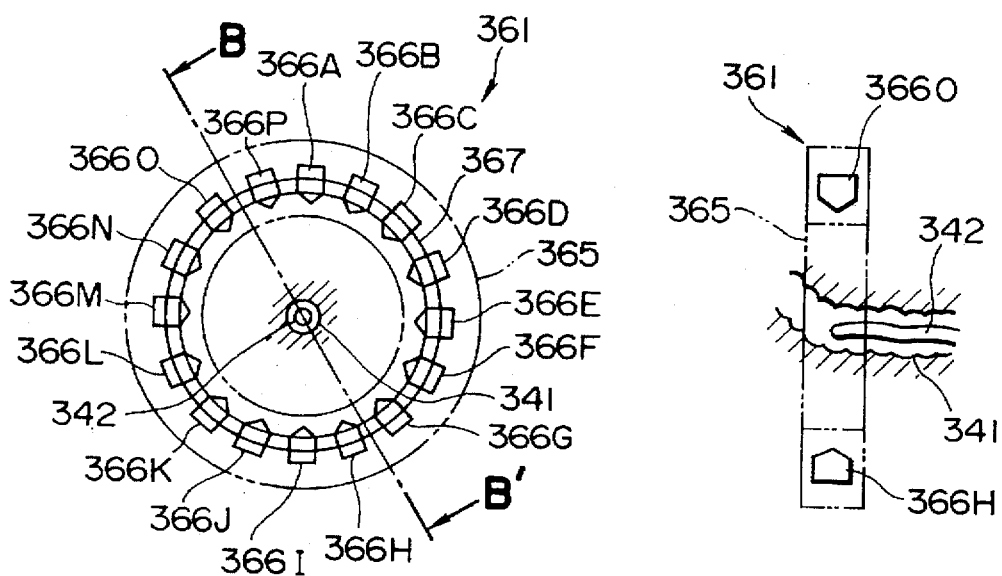
FIG. 47(A) is an explanatory view showing the formation of a magnetic force generating apparatus.
FIG. 47(B) is a sectioned view on line B–B' in FIG. 47(A).

As shown in FIGS. 47(A) and (B), said magnetic force generating apparatus 361 has an annular part 365 provided with a ring-like guide ring 367 on which a plurality of magnetic force generating parts 366A to 366P are arranged in the peripheral direction so that a magnetic field may be generated selectively from any magnetic force generating part by the operation of the guiding switch 364 of said operating part 345.

By the way, FIGS. 47(A) and (B) show said insertable part 342 as inserted into the large intestine 341.

In this embodiment, when, for example, the magnetic force generating parts 366A and 366I are selected and the intensities of the magnetic forces by the respective magnetic force generating parts 366A and 366I are properly adjusted, the insertable part 342 will be able to be moved in the vertical direction.

When, for example, the respective sets of the magnetic force generating parts 366P, 366A and 366B and of the magnetic force generating parts 366H, 366I and 366J are selected and magnetic forces are generated from them, a magnetic field stronger than of one magnetic force generating apparatus will be obtained and a stabilized guiding operation will be possible.

Also, when such three as, for example, the magnetic force generating parts 366A, 366G and 366K are selected and magnetic forces are generated from them, the movement in a wide range of the insertable part 342 will be possible.

Further, when the magnetic force generating parts 366A to 366P are variously combined, the insertable part 342 will be able to be guided in various manners.

By the way, the timing of generating magnetic fields from the magnetic force generating parts 366A to 366P in this embodiment is the same as in the 17th to 20th embodiments.

Also, in the endoscope image monitor 348, the direction of the magnetic force generated by the magnetic force generating apparatus 361 is displayed. For example, if the direction of the magnetic force is upward, as shown in FIG. 46, a message of "UP" will be displayed.

The other formations, operations and effects are the same as in the 17th to 20th embodiments.

As explained above, according to the 17th to 21st embodiments, as a coreless coil generating a magnetic field when a current is passed through it is used as a magnetic field generating means provided in an insertable part to be guided, there are effects that the guidance can be controlled by controlling the current to be passed through the coreless coil, the guidance controllability will improve, the coreless coil will become non-magnetic and will generate no heat when the passage of the current through the coreless coil is stopped and the safety will improve.

Figure 48:
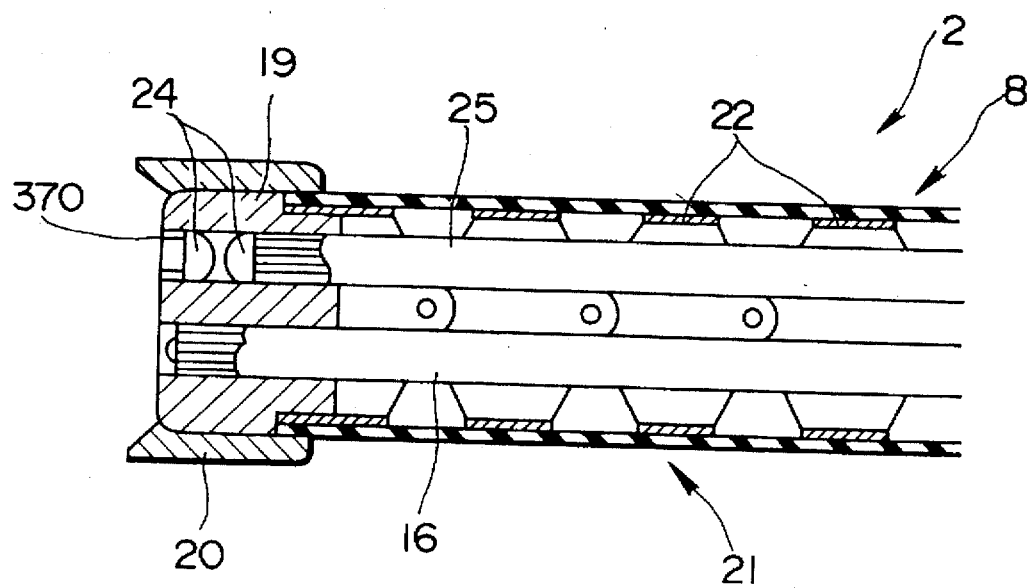

FIGS. 48 and 49 show the 22nd embodiment of the present invention.

Figures 49A, 49B:
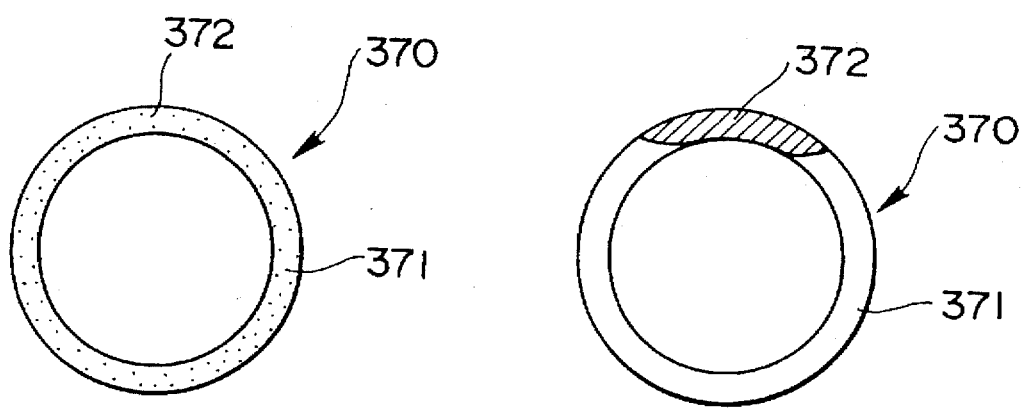
FIG. 49(A) is an explanatory view showing an indication when an external magnetic field is not generated.
FIG. 49(B) is an explanatory view showing an indication when an external magnetic field is generated.

The endoscope of this embodiment is of substantially the same formation as in the first embodiment but at least one of the tip part forming part 19 and the hood 20 fitted to this tip part forming part 19 is formed of a ferromagnetic substance. The same as in the first embodiment, the insertable part 8 is guided by the magnetic force generated between this ferromagnetic substance and the outside magnetic force generating apparatus 11. Also, in this embodiment, an indicating apparatus 370 is provided on the front surface of the objective lens 24 provided in the tip part of said insertable part 8. As shown in FIGS. 49(A) and (B), this indicating apparatus 370 has a hollow ring 371 formed of a transparent glass tube or tube. A magnetic fluid 372 and a transparent liquid equal in the specific gravity to this magnetic fluid 372 and high in the dispersibility are enclosed within this ring 371. Said magnetic fluid 372 is to be observed with the objective lens 24.

Within a uniform magnetic field, as shown in FIG. 49(A), the magnetic fluid 327 will be uniformly distributed but, when a magnetically guiding magnetic field is generated from outside, as shown in FIG. 49(B), the magnetic fluid 372 will deviate to one side so that the direction of the magnetic field may be known in the endoscope image.

The other formations, operations and effects are the same as in the first embodiment.

By the way, in the capsule type endoscope shown in FIG. 27, a ferromagnetic substance may be used for the guided part 159 and, the same as in said 17th to 20th embodiments, the timing of obtaining the video signal and the timing of magnetically guiding this capsule type endoscope may be separated from each other.

FIGS. 50 to 60 show the 23rd embodiment of the present invention.

Figure 51:
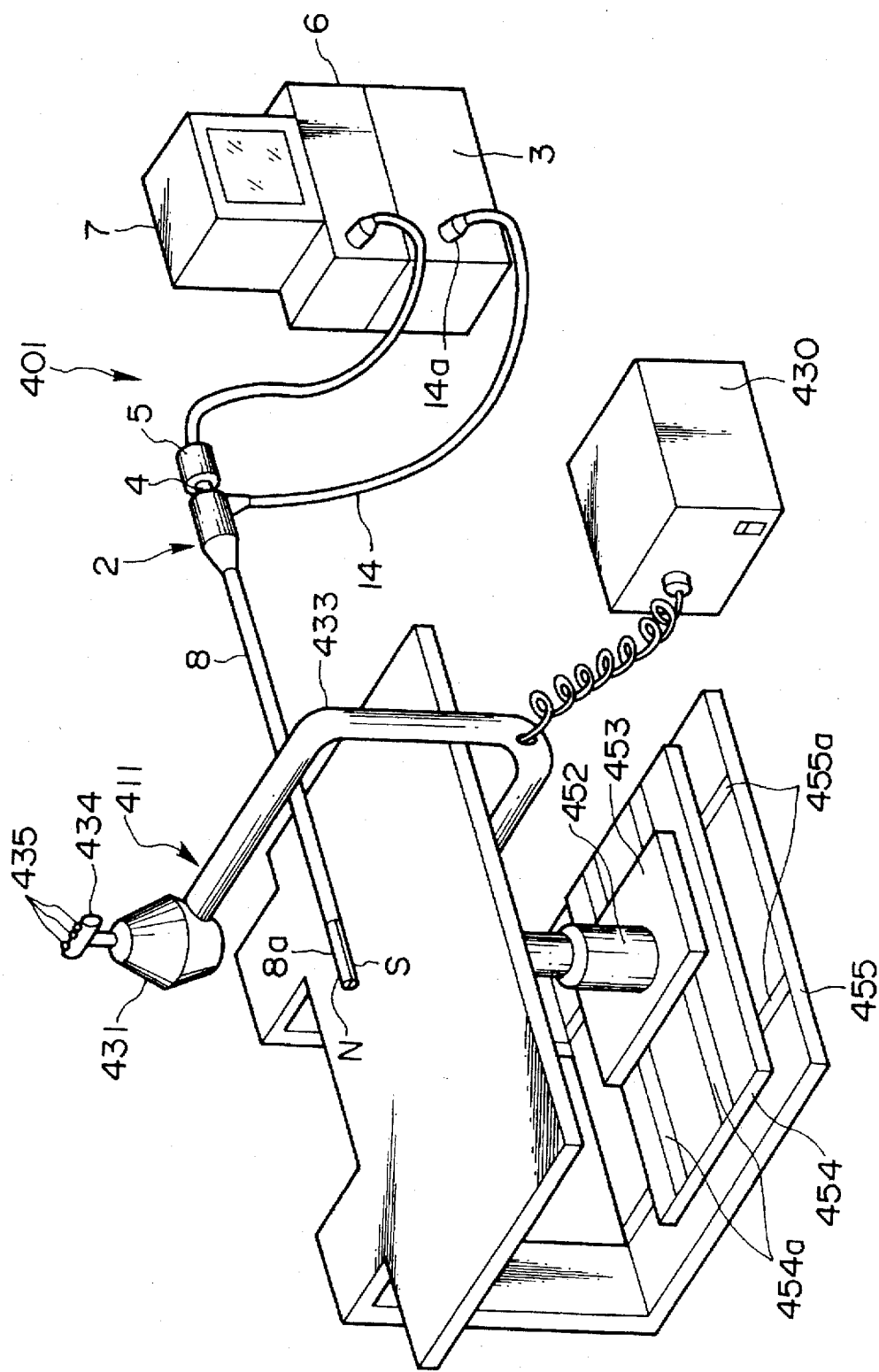
Figure 52:
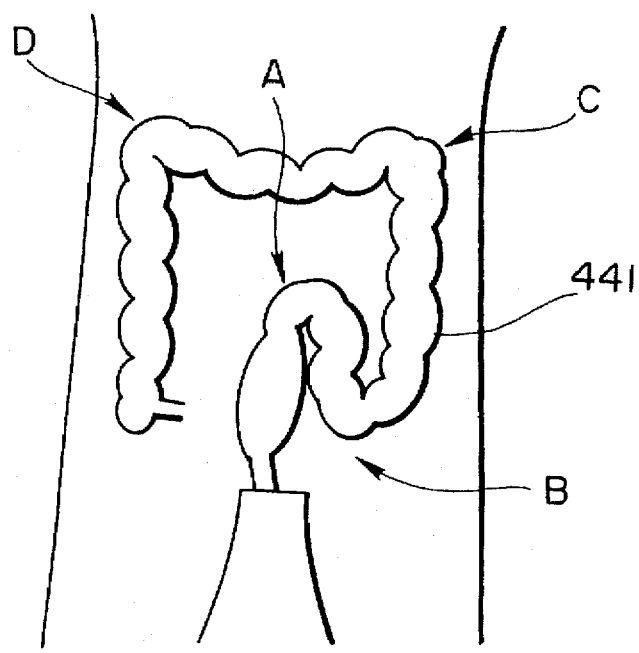

As shown in FIGS. 51 and 52, an endoscope apparatus 401 of this embodiment comprises an endoscope 2 which is a fiberscope, a light source apparatus 3 feeding an illuminating light to this endoscope 2, a TV camera fitted to the eyepiece part 4 of said endoscope 2, a CCU 6 processing the signal for this TV camera, a TV monitor inputting the video signal output from this CCU 6 and displaying an object image, a magnetic force generating apparatus 411 arranged around a bed 10 on which is placed a patient 9 into whom the insertable part 8 of said endoscope 2 is inserted and a power source 430 feeding an electric power to said magnetic force generating apparatus 411.

The formations and opertions of said light source apparatus 3, TV camera 5, CCU 6 and TV monitor 7 are the same as in the first embodiment.

The formation of the endoscope 2 is also substantially the same as in the first embodiment.

Figure 50:
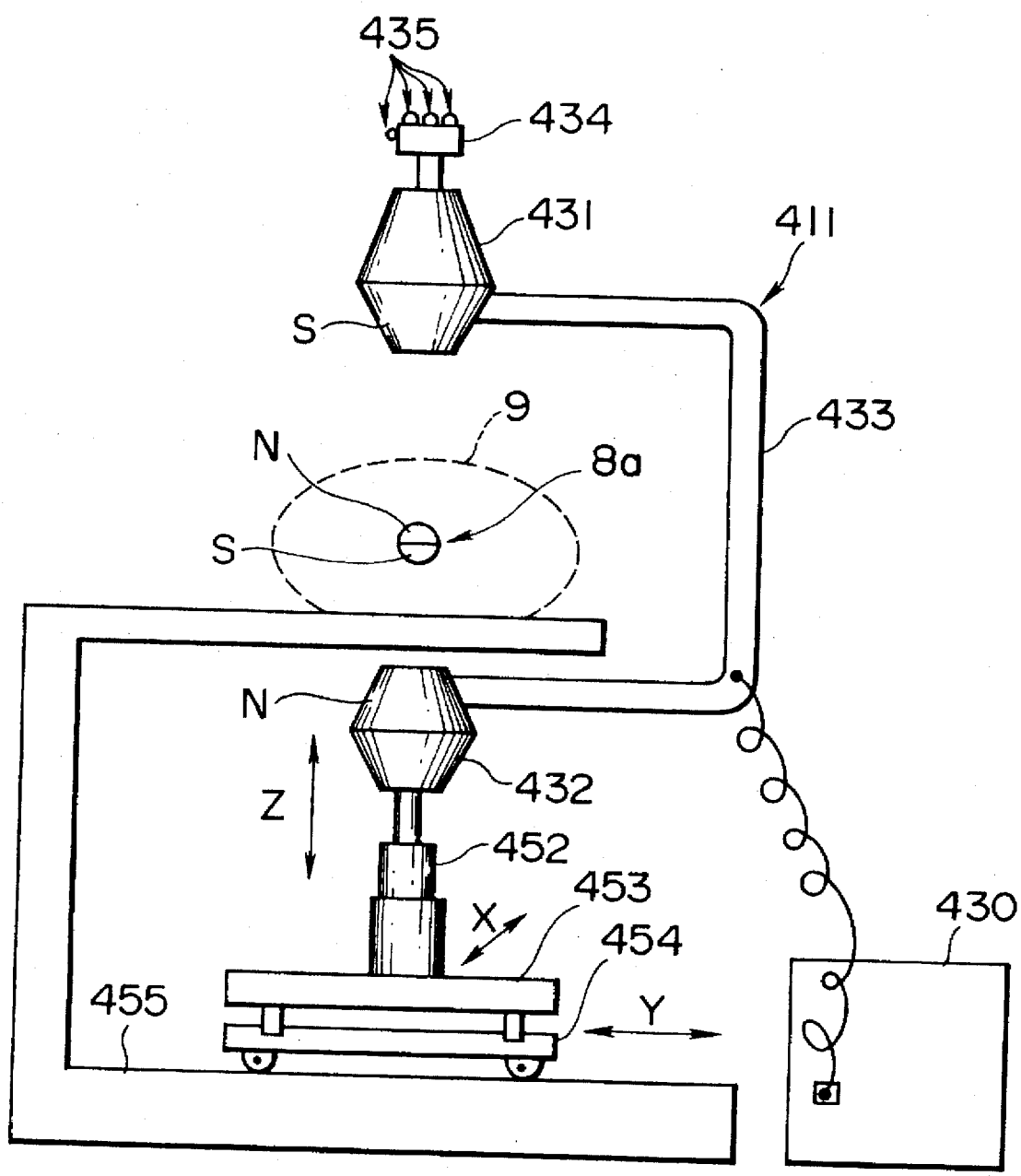
FIGS. 50 to 60 relate to the 23rd embodiment of the present invention.

As shown in FIGS. 50 and 51, at least one of the tip forming part 19 in the tip part of the insertable part 8 and the hood 20 fitted to this tip forming part 19 is formed to be a guided part of a permanent magnet magnetized to be an N pole on the upper side and an S pole on the lower side. The other parts of the insertable part 8 than those are formed of non-magnetic bodies (aluminum, copper alloy, plastics, etc.) not attracted by the magnetic force.

The bed 10 on which the patient 9 is to be horizontally mounted is formed of such non-magnetic material as wood.

The magnetic force generating apparatus 411 is provided around this bed 10 and comprises a lower head 432 arranged below said bed 10, an upper head 431 arranged to be opposed to said lower head 143 with the patient 9 between them and an arm 433 connecting both heads 431 and 432 with each other. Said lower head 432 is provided on a vertically movable piston 452 so as to be movable in the vertical direction (which shall be the Z direction). This piston 452 is fixed in the lower part on a movable stand 453 which is fitted on a base 454 having rails 454a in the lengthwise direction (which shall be the X direction) of the bed 10 so as to be movable along said rails 454. Said base 454 is fitted on a base 455 having rails 455a in the Y direction intersecting at right angles with said X and Z directions so as to be movable along said rails 455a. By the way, said base 455 is made integral with the bed 10. Thus, the arm 433 and both heads 431 and 432 are movable in any of the X, Y and Z directions.

Both of said beds 431 and 432 have respectively electromagnets generating magnetic fields when an electric current is passed through them by said power source 430. A grip 434 is provided on said upper head 431 so as to be gripped to integrally move both heads 431 and 432 and is provided with a plurality of switches 435 which will be able to turn the direction of the current passed through the coils of the electromagnets within said heads 431 and 432, to vary the current or to stop passing the current when operated.

The operation of this embodiment formed as in the above shall be explained in the following.

In case the insertable part 8 of the endoscope 2 is inserted to some extent into the body cavity of the patient 9 and is then magnetically guided and an electric current is passed through the electromagnets of the respective heads 431 and 432 so that the upper head 431 may produce an S pole on the patient 9 side and the lower head 432 may produce an N pole on the patient side as shown, for example, in FIG. 50, magnetic forces of attractions will be produced respectively between the upper side of the tip part 8a and the upper head 431 and between the lower side of the tip part 8a and the lower head 431. When a current is passed through the electromagnets of the respective heads 431 and 432 so that, on the cotrary, the upper head 431 may produce an N pole on the patient 9 side and the lower head 432 may produce an S pole on the patient 9 side, magnetic forces of repulsions will be produced respectively between the upper side of the tip part 8a and the upper head 431 and between the lower side of the tip part 8a and the lower head 431. The grip 434 is gripped and the positions of the heads 431 and 432 are adjusted so that the tip part 8a may be positioned in the position in which the force acting on the tip part 8a, that is, the gravity and the magnetic forces in the respective upward and downward directions are balanced with each other in at least one direction (in the vertical direction in this case). When said grip 434 is gripped and the heads 431 and 432 are moved from this state, the insertable part 8 will be able to be guided following this movement.

Figure 53:
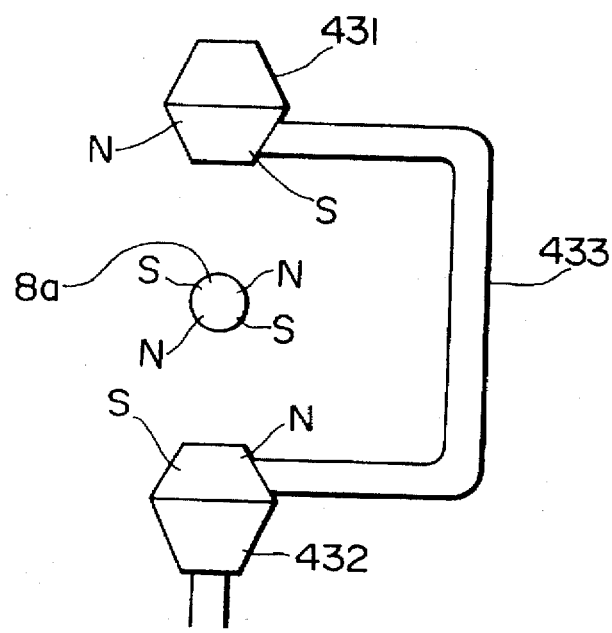
Figure 54:
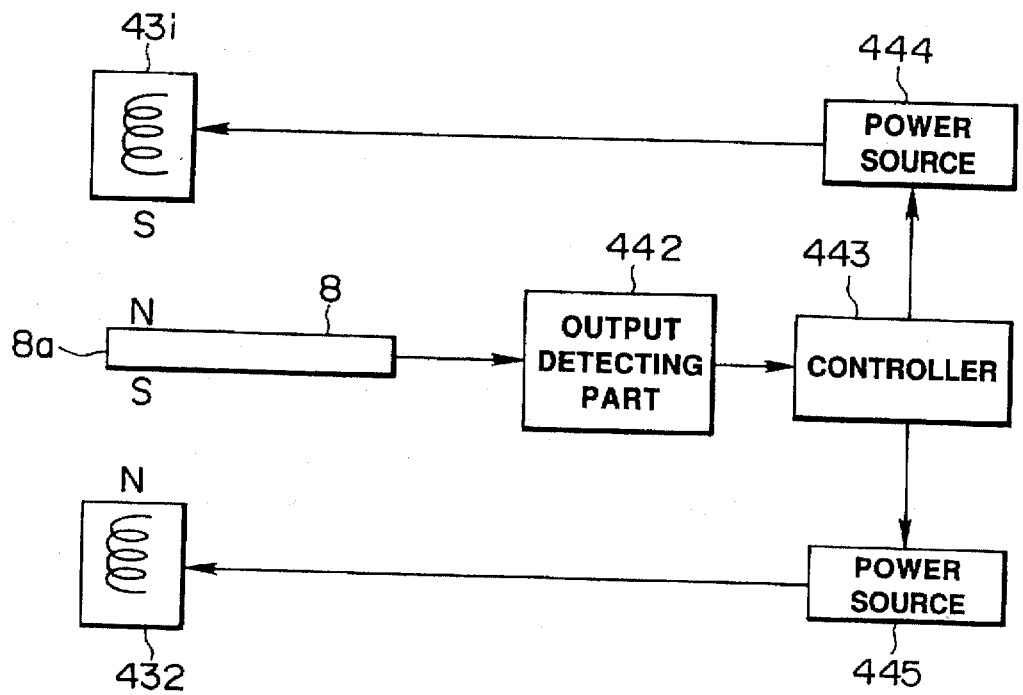

Also, as shown in FIG. 53, the electromagnets may be provided so that the magnetic poles in the tip part 8a may be turned, for example, at intervals of 90 degrees in the peripheral direction and that both N and S poles may appear respectively on the side opposed to the patient. The insertable part 8 may be guided so that the tip part 8a may be positioned in the position in which the gravity and the magnetic forces in the four directions between the heads 431 and 432 and the tip part 8a are balanced with each other.

Further, as required, the switch 435 is operated to change the polarities of the heads 431 and 432, the passage of the current through the coils of the electromagnets of the respective heads 431 and 432 is switched on/off and the current for the coils of the electromagnets of the respective heads 431 and 432 is varied to independently adjust the magnetic forces by the respective heads 431 and 432 to control the guidance of the inserted part 8.

Thus, according to this embodiment, the tip part 8a of the insertable part 8 can be guided accurately and positively to any position in the X, Y and Z directions while the tip part 8a is held in the position in which the force acting on this tip part 8 is balanced at least in one direction. Therefore, the insertable part 8 can be guided as desired into a complicatedly bent body cavity. In FIG. 52 is shown an example of a large intestine as a bent body cavity in a human body. The bent parts A to D in this view are not hard. When the insertable part 8 is merely pushed in to be inserted, the intestine will extend, this bent part will not be able to be passed over and the patient will be pained very much..

Futher, according to this embodiment, as the tip part 8a is not pulled so as to bite into the body cavity wall, the tip part 8a is easy to guide to the deep side within the body cavity and is safe.

Also, as the insertable part 8a is guided by generating repulsions respectively between the heads 431 and 432 and the tip part 8a, there will be no fear of holding the living body tissue between the heads 431 and 432 and the tip part 82 with a strong attraction and the safety will be high.

By the way, the means for generating a magnetic field from the heads 431 and 432 and the means for generating a magnetic field from the tip part 8a may be of a permanent magnet or electromagnet.

By the way, though not illustrated, the position within the body cavity is sensed by using X-rays or ultrasonic waves.

Figure 55:
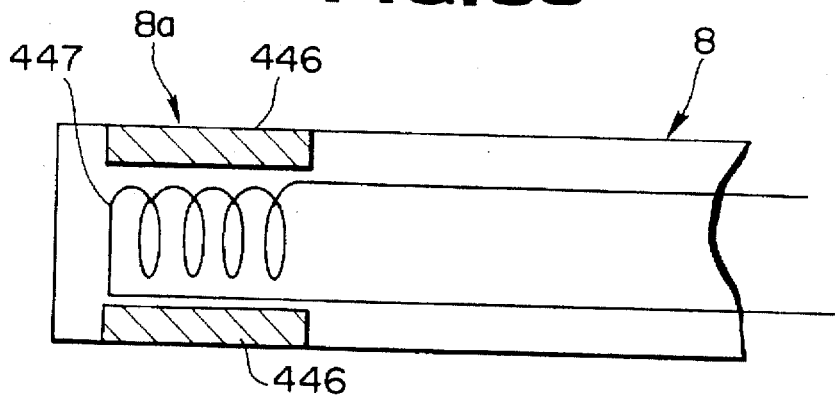
Figure 56:
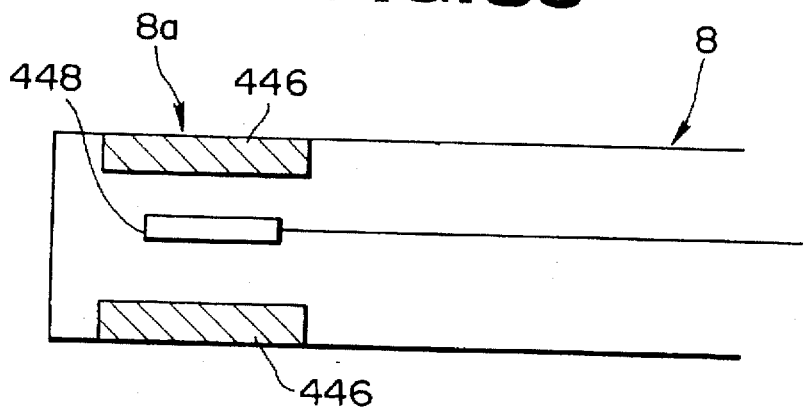

Now, in case attractions are generated respectively between the heads 431 and 432 and the tip part 8a, the forces acting on the tip part 8a are balanced and the insertable part 8 is guided in such state, the tip part 8a will be likely to deviate from the balancing position. Therefore, it is desirable to sense that the tip part 8a has deviated from the balancing position and to return the tip part 8a to the balancing position. As shown, for example, in FIG. 54, a sensor detecting the variation in the magnetic field is provided within the tip part 8a, the output of this sensor is detected by an output detecting part 412, power sources passing a current through the electromagnets of the respective heads 431 and 432 are controlled by a controller 443 on the basis of the output of this sensor and the magnetic forces by the respective heads 431 and 432 are adjusted to hold the tip part 8 in the balancing position. Said sensor may be such coreless coil 447 as is shown in FIG. 55 or such hall device 448 as is shown in FIG. 56. By the way, in FIGS. 55 and 56, the reference numeral 446 represents a magnet forming the tip forming part 29 or the like.

Figure 57:
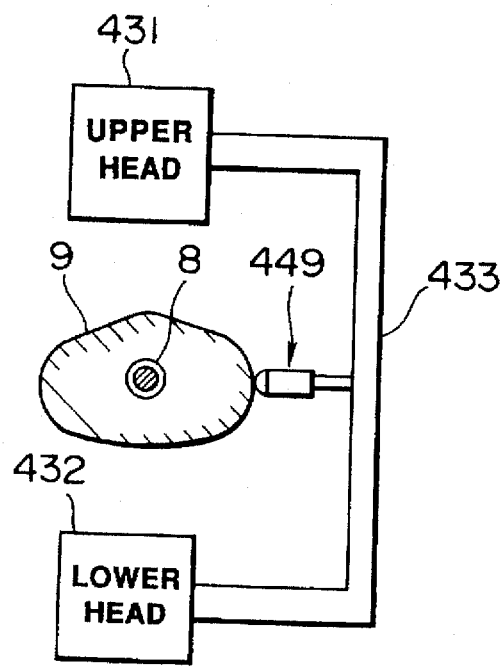

Also, as shown in FIG. 57, an ultrasonic probe 449 for confirming the position of the tip part 8a may be fitted to an arm 433. This ultrasonic probe 449 transmits and receive ultrasonic waves to measure the position of the tip part 8a. The positions of the heads 431 and 432 are adjusted and the magnetic forces by the respective heads 431 and 432 are adjusted so that the position of the tip part 8a measured by this ultrasonic probe 449 may be the position in which the forces acting on the tip part 8a are balanced.

Also, an ultrasonic wave oscillator may be provided in the tip part 8a so that ultrasonic waves issued from this ultrasonic wave oscillator may be received by an ultrasonic wave receiver outside the body to measue the position of the tip part 8a.

A hall device for detecting the magnetic field by the magnet provided in the tip part 8a to measure the position of the tip part 8a may be provided instead of the ultrasonic probe.

Figure 58:
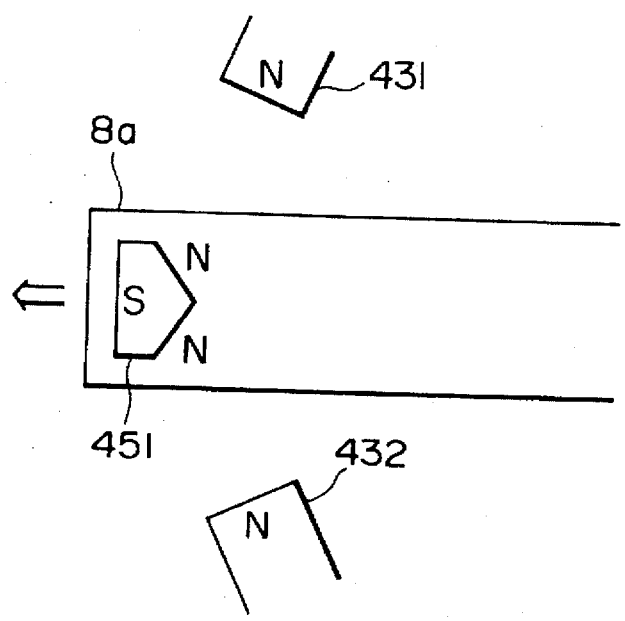

On the other hand, in case repulsions are generated respectively between the heads 431 and 432 and the tip part 8a, the forces acting on the tip part 8a are balanced and the insertable part 8 is guided in such state, the insertability will improve as in the following. That is to say, as shown in FIG. 58, within the tip part 8a, a magnet 451 in which magnetic poles, for example, N poles are generated in the obliquely upward and obliquely downward directions is provided on the rear end side and, in the upper head 431 and lower head 432, N poles are generated in the oblliquely forward directions respectively on the patient side. The heads 431 and 432 are arranged somewhat rearward with respect to the tip part 8a. When the heads 431 and 432 are moved forward from this state, the tip part 8a will be able to be advanced forward by the repulsions while being held in the balancing position in the vertical direction.

Figure 59:
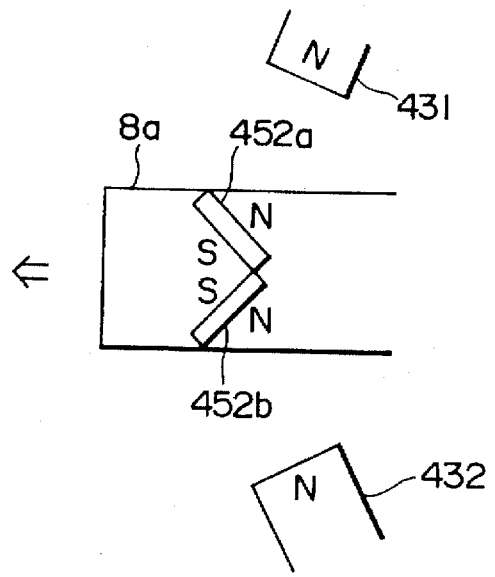

As shown in FIG. 59, instead of said magnet 451, a magnet 452a generating a magnetic pole (for example, an N pole) in the obliquely upward direction and a magnet 452b generating a magnetic pole (for example, an N pole) may be provided on the rear end side.

Figure 60:
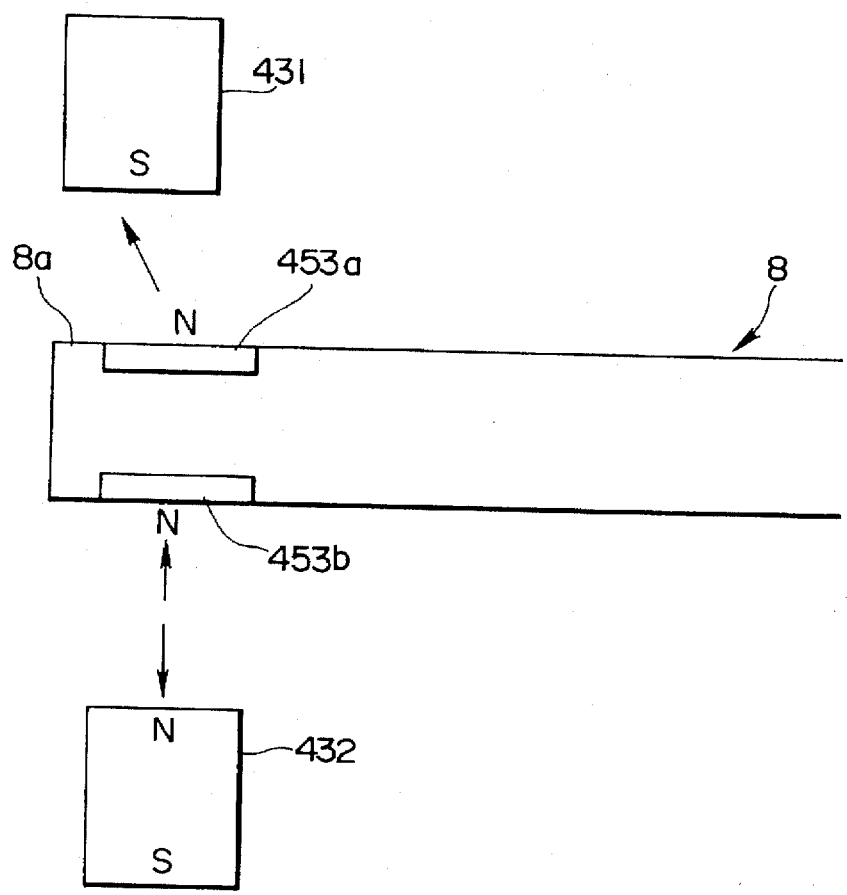

Also, as shown in FIG. 60, the upper head 431 is arranged somewhat more forward in the inserting direction than the lower head 432, a repulsion is generated between a magnet 453b on the lower side of the tip part 8a and the lower head 432, an attraction is generated between a magnet 453a on the upper side of the tip part 8a and the upper head 431 and, while the tip part 8a is held in the position in which said two magnetic forces and the gravity acting on the tip part 8a are balanced in the vertical direction, the tip part 8a may be pulled by the attraction by the upper head 431 to guide the insertable part 8.

Instead of the magnet 453a on the upper side of the tip part 8a, a ferromagnetic substance may be provided so that the tip part 8a may be pulled by the attraction acting between it and the upper head 431.

The 24th embodiment of the present invention shall be explained in the following by using FIG. 27.

This embodiment is an example of a capsule type endoscope the same as in the 11th and 16th embodiments. The formations of the capsule type endoscope 150 and control apparatus 160 are the same as in the 11th or 16th embodiment.

In this embodiment, the same as in the 23rd embodiment, a magnetic field is generated from the magnetic force generating apparatus 411, a magnetic force is generated between this magnetic force generating apparatus 411 and the permanent magnet 159 of the capsule type endoscope 150 and, while the capsule type endoscope 150 is held in the position in which the forces acting on the capsule type endoscope 150 balance in the vertical direction, the magnetic force generating apparatus 411 will be moved to guide the capsule type endoscope 150.

By the way, when said guided part 159 is of a permanent magnet which becomes all the same magnetic pole on the outer peripheral side and the magnetic poles generated on the patient side by the respective upper and lower heads 431 and 432 are made the same, the capsule type endoscope 150 will be prevented from rotating.

By the way, within the capsule body 151, instead of such components necessary for the observation as said objective lens 152, CCD 153 and LED 154, such sensors as a pH sensor and temperature sensor may be provided to detect a pH within the stomach, pH within the intestine and temperature. Also, within the capsule body 151, a collecting means for collecting an intestine liquid or the like or a medicine administering means may be provided.

The other formations, operations and effects are the same as in the 23rd embodiment.

By the way, in the 23rd or 24th embodiment, a plurality of magnetic force generating parts may be provided in the horizontally opposed positions with the guided part of the insertable part held between them.

The 23rd or 24th embodiment can be applied not only to an endoscope but also to a catheter and to an electronic endoscope provided with a solid state imaging device in the tip part of the insertable part.

Now, in case the insertable part 8 of the endoscope is inserted into a body cavity and then this insertable part 8 is to be magnetically guided, at first, the position of the tip part of the insertable part 8 will not be found. Therefore, two embodiments in which the position of the tip part of the insertable part 8 can be confirmed before the insertable part 8 is magnetically guided shall be shown in the following.

Figure 61:
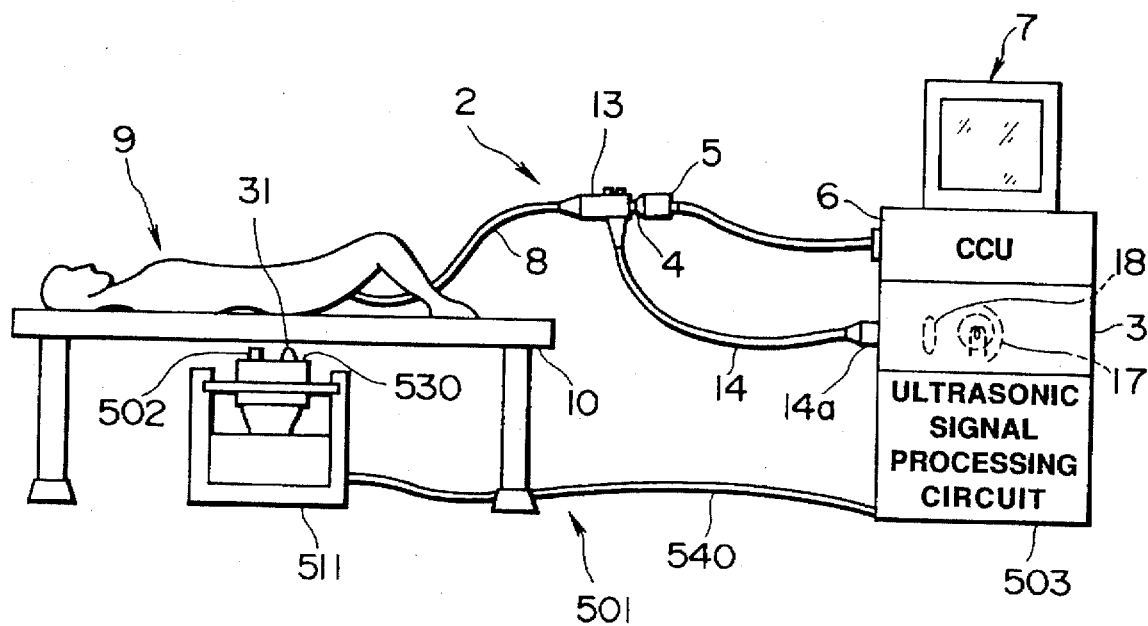
FIGS. 61 and 62 relate to the 25th embodiment of the present invention.
Figure 62:
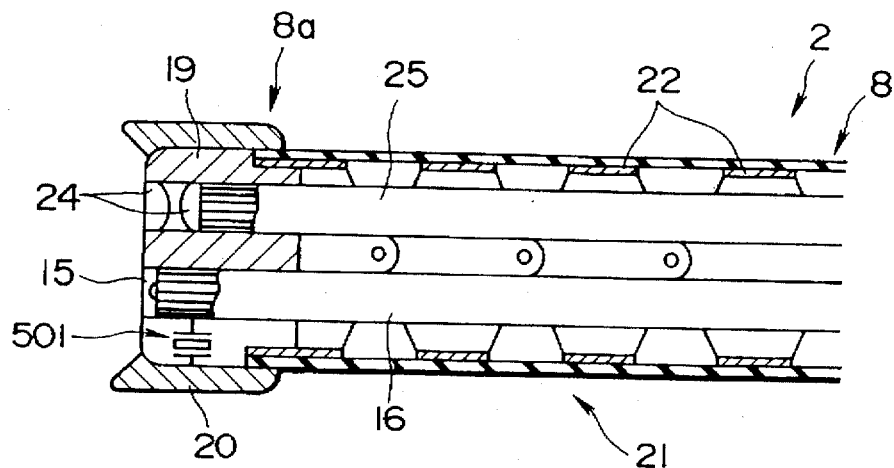

FIGS. 61 and 62 show the 25th embodiment of the present invention.

In an endoscope apparatus 501 of this embodiment, a magnetic force generating apparatus 511 is provided below a bed 10 and has a stage 530 which is movable in a horizontal plane and on which are provided a magnetic force generating part 31 made of an electaromagnet and a receiving ultrasonic wave oscillator 502 connected to an ultrasonic signal processing circuit 503 through a cable 540. The moving mechanism of said stage 230 is the same as the moving mechanism of the magnetic force generating part 31 in the first embodiment.

On the other hand, as shown in FIG. 62, a transmitting ultrasonic wave oscillator 501 is provided within the tip part 8a of the insertable part 8 of the endoscope 2. At least one of the tip part body 19 and hood 20 is formed of a permanent magnet or ferromagnetic substance.

The other formations are the same as in the first embodiment.

In this embodiment, ultrasonic waves are transmitted from the transmitting ultrasonic wave oscillator 501 provided within the tip part 8a and are received by the receiving ultrasonic wave oscillator 502 provided in the magnetic force generating apparatus 511. This receiving ultrasonic wave oscillator 502 is moved in the horizontal plane and the position in which the level of the received signal is the highest is detected by the ultrasonic signal processing circuit 503 to detect the position of the tip part 8a. The magnetic force generating part 531 is positioned in the position of this tip part 8a and then a magnetic field is generated from the magnetic force generating part 531 to magnetically guide the insertable part 8.

By the way, instead of said magnetic force generating apparatus 511, the magnetic force generating apparatus 411 of the 23rd embodiment may be used.

The other operations and effects are the same as in the first embodiment.

Figure 63:
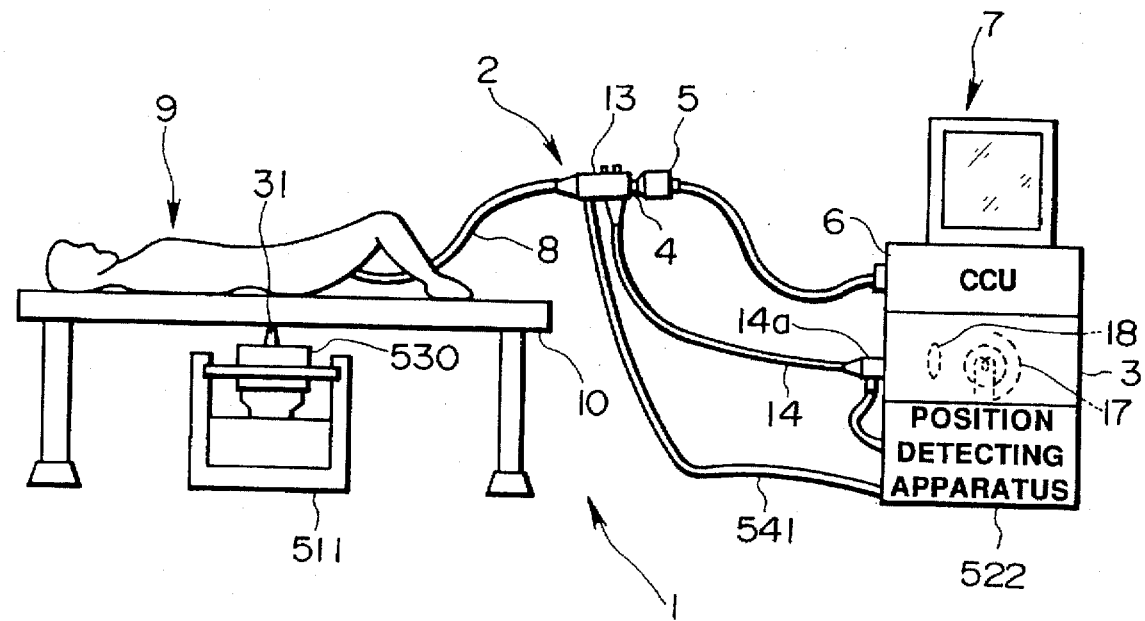
FIGS. 63 and 64 relate to the 26th embodiment of the present invention.
Figure 64:
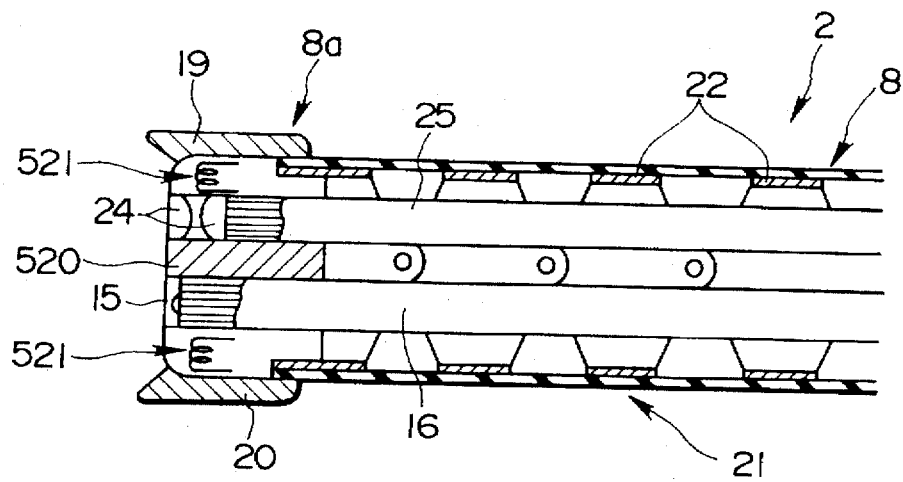

FIGS. 63 and 64 show the 23rd embodiment of the present invention.

In this embodiment, a magnetic force generating apparatus 511 is provided below a bed 10 and has a stage 530 which is movable in a horizontal plane and on which is provided a magnetic force generating part 31 made of an electromagnet.

On the other hand, as shown in FIG. 64, within a tip part 8a of an insertable part 8 of an endoscope 2, a permanent magnet 520 is provided on the center axis and at least two coreless coils 521 are provided in the positions different in the peripheral direction on the outer peripheral side. The signal lines connected to these coreless coils 521 are connected to a position detecting apparatus 522 through the insertable part 8 and cable 541.

The other formations are the same as in the first embodiment.

In this embodiment, when a magnetic field is generated from the magnetic force generating part 31 of the magnetic force generating apparatus 511 and this magnetic force generating part 31 is moved in a horizontal plane to approach the position of the permanent magnet 520 within the tip part 8a, a magnetic flux will cross the coreless coil 521, therefore an induced voltage will be generated in the coreless coil 521 and the position of the tip part 8a will be able to be detected by detecting this induced voltage with the position detecting apparatus 522. That is to say, the relative position relation with the magnetic force generating, part 31 can be known by reading with the position detecting apparatus 522 the level of the induced voltage generated in the coreless coil 521. In this case, the magnetic force generating part 31 is moved below the patient 9 and the peak of the induced voltage is sought. If the magnetic force generating part 531 is stopped in the position of this peak, it will be found that the tip part 8a is positioned in the position of the patient corresponding to it. After the magnetic force generating part 31 is positioned in the position of this tip part 8a, a magnetic field is generated from the magnetic force generating part 31 and the insertable part 8 is magnetically guided.

By the way, instead of said magnetic force generating apparatus 511, the magnetic force generating apparatus 411 of the 23rd embodiment may be used.

Now, in case a permanent magnet or ferromagnetic substance is provided in the tip part of the insertable part of such body cavity inserting instrument as an endoscope and the insertable part is magnetically guided by a magnetic field generated from outside the body, a stationary magnetic field of a fixed magnetic pole has been used. Therefore, the tip part of the insertable part has been pressed against the body cavity inside wall by the magnetic force and a friction force has been generated to prevent the advance of the insertable part in the case of guiding the insertable part.

Therefore, three embodiments in which the insertability of the insertable part can be improved shall be shown in the following.

FIGS. 65 to 72 show the 27th embodiment of the present invention.

Figure 65:
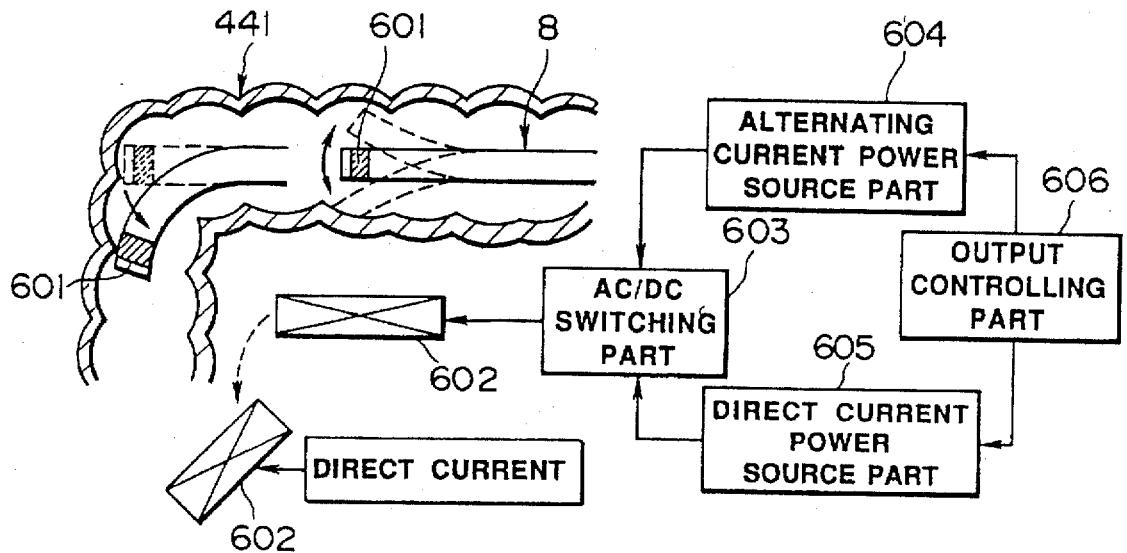
FIGS. 65 to 72 relate to the 27th embodiment of the present invention.
Figure 66:
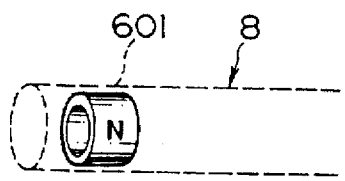

In this embodiment, as shown in FIG. 65, a cylindrical permanent magnet 601 is provided in the tip part of the insertable part 8 of an endoscope. As shown in FIG. 66, this permanent magnet 601 is of an N pole on the outer peripheral surface and an S pole on the inner peripheral surface. By the way, on the contrary, it may be of an S pole on the outer peripheral surface and an N pole on the inner peripheral surface.

The other formations of the endoscope are the same as in the 23rd embodiment.

On the other hand, an electromagnetic coil 602 is provided outside the body. As shown in FIG. 65, this electromagnetic coil 602 is connected to an alternating current power source part 604 and direct current power source part 605 through an AC/DC switching part 603. Both power source parts 604 and 605 are to be controlled in the output by an output controlling part 606.

In this embodiment, by said AC/DC switching part 603, an alternating curent from the alternating current power source part 604 and a direct current from the direct current power source part 605 can be selectively fed to the electromagnetic coil 602.

Figure 67:
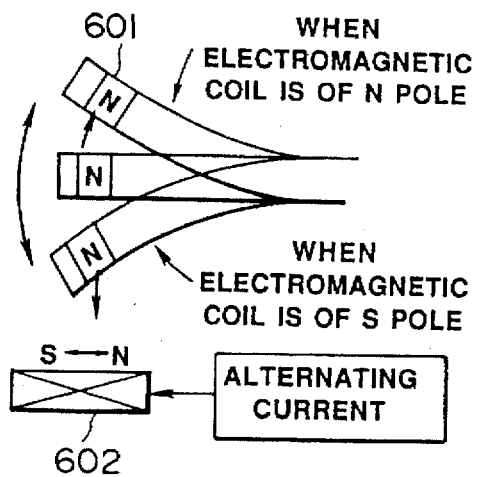

When said electromagnetic coil 602 is brought near to the permanent magnet provided in the tip part of the insertable part 8 and an alternating current (of about 1 to 10 Hz) is fed to the electromagnetic coil 602, an alternating magnetic field will be generated from this electromagnetic coil 602. As shown in FIG. 67, when the magnetic pole on the insertable part 8 side of the electromagnetic coil 602 is an N pole, a repulsion will be produced between this electromagnetic coil 602 and the permanent magnet 601 and the tip part will move in the direction of separating from the electromagnetic coil 602. On the other hand, when the magnetic pole on the insertable part 8 side of the electromagnetic coil 602 is an S pole, an attraction will be produced between this electromagnetic coil 602 and the permanent magnet 601 and the tip part will move in the direction of approaching the electromagnetic coil 602. Therefore, if an alternating current is fed to the electromagnetic coil 602, the tip part will vibrate.

Figure 68:
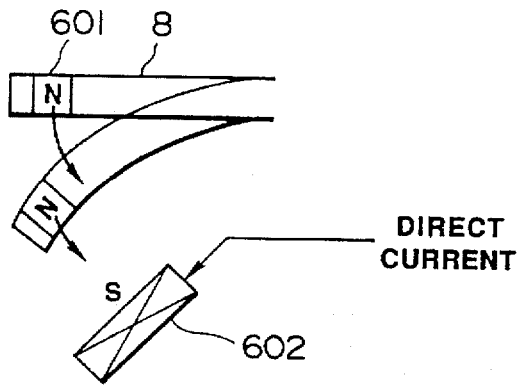

Also, when said electromagnetic coil 602 is brought near to the permanent magnet provided in the tip part of the insertable part 8 and a direct current is fed to the electromagnetic coil 602, as shown in FIG. 68, a magnetic force of an attraction or repulsion will be produced between this electromagnetic coil 602 and the permanent magnet 601. The insertable part 8 can be guided by this magnetic force.

As shown in FIG. 65, in case the insertable part 8 is to be inserted into such bent inspected object as, for example, a large intestine 441, in the straight part of the large intestine 441, an alternating current will be fed to the electromagnetic coil 602 to vibrate the tip part of the insertable part 8 so that the contact resistance between the insertable part 8 and the inside wall of the large intestine 441 may reduce. In this state, the operator inserts the insertable part 8 by a pushing operation. On the other hand, when the tip part of the insertable part 8 reaches the bent part of the large intestine 441, the electromagnetic coil 602 will be arranged in a predetermined position in the advancing direction, a direct current will be fed to this electromagnetic coil 602 and the tip part will be bent in the advancing direction by an attraction so that the tip part of the insertable part 8 may pass through the bent part of the large intestine 411.

The moving mechanism of said electromagnetic coil 602 shall be explained in the following by using FIGS. 69 to 72.

Figure 69:
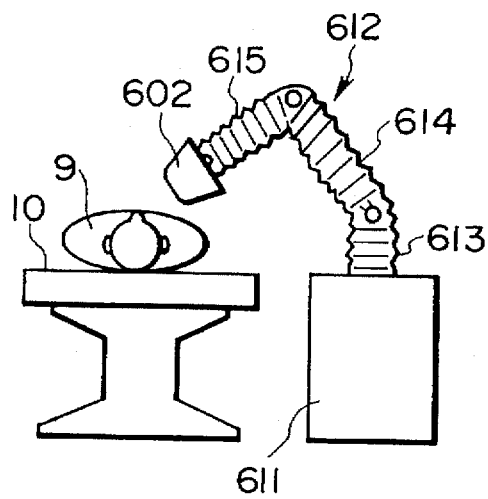
Figure 70:
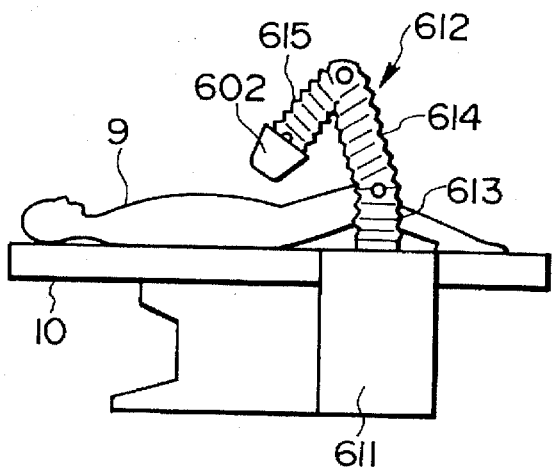

As shown in FIGS. 69 and 70, a console 611 is provided on the side of a bed 10 on which is mounted a patient 9, a driving arm 612 is fitted on this console and an electromagnetic coil 602 is fitted to this driving arm 612 at the end. Said driving arm 12 is formed of a supporting part 613 erected on said console 11, a first arm part 614 rotatably connected to this supporting part 613 at the upper end and a second arm part 615 rotatably connected to this first arm part 614.

Figure 71:
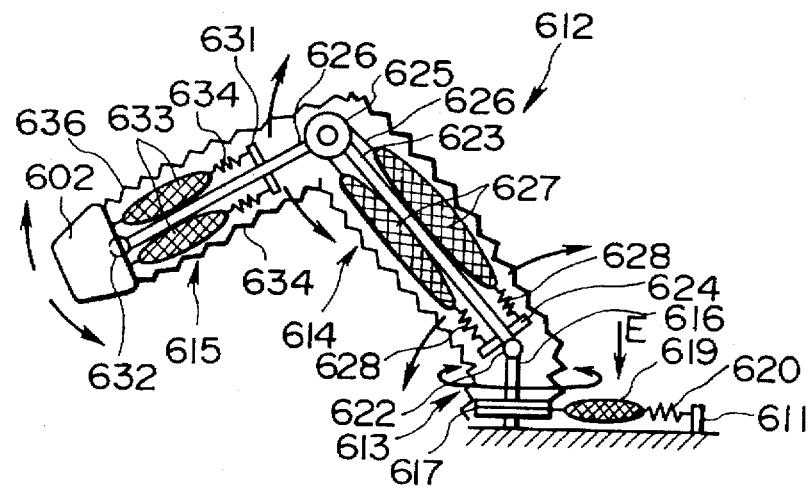
Figure 72:
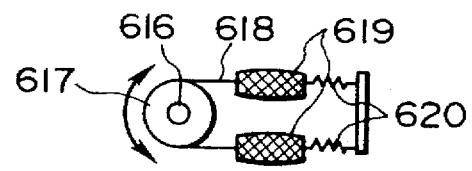

As shown in FIG. 71, said supporting part 613 has a shaft 616 which is rotatably fitted on the console 611 and to which is fitted a pulley 617. As shown in FIG. 72, a wire 618 is wound on this pulley 617 and is fixed at both ends on the console 611 respectively through rubber artificial muscles 619 and coil springs 620.

A shaft 623 of the first arm part 614 is rotatably connected to said shaft 616 at the upper end through a hinge 622, is provided with a flance 624 at the end on the hinge 622 side and is fitted with a pulley 625 at the end on the side opposite the hinge 622. A shaft 626 of the second arm part 615 is connected to a rotary shaft of this pulley 625. A wire 626 is wound on said pulley 626 and is fixed at both ends to said flange 624 respectively through rubber artificial muscles 627 and coil springs 628.

A flange 631 is provided at the end on the pulley 625 side of the shaft 626 of said second arm part 615. An electromagnetic coil 602 is rotatably connected through a hinge 632 to said shaft 626 at the end on the side opposite the pulley 625. This electromagnetic coil 602 is fitted with rubber artificial muscles 633 respectively at the ends in the positions opposed to each other with said hinge 632 between them and these rubber artificial muscles 633 are fixed at the other ends to said flange 631 respectively through coil springs 634. The supporting part 613, first arm part 614 and second arm part 615 are covered on the outer periphery with an accordion type cover 636.

An air pressure controlling part and compressor are connected to said respective rubber artificial muscles 619, 627 and 633 through pressurizing air tubes not illustrated so that pressurized air may be fed to the respective rubber artificial muscles 619, 627 and 633. When charged with presssurized air, the respective rubber artificial muscles 619, 627 and 633 will contract. Therefore, when the pressurized air fed to the rubber artificial muscles 619 is controlled, the shaft 616 of the supporting part 613 will rotate. When the pressurized air fed to the rubber artificial muscles 627 is controlled, the shaft 626 of the second arm part 615 will rotate. When the pressurized air fed to the rubber artificial muscles 633 is controlled, the electromagnetic coil 602 will be rotated. Thus, by driving the arm 612, the electromagnetic coil 602 can be positioned in any position.

Figure 73:
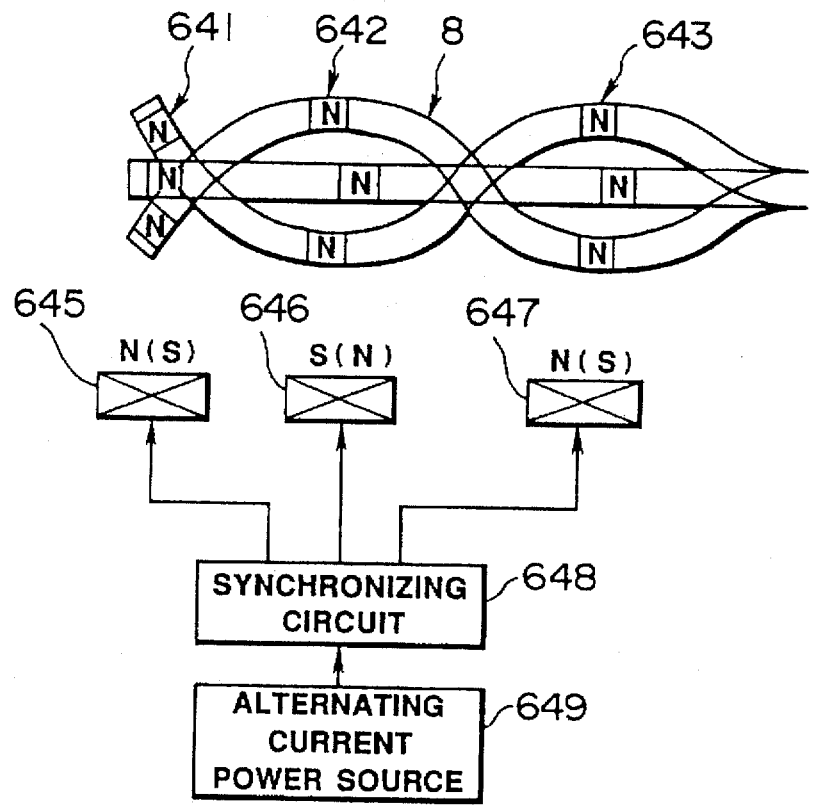
FIGS. 73 and 74 relate to the 28th embodiment of the present invention.
Figure 74:
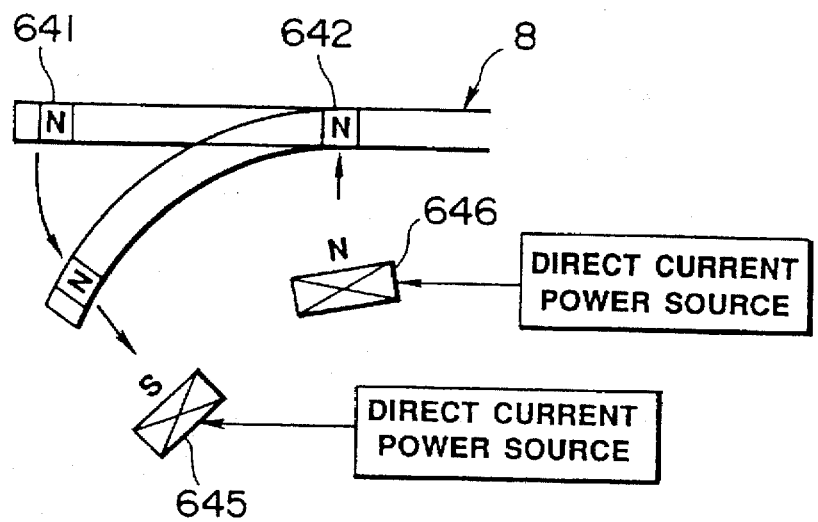

FIGS. 73 and 74 show the 28th embodiment of the present invention.

In this embodiment, permanent magnets 641, 642 and 643 are provided at predetermined intervals in the axial direction in the insertable part 8 of an endoscope. Each permanent magnet is of an N pole on the outer peripheal side and an S pole on the inner peripheral side. Electromagnetic coils 645, 646 and 647 corresponding to the respective permanent magnets 641, 642 and 646 are provided outside the body. An alternating current power source 649 is connected to the respective coils 645 to 647 through a synchronizing circuit 648.

In this embodiment, a synchronized alternating current is fed to the respective coils 645 to 647 through the synchronizing circuit 648 from said alternating current power source 649. The respective adjacent ones of the coils 645 to 647 are to produce magnetic poles opposite to each other. Therefore, when an alternating current is fed to the respective coils 645 to 647, as shown in FIG. 73, the insertable part 8 will vibrate (jiggle) like waves so that the contact resistance between the insertable part 8 and the inside wall of the large intestine 441 or the like may reduce.

By the way, when the direction of the tip side of the insertable part 8 is to be changed in the bent part or the like of the large intestine, as shown in FIG. 74, if direct current power sources are connected respectively to the electromagnetic coils 645 and 646 so that an attraction may be generated between the coil 645 and permanent magnet 641 and a repulsion may be generated between the coil 644 and permanent magnet 642, the insertable part 8 will be able to be bent efficiently at a sharp angle.

By the way, the driving mechanism of the coils 345 to 347 may be, for example, the driving mechanism of the magnetic force generating part in the sixth embodiment.

Figure 75:
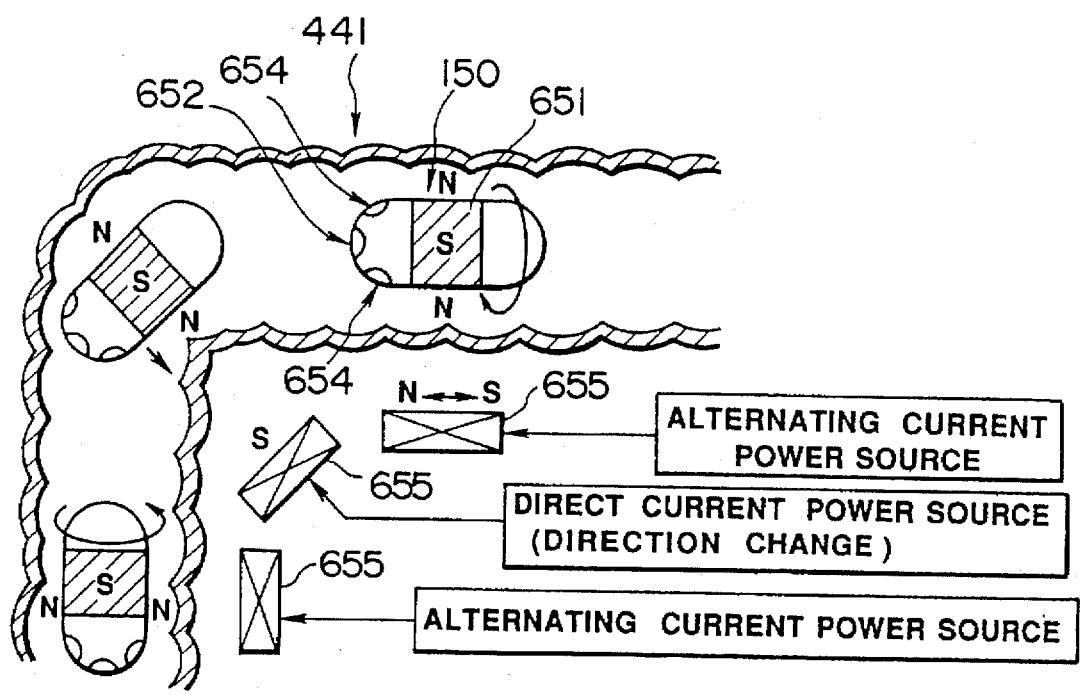

FIGS. 75 and 76 show the 29th embodiment of the present invention.

Figures 76A, 76B:
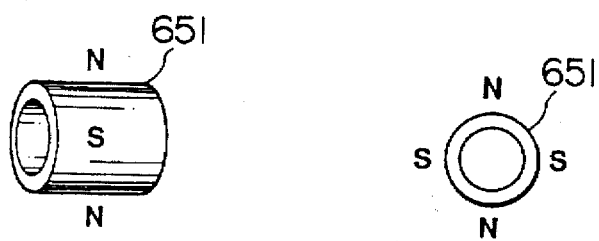
FIG. 76(A) is a perspective view showing a permanent magnet to be provided in a capsule type endoscope.
FIG. 76(B) is an elevation of a permanent magnet.

The endoscope in this embodiment is the same capsule type endoscope 150 as in the 11th embodiment. A ring-like permanent magnet 651 is provided on the outer periphery of this capsule type endoscope 150 and has the magnetic poles on the outer periphery turned at intervals of 90 degrees as shown in FIGS. 76(A) and (B). By the way, in FIG. 75, the reference numeral 652 represents an observing window and 654 represents an illuminating window. The other formations of the capsule type endoscope 150 are the same as in the 11th embodiment.

Also, a magnetic coil 655 for magnetically guiding said capsule type endoscope 150 is provided outside the body.

In this embodiment, in case the capsule type endoscope 150 is to be guided in the straight part of the large intestine 441, an alternating current power source will be connected to the electromagnetic coil 655 so that an alternating magnetic field may be generated from the electromagnetic coil 655. Then the capsule type endoscope 150 will make a rotary or reciprocating rotary motion with the axis as a center so that the capsule type endoscope 150 may be guided while the contact resistance between it and the inside wall of the large intestine 441 is being reduced. When the direction of the capsule type endoscope 150 is to be changed in the bent part or the like of the large intestine 441, a direct current power source will be connected to the electromagnetic coil 655 so that a stationary magnetic field may be generated from the electromagnetic coil 655. Then an attraction will be generated between this electromagnetic coil 655 and capsule type endoscope 150 and will be able to be used to change the direction of the capsule type endoscope 150.

By the way, the driving mechanism of said coil 655 may be, for example, the driving mechanism of the magnetic force generating part in the first embodiment or the driving mechanism of the coil in the 27th embodiment.

Figure 77:
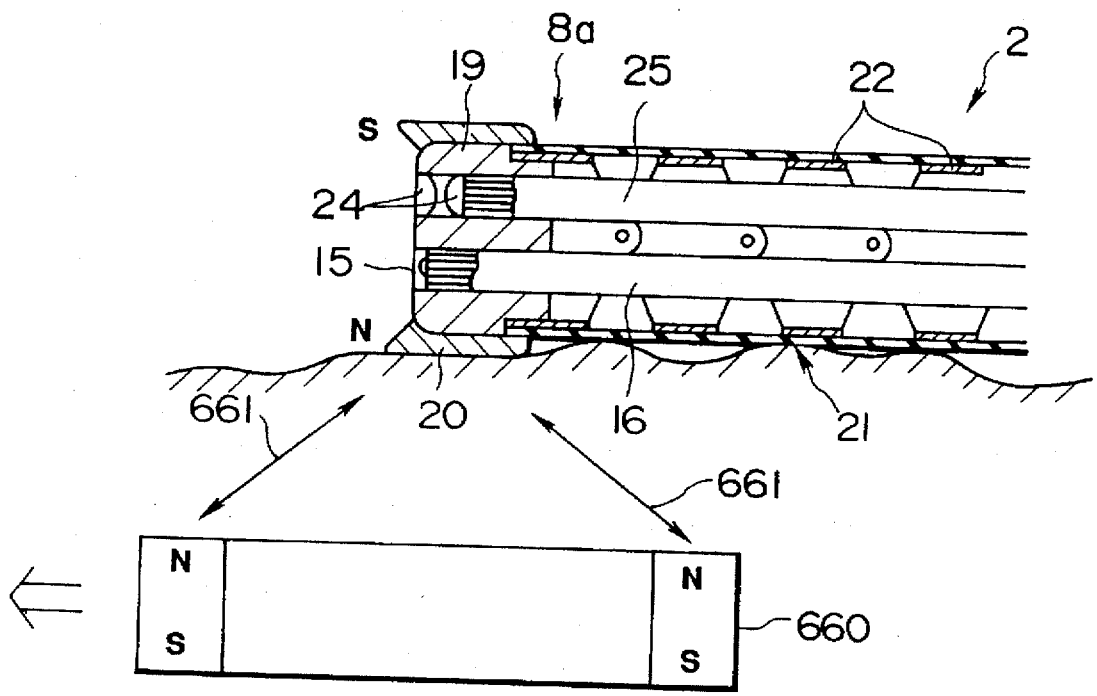
FIGS. 77 and 78 relate to the 30th embodiment of the present invention.
Figure 78:
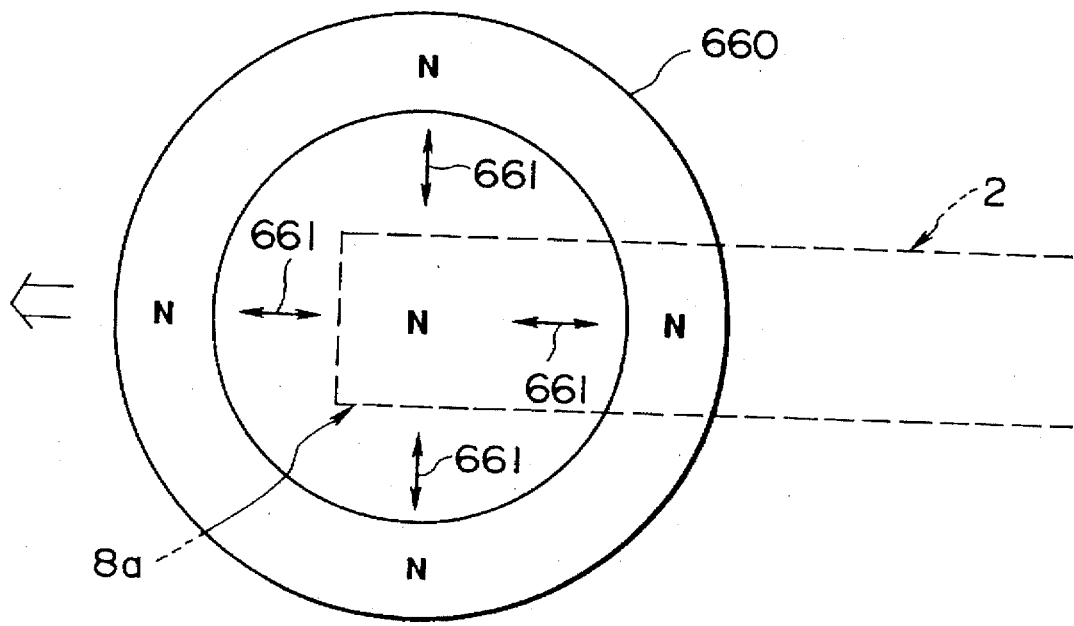

FIGS. 77 and 78 show the 30th embodiment of the present invention.

The formation of the endoscope apparatus of this embodiment is substantially the same as in the first embodiment but is different in respect of using a ring-like permanent magnet 660 for the magnetic force generating part 31 of the magnetic force generating apparatus 11. As shown in the drawings, this permanent magnet 660 has a diameter larger than of the end part 8a of the endoscope 2 and is, for example, of an N pole on the upper side and an S pole on the lower side. The tip part body 19 of the tip part 8a of this endoscope 2 or a hood 20 is of a permanent magnet, for example, of an S pole on the upper side and an N pole on the lower side.

In case the endoscope 2 is to be guided within an inspected object, as shown in the drawings, the permanent magnet 660 will be arranged so that the tip part 8a of the endoscope 2 may come substantially to the central part of the permanent magnet 660. The permanent magnet 660 will be moved in the advancing direction of the endoscope 2 from this state. As the magnetic force (repulsion) by the permanent magnet 660 acts on the tip part 8a in all the horizontal direction, the tip part 8a will be held in the position in which said magnetic force acting on this tip part 8a will balance in the horizontal direction, that is, in the central part of the permanent magnet 660. Therefore, the tip part 8a can be guided in conformity with the movement of the permanent magnet 660 while the tip part 8a is held in the central part of the permanent magnet 660.

According to this embodiment, the guided part can be prevented from deviating from the position of the outside guiding part.

As an upward force also acts on the guided part, the friction force between the tip part 8a and the inspected object will be reduced.

The other formations, operations and effects are the same as in the first embodiment.

Thus, according to the 23rd, 24th and 30th embodiments, there is an effect that, as the inserted body can be guided while the force acting on the guided part of the inserted body is balanced in at least one direction, the guidance controllability in the case of magnetically guiding the inserted body will improve.

FIGS. 79(a) to 83 show the 31st embodiment of the present invention.

As shown in FIG. 79(a), an endoscope apparatus 701 of this embodiment comprises an endoscope 2 by a fiberscope (which may be an electronic scope) as an example provided with a magnetic substance in an insertable part insertable into an inspected object, a light source apparatus 3 for feeding an illuminating light to this endoscope 2, a TV camera 5 fitted to an eyepiece part 4 of the endoscope 2, a CCU 6 processing a signal for this TV camera 5, a TV monitor 7 inputting a video signal output from this CCU 6 and displaying an object image, a magnetic force generating apparatus 711 arranged on the upper side to the lower side of a bed 10 on which is placed a patient 9 into whom an insertable part 8 of the endoscope 2 is to be inserted and a controlling part 712 connected with this magnetic force generating apparatus 711. The formations and operations of said endoscope 2, light source apparatus 3, TV camera 5, CCU 6 and TV monitor 7 are the same as in the first embodiment.

In this embodiment, the magnetic force generating apparatus 711 arranged to insert the bed 10 comprises magnetic force generating parts 731A and 731B generating respectively guiding and vibrating magnetic forces below and above the bed 10 and moving mechanisms 732A and 732B respectively making said magnetic force generating parts 731A and 731B movable in horizontal planes.

Figure 80A:
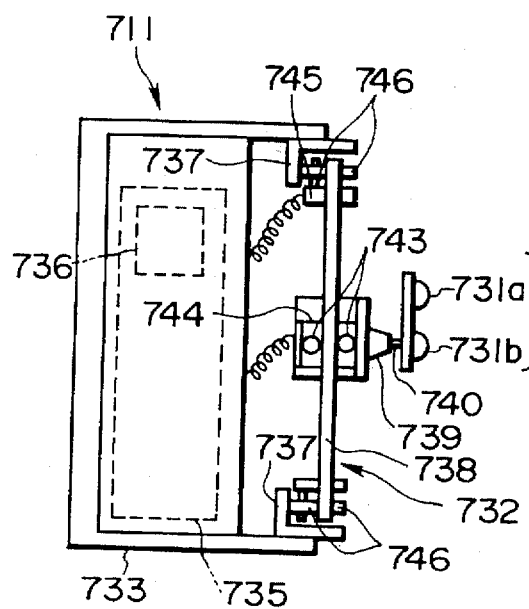
FIG. 80(A) is a side view of a magnetic force generating apparatus.
Figure 80B:
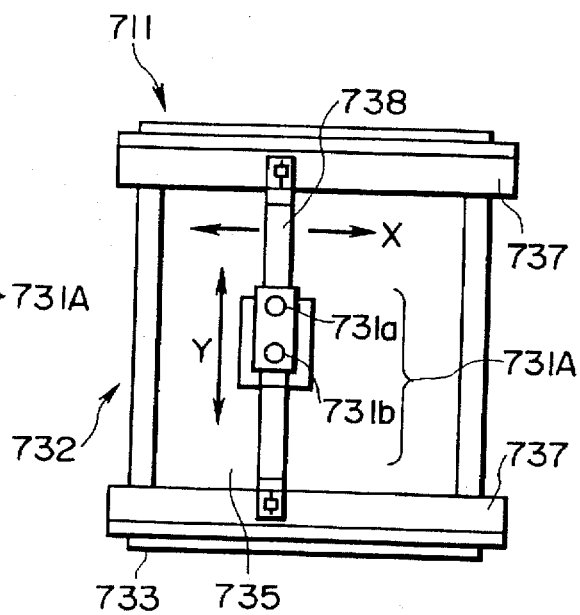
FIG. 80(B) is a plan view of the magnetic force generating apparatus.
Figure 81:
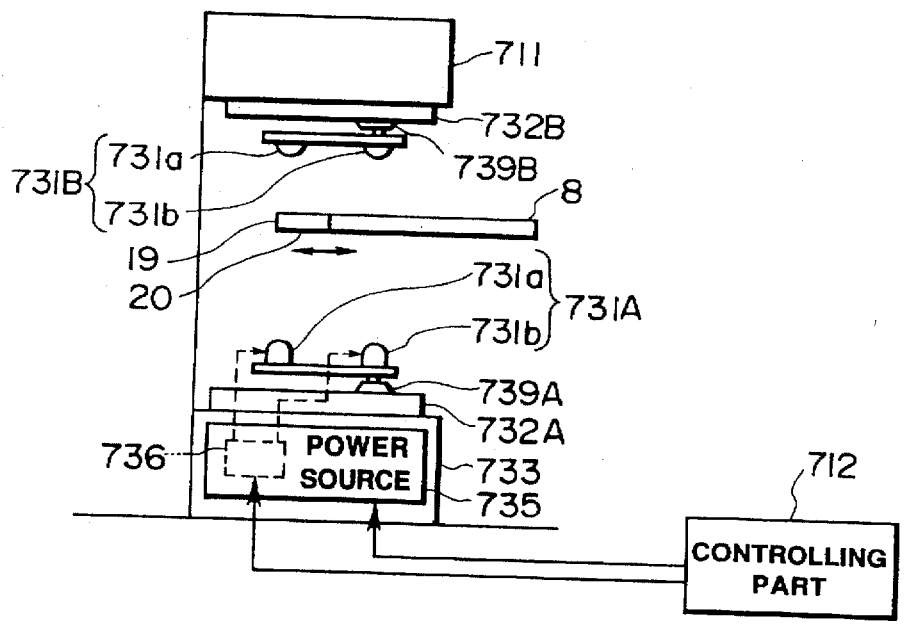

The formation of the essential part of this magnetic force generating apparatus 711 is shown in FIGS. 80(A) and (B).

In this magnetic force generating apparatus 711, a power source 735 for the respective guiding and vibrating magnetic force generating parts 731A and 731B and moving mechanisms 732A and 732B moving them is housed in the bottom within a chassis 733 opened on the uper side on the base side and is further provided with a vibration controlling apparatus 736 which can switch on/off the output electric power at a fixed frequency.

The moving mechanisms 732A and 732B are of the same formation and therefore only one formation shall be explained but the other formations shall not be explained here.

in the moving mechanism 732A, paired guide rails 737 are fitted to the upper end sides parallelly opposed to said chassis 733, a second guide rail 738 is provided in the direction (represented by Y) intersecting at right angles with the lengthwise direction (represented by X) of said guide rails 737 between these guide rails 737 and a direction rotating motor 739 is provided on this guide rail 738. Guiding parts 731a and 731b made of two electromagnets and provided as separated from each other for a fixed distance are fitted to a rotary shaft 740 of this direction rotating motor 739. These direction rotating motor 739 and guiding parts 731a and 731b are fitted movably in the lengthwise direction Y of said guide rail 738.

Said guiding parts 731a and 731b are fitted to the guide rail 738 through rotors 743 rotated by a motor 744.

Said guide rail 738 is mounted at one end on the guide rail 737 through a motor 745 and rotors 746 rotated by this motor 745.

Therefore, when the motor 745 is rotated, the rotors 746 will be rotated and the guide rail 738 will be able to be moved in the lengthwise direction X of the guide rail 737.

By the way, the motors 744 and 745 respectively rotating and driving said rotors 743 and 746 and the motor 739 are preferably ultrasonic motors not influenced by the magnetic force. Said motors 744, 745 and 739 can be rotated (normally and reversely and stopped) by a controlling part 712 connected through a cable 40. Thus, the guiding parts 731a and 731b can be moved and set in any position in a horizontal plane and can be directed in the advancing direction.

A vibration controlling apparatus 736 can feed an electric power alternately to said guiding parts 731a and 731b so that a magnetic field may be generated alternately from the guiding parts 731a and 731b.

The operation of this thus formed endoscope shall be explained in the following.

As shown in FIG. 83, the endoscope 2 is pushed into the large intestine 41. Then, while the endoscope of the TV monitor 7 is being observed, the upper and lower magnetic force generating parts 731B and 731A are moved in the horizontal position. In this case, if the horizontal positions of the magnetic force generating parts 731A and 731B are moved sequentially to the positions 750a, 750b, 750c and 750d shown by the broken lines along the bent tube cavity of the large intestine 41, the tip part body 19 or hood 20 made of a permanent magnet or ferromagnetic substance will be attracted by the magnetic force and therefore the tip part 8a will be moved to trace the moving course of the magnetic force generating parts 731A and 731B. In this case, when the movement of the tip part 8a has become dull, for example, in the bent part or the like of the large intestine, the vibration controlling apparatus 736 will be driven from the controlling part 712 and the electric power switched as shown in FIGS. 82(A) and (B) will be applied to the guiding parts 731a and 731b from said vibration controlling apparatus 736 so that a magnetic field will be generated alternately from the guiding parts 731a and 731b, therefore the magnetic substance provided in the tip part 89 will vibrate in the advancing direction according to the magnetic field and the tip part 89 will be vibrated. Thus, when the moved amount of the tip part 89 has become dull, if the tip part 89 is vibrated, the friction force between the tip part 89 and the intestine wall surface will be reduced and the movement of the endoscope 2 will be able to be made smooth.

Thus, the tip part 89 can be inserted into the deep side of the large intestine 41.

In the movement of the positions of said magnetic force generating parts 731A and 731B, by rotating the motors 744 and 745, the magnetic force generating parts 731A and 731B can be moved in the lengthwise direction Y of the guide rail 738, the guide rail 738 can be moved in the lengthwise direction X of the guide rail 737 and therefore the magnetic force generating parts 731A and 731B can be moved to any position in the horizontal plane. In fact, the endoscope tip part 19 is advanced while being attracted by the magnetic forces by the magnetic force generating parts 731A and 731B from the sides above and below the patient 9 and therefore can be slid on the large intestine wall surface (the large intestine wall surface between the tip part 89 and the magnetic force generating parts 318A and 318B.

According to this embodiment, the endoscope 2 can be easily inserted into such bent part as in the large intestine 41.

Here, an said embodiment, only the guiding parts 731a and 731b of the magnetic force generating part 731A on the lower side have been controlled by the vibration controlling apparatus 736 but the guiding parts 731a and 731b of the magnetic force generating part 731B on the upper side may be also synchronized and controlled.

By the way, in this embodiment, in case the shape of the tube cavity of the large intestine 41 which will be standard in the case of the body structure in response to the body structure of the patient 9 is displayed in the TV monitor 7 or on another monitor picture, the positions in the horizontal plane of the magnetic force generating parts 731A and 731b are also displayed as superimposed on this picture and the magnetic force generating parts 731A and 731B are moved, the positions in the horizontal plane of the magnetic force generating parts 731A and 731B corresponding to the position of the tube cavity will be easy to find so that the insertion may be easy.

In case the magnetic force generating parts 731A and 731B are moved, the relative positions or the like of the shape of the tube cavity of the large intestine 41 and the magnetic force generating parts 731A and 731B may be simultaneously corrected from the loci.

Further, the horizontal positions of the magnetic force generating parts 731A and 731B can be detected, for example, with encoders fitted to the motors 744 and 745.

Said magnetic force generating parts 731A and 731BA are made movable to the position to which the endoscope tip part 89 is pulled to slide on the wall surface and therefore can be formed of small electromagnets or the like.

On the endoscope side, as the tip part body 19 or the hood 20 fitted to this tip part body 19 is formed of a permanent magnet or ferromagnetic substance, the outside diameter of the insertable part need not be made substantially larger and the pain given to the patient can be reduced.

In the embodiments, for example, the following modifications can be made:

(1) The magnetic force generating means arranged outside the body may be of a permanent magnet. In such case, the magnetic force can be controlled by varying the distance to the endoscope.

(2) The electromagnet of the magnetic force generating means may be not only an ordinary electromagnet but also a superconductive magnet.

(3) The guided part provided in the endoscope itself may be of an electromagnet instead of a permanent magnet or ferromagnetic substance.

(4) The invention can be applied not only to the large intestine and small intestine endoscopes shown in the respective embodiments but also to:

Endoscopes for veins;

Catheters for digesting tubes and veins; Capsule type endoscopes and capsule type intestinal liquid collecting apparatus; and Capsule type medicine administering apparatus.

As described above, according to this embodiment, an endoscope provided in the tip part with a magnetic body and a magnetic force generating apparatus at least two-dimensionally movable around such insertion object as a patient are provided, the endoscope is moved by this magnetic force generating apparatus. the endoscope can be smoothly inserted by the magnetic force without making the diameter substantially larger and can be moved to slide on the tube wall, therefore the magnetic force generating means can be also made small, the magnetic force generating apparatus is driven by a vibration controlling apparatus so that the endoscope insertable part tip may vibrate and therefore the insertion is easy.

By the way, the electromagnets and coreless coils used in the above respective embodiments may be formed of superconductive materials.

It is apparent that, in this invention, working modes different in a wide range can be formed on the basis of this invention without deviating from the spirit and scope of the invention. This invention is not restricted by its specific working modes except being limited by the appended claims.

What is claimed is:

1. A combination of an insertable body and a guiding apparatus for guiding the insertable body within an inspected object comprising:

an insertable body to be inserted into an inspected object;

a guided part provided in at least a part of said insertable body and to be magnetically guided; and a guiding means outside said inspected object to be provided for magnetically guiding said guided part, said guiding means including a base, a first support connected to said base and which is movable in a first predetermined horizontal direction relative to said base, a second support connected to said first support and which is movable in a second predetermined horizontal direction relative to said base, said second predetermined horizontal direction being perpendicular to said first predetermined horizontal direction, a guiding part mounted on said second support for movement therewith for guiding said guided part, and a driving means for moving said first support and said second support relative to said base so as to move said guiding part, said guided part and said guiding part generating therebetween a magnetic force, and said guiding part guiding said guided part with said magnetic force.

2. A guiding apparatus according to claim 1, wherein said insertable body includes a means for obtaining information within said inspected object.

3. A guiding apparatus according to claim 1, wherein said insertable body includes a means for obtaining an optical image within said inspected object.

4. A guiding apparatus according to claim 1, wherein said insertable body is elongate and flexible.

5. A guiding apparatus according to claim 4, wherein said insertable body includes a tip part and said guided part is disposed in said tip part.

6. A guiding apparatus according to claim 1, wherein said guided part includes a ferromagnetic substance.

7. A guiding apparatus according to claim 1, wherein said guided part includes a permanent magnet.

8. A guiding apparatus according to claim 1, wherein said guided part includes an electromagnet.

9. A guiding apparatus according to claim 8, wherein said electromagnet has a coreless coil.

10. A guiding apparatus according to claim 1, wherein said guiding part includes means for generating a magnetic field.

11. A guiding apparatus according to claim 1, wherein said driving means includes at least a first motor for moving said first support relative to said base and a second motor for moving said second support relative to said first support, to move said guiding part in two dimensions.

12. A guiding apparatus according to claim 1, further comprising a position detecting means for detecting an at least two-dimensional position of said guided part within said inspected object.

13. A guiding apparatus according to claim 12, wherein said guiding part includes a magnetic field generating means for generating a magnetic field and said position detecting means includes a magnetic field detecting means for detecting said magnetic field generated by said magnetic field generating means to detect the position of said guided part.

14. A guiding apparatus according to claim 13, wherein said magnetic field detecting means has a Hall effect device.

15. A guiding apparatus according to claim 13, wherein said position detecting means further includes a means for two-dimensionally moving said magnetic field detecting means.

16. A guiding apparatus according to claim 13, wherein said magnetic field detecting means is provided near said guiding part and is moved together with said guiding part by said driving means.

17. A combination of an insertable body and a guiding apparatus for guiding the insertable body within an inspected object, comprising:

an insertable body to be inserted into an inspected object;

a guided part provided in at least a part of said insertable body, to be magnetically guided and including a coreless coil generating a magnetic field when an electric current is passed through the coil;

a current passing means for passing a current through said coreless coil;

a guiding means outside said inspected object for at least two-dimensionally and magnetically guiding said guided part, said guiding means including a base, a first support connected to said base and which is movable in a first predetermined horizontal direction relative to base, and a second support connected to said first support and which is movable in a second predetermined horizontal direction relative to said base, said second predetermined horizontal direction being perpendicular to said first predetermined horizontal direction, and a movable guiding part mounted on said second support for movement therewith for guiding said guided part, said guided part and guiding part generating a magnetic force acting therebetween, and said guiding part guiding said guided part with said magnetic force.

18. A combination of an insertable body and a guiding apparatus for guiding the insertable body within an inspected object, comprising:

an insertable body to be inserted into an inspected object;

a guided part to be magnetically guided, provided in at least a part of said insertable part and including a magnetic field generating means for generating a magnetic field;

a guiding means for at least two-dimensionally and magnetically guiding said guided part and provided outside said inspected object, said guiding means including a base, a first support connected to said base and which is movable in a first predetermined horizontal direction horizontal relative to said base, a second support connected to said first support and which is movable in a second predetermined horizontal direction relative to said base, said second predetermined horizontal direction being perpendicular to said first predetermined horizontal direction, and a guiding part mounted on said second support for movement therewith for guiding said guided part, said guided part and guiding part generating a magnetic force acting therebetween and said guiding part guiding said guided part with said magnetic force; and a position detecting means for detecting an at least two-dimensional position of said guided part, including a magnetic field detecting means for detecting a magnetic field generated by said magnetic field generating means to detect the position of said guided part.

19. A combination of an insertable body and a guiding apparatus for guiding the insertable body within an inspected object, comprising:

an insertable body to be inserted into an inspected object;

a guided part provided in at least a part of said insertable body and to be magnetically guided; and a guiding means outside said inspected object for at least two-dimensionally and magnetically guiding said guided part, said guiding means including a base, a first support connected to said base and which is movable in a first predetermined horizontal direction relative to said base, a second support connected to said first support and which is movable in a second predetermined horizontal direction relative to said base, said second predetermined horizontal direction being perpendicular to said first predetermined horizontal direction, and a guiding part mounted on said second support for movement therewith for guiding said guided part, said guided part and guiding part generating a magnetic force acting therebetween, and said guiding part guiding said guided part with said magnetic force; and a position detecting means for detecting an at least two-dimensional position of said guided part within said inspected object.

20. An endoscope apparatus comprising:

an endoscope including an elongate insertable part having a tip part and an observing window provided in said tip part and to be inserted into an inspected object and an observing means for receiving a light received from said inspected object through said observing window and for obtaining an image of said inspected object;

a guided part provided in at least a part of said insertable part and to be magnetically guided; and guiding means outside said inspected object for magnetically guiding said guided part, said guiding means including a base, a first support connected to said base and which is movable in a first predetermined horizontal direction relative to said base, a second support connected to said first support and which is movable in a second predetermined horizontal direction relative to said base, said second predetermined horizontal direction being perpendicular to said first predetermined horizontal direction, a guiding part mounted on said second support for movement therewith for guiding said guided part, and driving means for moving said guiding part at least two-dimensionally, said guided part and guiding part generating a magnetic force acting therebetween, and said guiding part guiding said guided part with said magnetic force.

* * * * *